US011903872B2

(12) United States Patent
Vergara et al.

(10) Patent No.: US 11,903,872 B2
(45) Date of Patent: Feb. 20, 2024

(54) HEAT EXCHANGE MODULE, SYSTEM AND METHOD

(71) Applicants: THE REGENTS OF THE UNIVERSITY OF CALIFORNIA, Oakland, CA (US); HYPOTHERMIA DEVICES, INC., Los Angeles, CA (US)

(72) Inventors: Julio L. Vergara, Los Angeles, CA (US); Daniel M. Estrada, Los Angeles, CA (US); Mayank Kalra, Los Angeles, CA (US); Andrew Padula, Laguna Niguel, CA (US); Ryan Cohn, Los Angeles, CA (US)

(73) Assignees: THE REGENTS OF THE UNIVERSITY OF CALIFORNIA, Oakland, CA (US); HYPOTHERM DEVICES, INC., Los Angeles, CA (US)

( * ) Notice: Subject to any disclaimer, the term of this patent is extended or adjusted under 35 U.S.C. 154(b) by 1501 days.

(21) Appl. No.: 16/137,124

(22) Filed: Sep. 20, 2018

(65) Prior Publication Data

US 2019/0099288 A1    Apr. 4, 2019

Related U.S. Application Data

(63) Continuation of application No. PCT/US2017/024628, filed on Mar. 28, 2017, which
(Continued)

(51) Int. Cl.
*A61F 7/02* (2006.01)
*A61F 7/00* (2006.01)
(Continued)

(52) U.S. Cl.
CPC ............. *A61F 7/02* (2013.01); *A61F 7/007* (2013.01); *F25B 21/02* (2013.01); *F28F 3/08* (2013.01);
(Continued)

(58) Field of Classification Search
CPC ...... F28F 3/086; F28F 3/10; F28F 3/14; F28F 2270/00; F28F 13/18; F28B 21/02; F28B 21/04; F16B 5/0664; B29C 65/62
See application file for complete search history.

(56) References Cited

U.S. PATENT DOCUMENTS 2,991,627 A    7/1961   Suits
3,196,524 A    7/1965   Jamison
(Continued)

FOREIGN PATENT DOCUMENTS

CA    2980764 A1    10/2016
CN    101309657 A    11/2008
(Continued)

OTHER PUBLICATIONS

National Intellectual Property Administration, PRC (CNIPA), The First Office Action dated Jul. 3, 2019, related China Patent Application No. 201680019132.6, Chinese-language document pp. 1-9, English-language translation p. 10-21, claims examined pp. 22-27.
(Continued)

*Primary Examiner* — Jianying C Atkisson
*Assistant Examiner* — For K Ling
(74) *Attorney, Agent, or Firm* — O'BANION & RITCHEY LLP; John P. O'Banion

(57) ABSTRACT

A heat exchange module alone or part of a system including a control console. The HEM can include a channel enclosure assembly, a thermoelectric cooler (TEC) assembly and a heat transfer (cover) assembly. The enclosure assembly includes a channel for a heat-transfer liquid. The module can
(Continued)

be constructed to provide for flexibility to better conform and fit on rounded and/or angular body parts and to efficiently transfer heat between the adjacent body part and the heat-transfer liquid via the TECs of the TEC assembly.

31 Claims, 39 Drawing Sheets

Related U.S. Application Data is a continuation-in-part of application No. PCT/US2016/024592, filed on Mar. 28, 2016.

(60) Provisional application No. 62/400,836, filed on Sep. 28, 2016.

(51) Int. Cl.
  *F25B 21/02* (2006.01)
  *F28F 9/18* (2006.01)
  *F28F 3/08* (2006.01)

(52) U.S. Cl.
  CPC ........ *F28F 9/18* (2013.01); *A61F 2007/0002* (2013.01); *A61F 2007/0039* (2013.01); *A61F 2007/0056* (2013.01); *A61F 2007/0075* (2013.01); *A61F 2007/0233* (2013.01); *A61F 2007/0255* (2013.01); *F24H 2250/06* (2013.01); *F25B 2321/025* (2013.01); *F25B 2700/21* (2013.01); *F28F 2275/025* (2013.01); *F28F 2275/06* (2013.01); *F28F 2275/085* (2013.01)

(56) References Cited

U.S. PATENT DOCUMENTS

| | | | |
|---|---|---|---|
| 3,827,667 A * | 8/1974 | Lemelson | B22C 9/06 |
| | | | 249/80 |
| 3,867,939 A | 2/1975 | Moore | |
| 4,470,263 A | 9/1984 | Lehovec | |
| 4,494,380 A * | 1/1985 | Cross | F01N 3/00 |
| | | | 62/3.2 |
| 4,560,083 A * | 12/1985 | Danico | B62D 25/24 |
| | | | 220/795 |
| 4,846,176 A * | 7/1989 | Golden | A61F 7/02 |
| | | | 607/104 |
| 4,860,748 A | 8/1989 | Chiurco | |
| 4,879,152 A * | 11/1989 | Green | B32B 27/12 |
| | | | 428/116 |
| 4,962,761 A * | 10/1990 | Golden | A61F 7/02 |
| | | | 607/104 |
| 5,097,829 A * | 3/1992 | Quisenberry | A61F 7/02 |
| | | | 219/490 |
| 5,174,266 A * | 12/1992 | Evdokimo | F02M 31/20 |
| | | | 123/557 |
| 5,174,285 A | 12/1992 | Fontenot | |
| 5,584,183 A | 12/1996 | Wright | |
| 5,603,728 A | 2/1997 | Pachys | |
| 5,653,741 A | 8/1997 | Grant | |
| 5,800,490 A | 9/1998 | Patz | |
| 5,871,526 A | 2/1999 | Gibbs | |
| 5,887,435 A * | 3/1999 | Morton | H05K 7/20709 |
| | | | 361/713 |
| 5,895,418 A | 4/1999 | Saringer | |
| 5,899,077 A | 5/1999 | Wright | |
| 6,019,783 A | 2/2000 | Philips | |
| 6,205,790 B1 | 3/2001 | Denkin | |
| 6,375,674 B1 | 4/2002 | Carson | |
| 6,739,138 B2 | 5/2004 | Saunders | |
| 6,764,502 B2 | 7/2004 | Bieberich | |
| 6,840,955 B2 | 1/2005 | Ein | |
| 7,022,093 B2 | 4/2006 | Smith | |
| 7,077,858 B2 | 7/2006 | Fletcher | |
| 7,637,263 B2 * | 12/2009 | Fisher | H01M 8/241 |
| | | | 128/898 |
| 7,666,215 B2 | 2/2010 | Callister | |
| 7,959,657 B1 | 6/2011 | Harsy | |
| 8,065,763 B2 | 11/2011 | Brykalski | |
| 8,192,474 B2 | 6/2012 | Levinson | |
| 8,283,602 B2 | 10/2012 | Augustine | |
| 9,078,478 B2 | 7/2015 | Ross, Jr. | |
| 9,132,031 B2 | 9/2015 | Levinson | |
| 9,192,474 B2 | 11/2015 | Forsell | |
| 9,278,023 B2 | 3/2016 | Dabrowiak | |
| 9,421,123 B2 | 8/2016 | Lee | |
| 9,962,284 B2 | 5/2018 | Robinson | |
| 10,292,859 B2 | 5/2019 | Levinson | |
| 11,240,882 B2 | 2/2022 | Inaba | |
| 11,458,038 B2 | 10/2022 | Vergara | |
| 2002/0026226 A1 | 2/2002 | Ein | |
| 2002/0120317 A1 | 8/2002 | Fletcher | |
| 2002/0156509 A1 | 10/2002 | Cheung | |
| 2002/0161419 A1 | 10/2002 | Carson | |
| 2003/0097845 A1 | 5/2003 | Saunders | |
| 2004/0158303 A1 | 8/2004 | Lennox | |
| 2004/0159109 A1 | 8/2004 | Harvie | |
| 2005/0065581 A1 | 3/2005 | Fletcher | |
| 2005/0143797 A1 * | 6/2005 | Parish | A61F 7/007 |
| | | | 607/104 |
| 2006/0280948 A1 | 12/2006 | Moreshead | |
| 2006/0293732 A1 | 12/2006 | Collins | |
| 2008/0046047 A1 * | 2/2008 | Jacobs | A61F 7/007 |
| | | | 607/108 |
| 2008/0077201 A1 | 3/2008 | Levinson | |
| 2008/0077211 A1 | 3/2008 | Levinson | |
| 2008/0097560 A1 | 4/2008 | Radziunas | |
| 2008/0097562 A1 | 4/2008 | Tan | |
| 2008/0188915 A1 | 8/2008 | Mills | |
| 2008/0249524 A1 | 10/2008 | Dunning | |
| 2008/0287839 A1 | 11/2008 | Rosen | |
| 2009/0000309 A1 | 1/2009 | Hershberger | |
| 2009/0155838 A1 | 6/2009 | Hale | |
| 2009/0264969 A1 | 10/2009 | Gammons | |
| 2009/0312822 A1 | 12/2009 | Besner | |
| 2010/0132930 A1 | 6/2010 | Izenson | |
| 2010/0198322 A1 | 8/2010 | Joseph | |
| 2010/0280581 A1 | 11/2010 | Cushman | |
| 2011/0030754 A1 | 2/2011 | Smythe | |
| 2011/0071603 A1 | 3/2011 | Moore | |
| 2011/0238050 A1 | 9/2011 | Allison | |
| 2011/0297358 A1 * | 12/2011 | Russell | C23D 5/04 |
| | | | 977/773 |
| 2012/0118344 A1 | 5/2012 | Schluck | |
| 2012/0239123 A1 | 9/2012 | Weber | |
| 2013/0012388 A1 | 1/2013 | Song | |
| 2013/0013033 A1 | 1/2013 | Lowe | |
| 2013/0085552 A1 | 4/2013 | Mandel | |
| 2013/0172829 A1 | 7/2013 | Badawi | |
| 2014/0222121 A1 * | 8/2014 | Spence | A61F 7/02 |
| | | | 607/104 |
| 2014/0228718 A1 * | 8/2014 | Diller | A61N 1/0456 |
| | | | 607/104 |
| 2014/0228918 A1 | 8/2014 | Brienza | |
| 2014/0276257 A1 | 9/2014 | Santa Maria | |
| 2014/0311543 A1 | 10/2014 | Jinushi | |
| 2014/0326287 A1 | 11/2014 | Wiant | |
| 2014/0352325 A1 | 12/2014 | Brown | |
| 2015/0080989 A1 | 3/2015 | Mohn | |
| 2015/0182375 A1 * | 7/2015 | Binversie | A61F 7/007 |
| | | | 601/18 |
| 2015/0223971 A1 | 8/2015 | Zaveri | |
| 2015/0238349 A1 * | 8/2015 | Giuliani | A61F 7/00 |
| | | | 602/2 |
| 2015/0366703 A1 | 12/2015 | Du | |
| 2016/0035957 A1 | 2/2016 | Casey | |
| 2016/0178251 A1 | 6/2016 | Johnson | |
| 2016/0270952 A1 | 9/2016 | Vergara | |
| 2017/0027053 A1 | 1/2017 | Moczygemba | |
| 2018/0098903 A1 | 4/2018 | Vergara | |

(56) References Cited

U.S. PATENT DOCUMENTS

| | | |
|---|---|---|
| 2018/0204993 A1 | 7/2018 | Himmer |
| 2019/0099287 A1 | 4/2019 | Vergara |
| 2019/0262169 A1 | 8/2019 | Vergara |

FOREIGN PATENT DOCUMENTS

| | | |
|---|---|---|
| CN | 103142217 A | 6/2013 |
| CN | 203341808 U | 12/2013 |
| DE | 4238291 A1 | 5/1994 |
| DE | 202006020386 U1 | 7/2008 |
| EP | 3278047 A1 | 2/2018 |
| JP | H04077915 | 7/1992 |
| JP | H04077915 Y | 7/1992 |
| JP | 2003323219 | 11/2003 |
| JP | 2006230761 | 9/2006 |
| JP | 2006230761 A | 9/2006 |
| JP | 2008546510 A | 12/2008 |
| JP | 2009501067 A | 1/2009 |
| JP | 2010515481 | 5/2010 |
| JP | 2011067638 | 4/2011 |
| KR | 1020080060193 | 1/2008 |
| KR | 1020140140617 | 12/2014 |
| KR | 20150083559 A | 7/2015 |
| SU | 1179987 A1 | 9/1985 |
| TW | 201110282 A | 3/2011 |
| WO | 0195841 A2 | 12/2001 |
| WO | 0195841 A3 | 12/2001 |
| WO | 02064069 A2 | 8/2002 |
| WO | 2002064069 A2 | 8/2002 |
| WO | 2004111741 A1 | 12/2004 |
| WO | 2007005073 A2 | 1/2007 |
| WO | 2008039556 A1 | 4/2008 |
| WO | 2008039557 | 4/2008 |
| WO | 2008039557 A1 | 4/2008 |
| WO | 2008085162 A1 | 7/2008 |
| WO | 2011156643 A1 | 12/2011 |
| WO | 2013124866 A2 | 8/2013 |
| WO | 2013144008 A1 | 10/2013 |
| WO | 2014001789 A1 | 1/2014 |
| WO | 2014057450 A1 | 4/2014 |
| WO | 2015048170 | 4/2015 |
| WO | 2015048170 A | 4/2015 |
| WO | 2015048170 A1 | 4/2015 |
| WO | 2016160691 | 10/2016 |
| WO | 2016160691 A1 | 10/2016 |
| WO | 2017171719 | 10/2017 |
| WO | 2017171719 A1 | 10/2017 |
| WO | 2017172836 | 10/2017 |
| WO | 2018064220 A1 | 4/2018 |
| WO | 2018064428 | 4/2018 |
| WO | 2018064428 A1 | 4/2018 |

OTHER PUBLICATIONS

Mexican Institute of the Industrial Property, office action dated Oct. 27, 2022, related Mexican patent application MX/a/2019/003346, pp. 1-3, English translation 4-6, with claims examined, pp. 7-20.
Korean Intellectual Property Office (KIPO), International Search Report and Written Opinion, counterpart PCT international patent application No. PCT/US2014/057276, dated Jan. 8, 2015, pp. 1-17, with claims searched, pp. 18-21.
European Patent Office (EPO), extended European search report dated Mar. 29, 2017, related European patent application No. 14849500.5, pp. 1-8, with claims searched, pp. 9-11.
ISA/US, United States Patent and Trademark Office (USPTO), International Search Report and Written Opinion dated Jul. 1, 2016, related PCT international application No. PCT/US2016/024501, pp. 1-19, with claims searched, pp. 20-25.
ISA/US, United States Patent and Trademark Office (USPTO), International Search Report and Written Opinion dated Sep. 14, 2016, related PCT international application No. PCT/US2016/024592, pp. 1-13, with claims searched, pp. 14-17.
IP Australia, Patent Examination Report 1 dated May 24, 2018, related Australian patent application No. 2014326780, pp. 1-4, with claims examined, pp. 5-7.
ISA/US, United States Patent and Trademark Office (USPTO), International Search Report and Written Opinion dated Aug. 28, 2017, related PCT international application No. PCT/US2017/024628, pp. 1-23, with claims searched, pp. 24-46.
ISA/US, United States Patent and Trademark Office (USPTO), International Search Report and Written Opinion dated Mar. 8, 2018, related PCT international application No. PCT/US2017/053812, pp. 1-16, with claims searched, pp. 17-35.
ISA/US, United States Patent and Trademark Office (USPTO), International Search Report and Written Opinion dated Feb. 6, 2018, related PCT international application No. PCT/US2017/054196, pp. 1-18, with claims searched, pp. 19-32.
Japan Patent Office (JPO), official action dated Jul. 31, 2018, related Japanese patent application No. 2016-517424, Japanese-language document pp. 1-6, English-language translation pp. 7-12, claims examined pp. 13-16.
Japan Patent Office (JPO), official action dated Jun. 16, 2020, related Japanese patent application No. 2019-074530, pp. 1-7, English-language translation (partial), pp. 8-12, claims examined, pp. 13-17.
Korean Intellectual Property Office (KIPO), official action dated Jun. 4, 2020, related Korean patent application No. 10-2018-7028057, pp. 1-4, English-language translation, pp. 5-7, claims examined, pp. 8-11.
State Intellectual Property Office of the People's Republic of China, The First Office Action dated Jul. 29, 2020, related Chinese patent application No. 201780020778.0, pp. 1-14, English-language translation, pp. 15-33, claims examined, pp. 34-58.
IP Australia, Examination report No. 1 for standard patent application dated Aug. 26, 2020, related Australian patent application No. 2016243565, pp. 1-5, claims examined, pp. 6-11.
State Intellectual Property Office of the People's Republic of China, The Third Office Action dated Feb. 28, 2022, related Chinese patent application No. 201780066498.3, pp. 1-3, English-language translation, pp. 4-8, claims examined, pp. 5-13.
Canadian Intellectual Property Office, office action dated May 27, 2022, related Canadian patent application No. 2,980,764, pp. 1-3, claims examined, pp. 4-9.
European Patent Office (Epo), Communication pursuant to Article 94(3) EPC dated Dec. 12, 2020, repated European patent application No. EP 16773916.8, pp. 1-8, claims examined, p. 9-10.
Canadian Intellectual Property Office, office action dated Dec. 29, 2020, related Canadian patent application No. 2,925,094, pp. 1-8, claims examined, pp. 9-12.
Japan Patent Office, official action dated Jan. 5, 2021, related Japanese patent application No. 2017-549684, pp. 1-4, English-language translation, pp. 5-7, claims examined, pp. 8-12.
IP Australia, Examination report No. 2 for standard patent application dated Aug. 26, 2020, related Australian patent application No. 2016243565, pp. 1-6, claims examined, pp. 7-11.
Korean Intellectual Property Office, official action dated Jan. 11, 2021, prepared Korean patent application No. 10-2016-7007807, pp. 1-11, English-language translation, pp. 12-14, claimls examined, pp. 15-18.
The Patent Office of the People's Repubic of China, official action dated Jan. 12, 2021, related Chinese patent application No. 2017800664983, pp. 1-6, Englis-language translation, pp. 7-15, claims examined, pp. 16-29.
IP Australia, Examination report No. 1 for standard patent application dated Feb. 21, 2022, related Australian patent application No. 2017335975, pp. 1-5, claims examined, pp. 6-19.
IPEA/US, United States Patent and Trademark Office (USPTO), International Preliminary Report on Patentability dated Sep. 10, 2018, related PCT international application No. PCT/US2016/024592, pp. 1-12, claims, pp. 13-20, drawings, pp. 21-46, Article 34 amendment, pp. 47-56.
IP Australia, Examination report No. 2 dated Dec. 6, 2018, related Australian patent application No. 2014326780, pp. 1-7, claims examined, pp. 8-11.

(56) References Cited

OTHER PUBLICATIONS

Japan Patent Office (JPO), Decision of Refusal dated Dec. 11, 2018, related Japanese patent application No. 2016-517424, Japanese-language document pp. 1-6, English-language translation pp. 7-11, claims examined pp. 12-15.

European Patent Office (EPO), Communication (Extended European Search Report) dated Oct. 18, 2018, related European patent application No. 16773916.8, pp. 1-9, claims searched, pp. 10-12.

Intellectual Property India, Examination Report dated Jan. 24, 2020, related India patent application No. 201647009683, pp. 1-6, claims examined, pp. 7-10.

Japan Patent Office (Jpo), official action dated Apr. 21, 2020, related Japanese patent application No. 2016-517424, pp. 1-4, English-language translation pp. 5-8, claims examined pp. 9-12.

State Intellectual Property Office of the People's Republic of China, The Second Office Action dated Mar. 26, 2020, related Chinese patent application No. 201680019132.6, pp. 1-9, English-language translation, pp. 10-24, claims examined, pp. 25-32.

Japan Patent Office (JPO), official action dated Mar. 10, 2020, related Japanese patent application No. 2017-549684, pp. 1-5, English-language translation , pp. 6-10, claims examined, pp. 11-16.

Korean Intellectual Property Office (KIPO), official action dated Mar. 9, 2020, related Korean patent application No. 10-2017-7030302, pp. 1-7, English-language translation, pp. 8-10, claims examined, pp. 11-16.

Japan Patent Office (JPO), official action dated Mar. 17, 2020, related Japanese patent application No. 2018-550772, pp. 1-7, English-language translation, pp. 8-15, claims examined, pp. 16-19.

Japan Patent Office (Jpo), official action dated May 10, 2022, related Japanese patent application No. 2019-516508, pp. 1-3, English-language translation, pp. 4-6, claims examined, pp. 7-13.

IPEA/US, United States Patent and Tradmark Office (USPTO), International Preliminary Report on Patentability dated Oct. 21, 2019, related PCT international application No. PCT/US2017/054196, pp. 1-16, claims, pp. 17-45, Article 34 amendment, pp. 46-53.

European Patent Office (EPO), Communication (extended European search report) dated Sep. 25, 2019, related European patent application No. EP 16897277.6, pp. 1-9, claims searched, pp. 10-12.

European Patent Office (EPO), Communication (extended European search report) dated Oct. 22, 2019, related European patent application No. EP 17776506.2, pp. 1-12, claims searched, pp. 13-15.

European Patent Office (EPO), Communication (extended European search report) dated Apr. 8, 2020, related European patent application No. EP 17857465.3, pp. 1-8, claims searched, pp. 9-11.

Japan Patent Office (JPO), official action dated Aug. 31, 2021, related Japanese patent application No. 2019-516508, pp. 1-6, English-language translation, pp. 7-12, claims examined, pp. 13-20.

IPEA/US, United States Patent and Trademark Office, International Preliminary Report on Patentability dated Mar. 8, 2019, related PCT international application No. PCT/US2017/024628, pp. 1-9, claims examined, pp. 10-34.

European Patent Office (EPO), Communication pursuant to Article 94(3) EPC dated June, 1, 2021, related European patent application No. 14 849 500.5, pp. 1-6, claims examined, pp. 7-10.

Korean Intellectual Property Office, Notice of Preliminary Rejection dated Jul. 16, 2021, related Korean patent application No. 10-2018-7028696, pp. 1-7, English-language translation, pp. 8-11, claims examined, pp. 12-24.

State of Israel Ministry of Justice the Patent Authority, Notification No. 26, dated Dec. 1, 2021, related Israel patent application No. 265686, pp. 1-4, English-language translation, pp. 5-8, claims examined, pp. 9-19.

Japan Patent Office (JPO), official action dated Dec. 20, 2021, related Japanese patent application No. 2018-551821, pp. 1-3, English-language translation pp. 4-6, claims examined, pp. 7-35.

The Patent Office of the People's Republic of China, official action dated Jan. 6, 2022, related Chinese patent application No. 201680084088.7, pp. 1-10, English-language machine translation, pp. 11-19, claims examined, pp. 20-23.

Korean Intellectual Property Office, official action dated Feb. 16, 2022, related Korean patent application No. 10-2019-7009157, pp. 1-7, English-language translation, pp. 8-11, claims examined, pp. 12-25.

\* cited by examiner

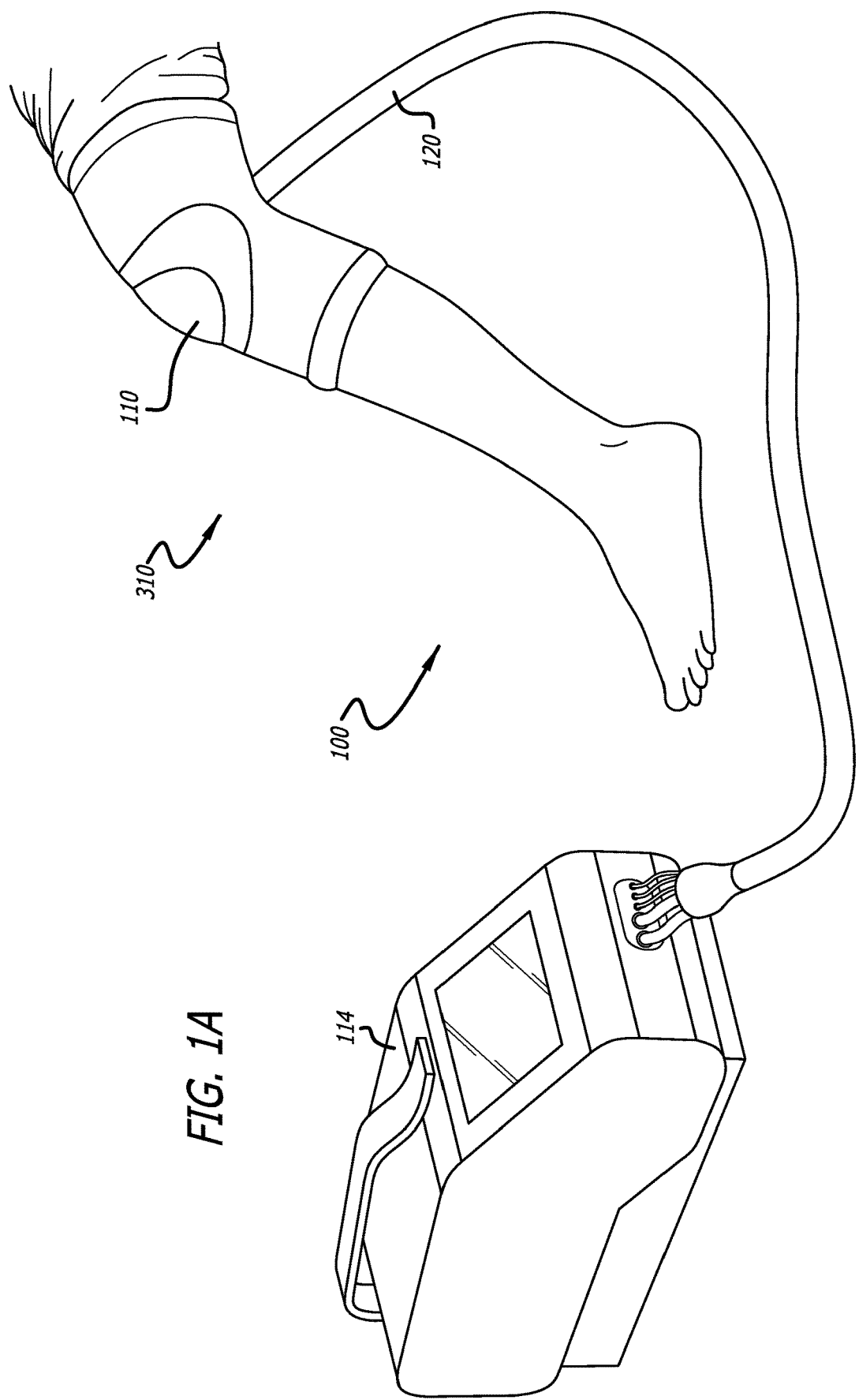

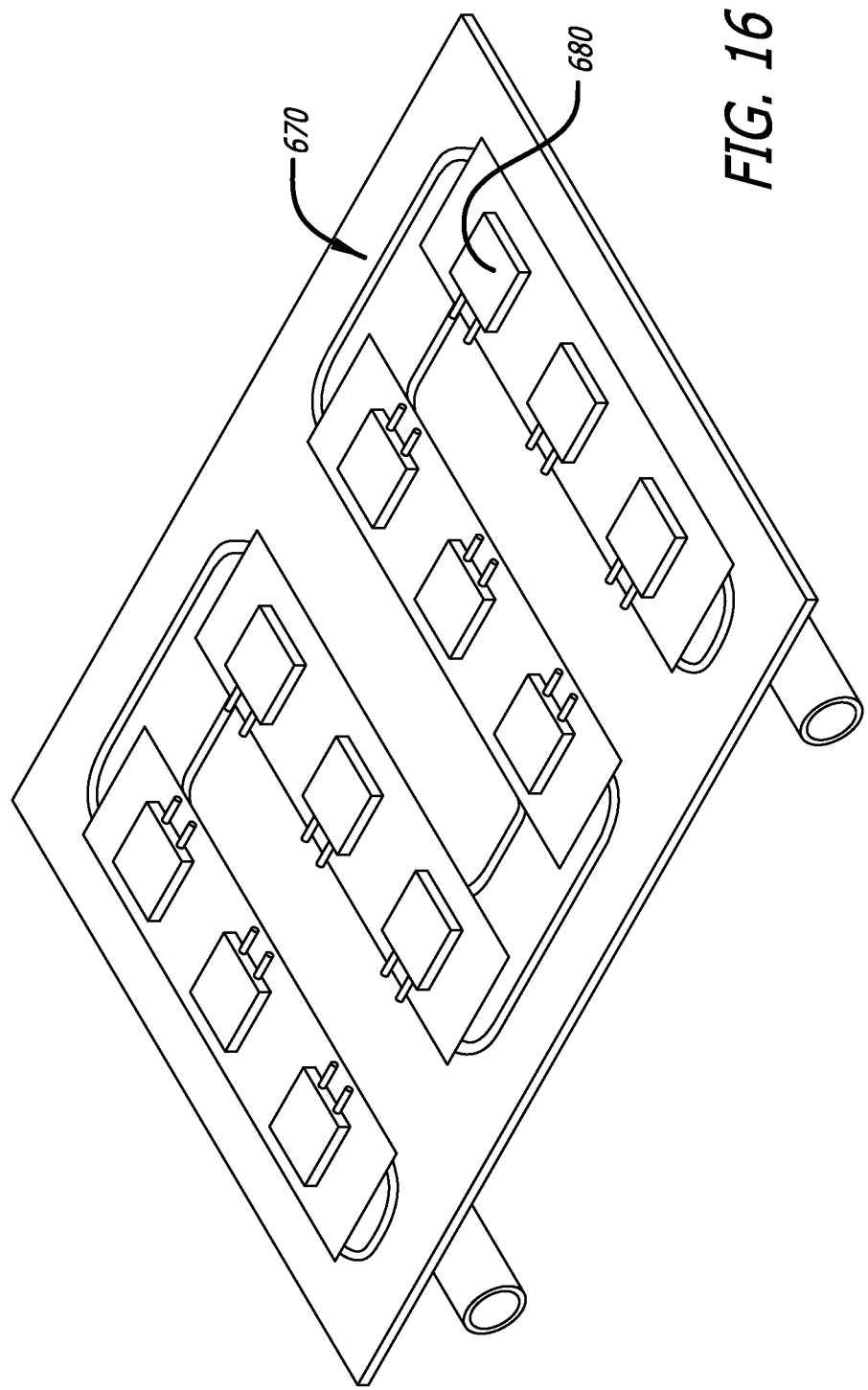

HEAT EXCHANGE MODULE, SYSTEM AND METHOD

CROSS-REFERENCE TO RELATED APPLICATIONS

This application claims priority to, and is a 35 U.S.C. § 111(a) continuation of, PCT international application number PCT/US2017/024628 filed on Mar. 28, 2017, incorporated herein by reference in its entirety, which was published as PCT International Publication No. WO 2017/172836 A1 on Oct. 5, 2017, incorporated herein by reference in its entirety, and which claims priority to, and the benefit of, U.S. provisional patent application Ser. No. 62/400,836 filed on Sep. 28, 2016, incorporated herein by reference in its entirety, and which also claims priority to, and is a 35 U.S.C. § 111 (a) continuation-in-part of, PCT international application number PCT/US2016/024592 filed on Mar. 28, 2016, incorporated herein by reference in its entirety, which was published as PCT International Publication No. WO 2017/171719 A1 on Oct. 5, 2017, incorporated herein by reference in its entirety. Priority is claimed to each of the foregoing applications.

This application is related to PCT international application number PCT/US2014/057276 filed on Sep. 24, 2014, incorporated herein by reference in its entirety, which was published as PCT International Publication No. WO 2015/045170 A1 on Apr. 2, 2015, incorporated herein by reference in its entirety, and which claims priority to, and the benefit of, U.S. provisional patent application Ser. No. 61/884,932 filed on Sep. 30, 2013, incorporated herein by reference in its entirety.

This application is related to PCT international application number PCT/US2016/024501 filed on Mar. 28, 2016, incorporated herein by reference in its entirety, which was published as PCT International Publication No. WO 2016/160,691 A1 on Oct. 6, 2016, incorporated herein by reference in its entirety, and which claims priority to, and the benefit of, U.S. provisional patent application Ser. No. 62/139,676 filed on Mar. 28, 2015, incorporated herein by reference in its entirety.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

An aspect of the technology of this disclosure pertains generally to flexible heat exchange modules (HEMs) that contain thermoelectric coolers (TECs) and can be used for heating or cooling.

Hypothermia treatment of patients is used for a variety of applications, including but not limited to treatment of brain injuries, spinal cord injuries, muscle injuries, joint injuries, and as a neuroprotective agent for cardiac arrest and neonatal hypoxic ischemic encephalopathy. This treatment is typically afforded by the use of ice packs and/or chemical cool packs that provide incomplete and short-lived cooling, or by pads or caps in which cooling is afforded by circulating chilled water.

SUMMARY

A heat exchange module (HEM) is disclosed herein having a channel enclosure assembly, a thermoelectric cooler (TEC) assembly and a heat transfer (or cover) assembly. The enclosure assembly includes a liquid channel, and can be formed from radio frequency (RF) or ultrasonically welded plastic films. Every TEC of the TEC assembly transfers heat to the liquid directly or indirectly through a sealed window in the channel wall. For example, the reference side of the TEC can be mounted in the window thereby closing the window and forming a part of the channel wall, or a thermally-conductive (typically copper or aluminum) plate piece can be mounted in the window with the reference side of the TEC in thermal contact with the backside of the plate piece. The heat transfer (cover) assembly can include a slotted heat transfer plate (typically copper, aluminum, or other very high thermal conductivity material), or a plurality of interconnected tiles (small plates made of copper, aluminum, or other heat conductive material) for positioning against a body part. The user side of the TEC is in heat transfer relation with the slotted plate or one of the tiles, depending on the embodiment. A thermistor (or a thermocouple) is positioned on an inward face of the slotted plate or the tile. Thereby, the TEC assembly controllably, using input from a thermistor or thermocouple, or a plurality of thermistors or thermocouples, adjusts the temperature of the body part by expelling heat into, or withdrawing heat from, the heat-transfer liquid.

The channel enclosure assembly can be constructed of three flexible sheets. The first and second sheets have aligned holes and the above-mentioned plate piece can be embedded in and between the sheets, covering the holes. The first and second sheets are secured to a third (top) sheet (such as a reinforced TPU sheet) which is heat compressed, or RF welded, or ultrasonically welded, to the second sheet to form a serpentine channel therebetween with the second sheet. A top surface of the plate piece is at a hole in a channel portion of the second sheet, thereby forming part of the wall of the channel and in direct contact with the liquid flowing in the channel for heat transfer therebetween.

Multiple plate pieces are typically embedded in and between the first and second sheet, spaced from the previously-mentioned plate piece and also forming parts of the channel wall. Reference sides of respective TECs of the TEC assembly are attached to the back sides of each of the plate pieces, through respective holes in the first sheet.

For the tile embodiment, the cover (heat transfer) assembly can include a flexible (plastic) frame having open windows. Trays arranged in an array are each interconnected to adjacent trays by flexible bridges. Each tray has a hole for receiving and holding a respective TEC, and through which the user faces of the TECs are secured to respective ones of the tiles. The matrix of interconnected trays and the plurality of tiles are held together by snapping or hooking into the frame at respective ones of the windows. The frame keeps the tiles spaced such that the layer of tiles is flexible along one or more X-axes between tiles, as well as one or more Y-axes. Thereby the HEM is flexible and conformable against rounded and/or angular body parts by flexing on the axes between the tiles as well as axes between the plate pieces. Separate thermistors (or thermocouples) can be mounted on inward surfaces of each tile but not so as to interfere with the TEC attachments.

The liquid that is passed through the channel in the enclosure assembly acts as a heat sink for the TECs contained within the HEM. Power is supplied by a controller to the TECs to induce cooling or heating.

The controller can be located in a console of a system of the present disclosure which also includes the HEM and an umbilical providing electrical, signal and water (fluid) connection between the HEM and the console. The console contains a combination of radiator and fans that efficiently dissipates the heat transferred to and from the fluid circulating at the HEM by using the umbilical as a conduit. The HEM may be used for heating, cooling or cycling between heating and cooling for various medical uses. One or more temperature sensors (e.g., thermistors or thermocouples) detect the temperature of the cooling or heating surface and may be used as feedback to the control unit.

A HEM herein can use a pair of flexible substrates to form open channels using radio-frequency (RF) welding or similar method. The resulting channels may be used to pass a liquid to dissipate heat out of the HEM. The liquid that is passed through the closed channels acts as a heat sink for the TECs contained within the device. Power is supplied by a controller to the TECs to induce cooling or heating.

One or more temperature sensors detect the temperature of the cooling or heating surface and may be used as feedback to the control unit. The HEM may be used for heating, cooling, or cycling between heating and cooling for various medical uses.

The HEM can include a heat exchange stack attached to a water channel assembly, both of which are discussed below according to embodiments of the disclosure.

Heat exchange stacks herein can be assemblies that allow for direct cooling and/or heating of tissue or skin. They can be comprised of all the heat exchange module's components except for the water channel assembly and the biocompatible layer that interfaces with a patient's tissue or skin. In this assembly there is a cover that distributes the cooling or heating of the thermoelectric coolers which interfaces with the biocompatible layer, a core composite for interstitial insulation and structural stability, up to two sheets of reflective material to prevents radiation, at least one thermistor for temperature feedback, the thermoelectric cooler array for cooling and heating, and an additional cover or plates for heat dissipation which will be interfaced with the water channels. This last array of plates or cover can be made such that there is an increased flexibility in the heat exchange stack. This assembly of components, except for the biocompatible layer unless specified for the design, can then be mechanically fastened with methods including sewing or riveting to make the heat exchange stack. The water channels may or may not already be attached for the fastening process, again depending on the design.

Water channels herein can be assemblies that create paths for fluid to pass near or against the heat exchange stack in order to dissipate the heat produced by the heat exchange stack. They can be constructed pursuant to various methods including radio frequency welded plastic films.

The present application includes a number of different definitions of the disclosures including the module or device, subassemblies of the method or device (such as the heat exchange stack and the water channels), methods of making the module or device, methods of making the subassemblies, the console, the umbilical, the overall system, methods of making the devices and subassemblies, and methods of using the devices, systems and subassemblies thereof. That is, the present disclosure includes a number of different definitions of the disclosures including the module or device, subassemblies of the method or device (such as the water channel enclosure assembly), the heat transfer (or cover) assembly, methods of making the module or device, methods of making the subassemblies, the console, the umbilical, the overall system, methods of making the devices and subassemblies, and methods of using the devices, systems and subassemblies thereof.

Further aspects of the technology described herein will be brought out in the following portions of the specification, wherein the detailed description discloses preferred embodiments of the technology without placing limitations thereon.

BRIEF DESCRIPTION OF THE DRAWINGS

FIG. 1A is a perspective view of a system of the present disclosure shown in operation on a patient to cool and/or heat a muscle, joint and/or tissue for multiple uses, including but not limited to the treatment of sport injuries and pain management.

FIG. 16 is a view similar to FIG. 11 and showing the thermoelectric cooler (TEC) assembly in place on the plates.

DETAILED DESCRIPTION

1. Overview

Figure 28:
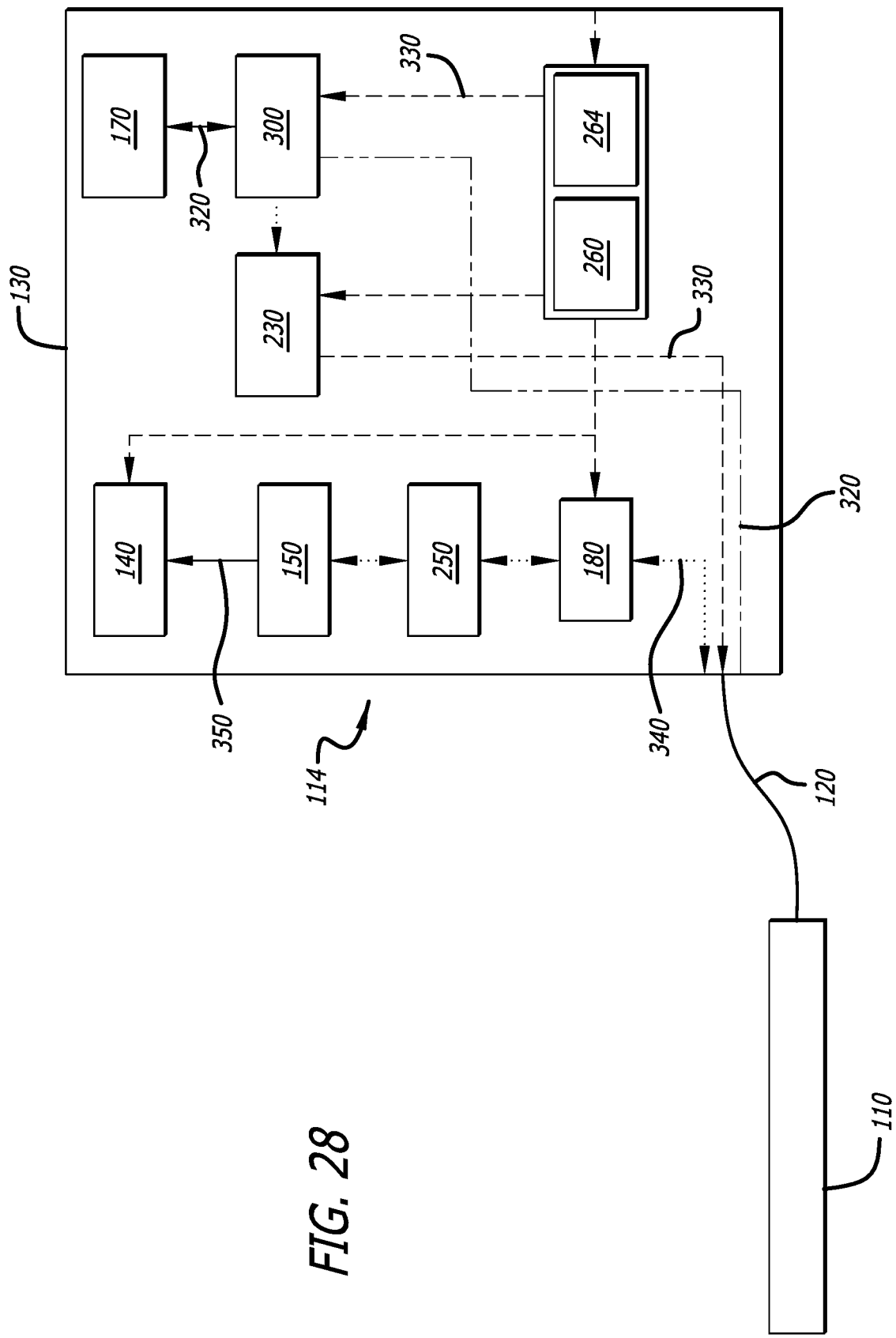
FIG. 28 is a schematic overview of a system of the present disclosure including a module connected by an umbilical to a console and the operational relationships of the components of the console illustrated.
Figure 29:
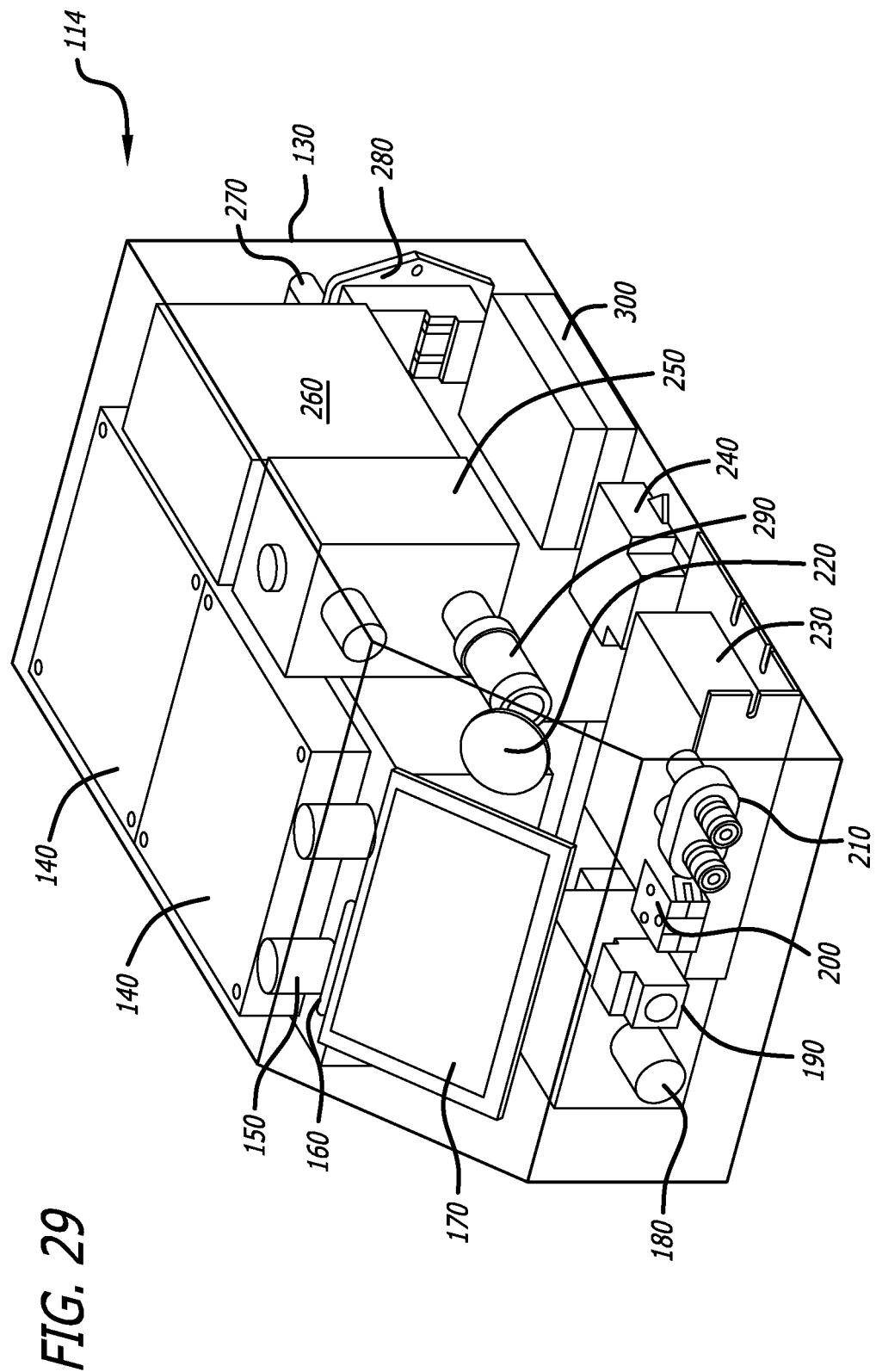
FIG. 29 is a perspective view of the console of FIG. 28 with the enclosure in transparent for illustrative purposes.
Figure 30:
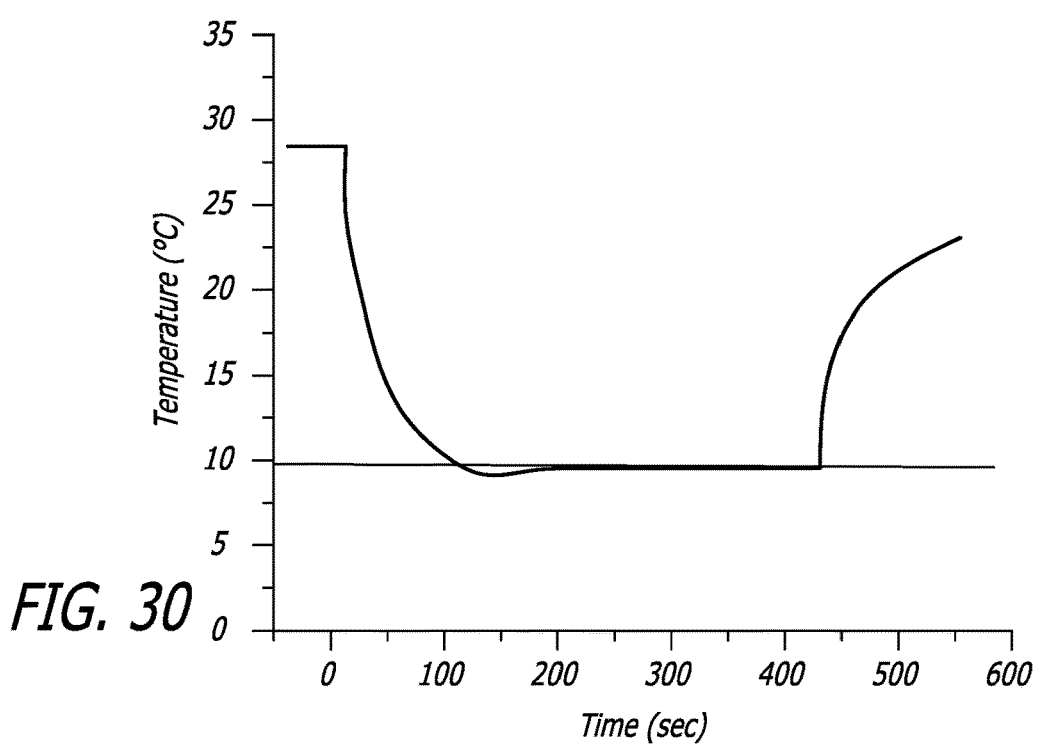
FIG. 30 is a graph showing temperature changes measured on the thigh of an individual in response to controlled cooling to 10 degrees C. for approximately seven minutes.
Figure 31:
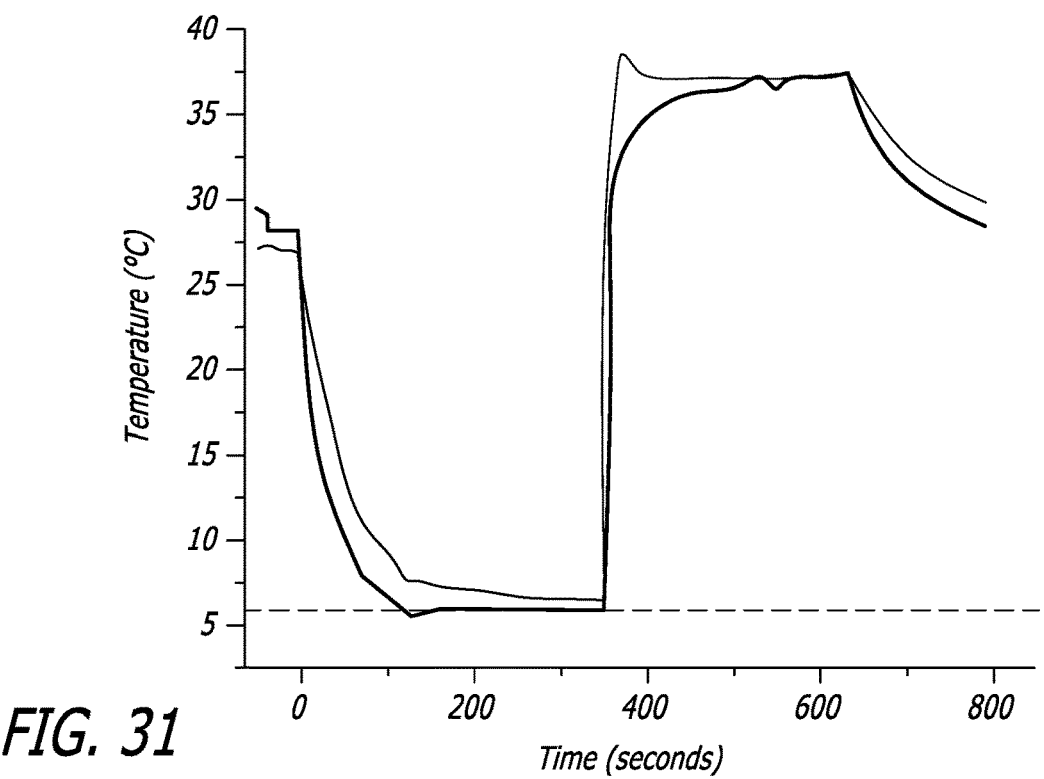
FIG. 31 is a graph of temperature versus time measured on the skin of the hand of an individual in response to cooling (to 5 degrees C.) and heating (to 36 degrees C.) using controlled profiles of the heat exchange module.

Referring to the system overviews of FIGS. 28 and 29 illustrated therein are the heat exchange systems shown generally at 100 and including a heat exchange module shown generally at 110, a console shown generally at 114 and an umbilical 120 operatively connecting them. The console includes an enclosure 130, fans 140, radiator 150, screen drive board 160, touch screen 170, pump 180, jack 190, power/signal plug 200, port connector 210, rotary encoder 220, H-bridge 230, DC to DC power supply 240, reservoir 250, battery 260, USB 270, power outlet 280, flow meter 290, microcontroller assembly 300.

Various systems of this disclosure are shown in FIGS. 1A, 1B, 1C and 1D generally at 310, 320, 330 and 340 respectively. FIG. 28 shows the following connections signal 320, power 330, fluid 340, and heat 350.

Figure 1B:
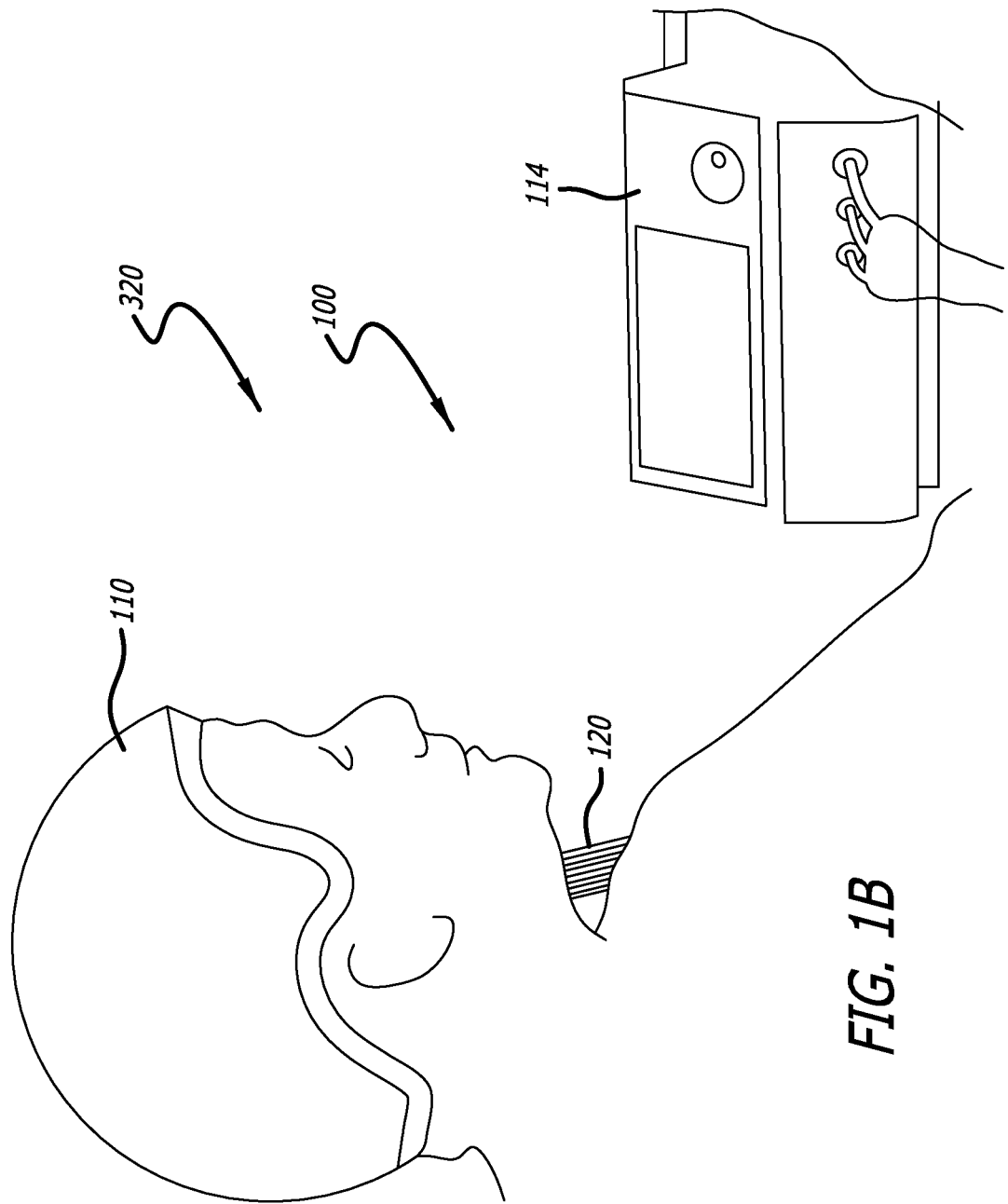
FIG. 1B is a perspective view of a system of the present disclosure shown in operation on a patient to cool and/or heat the scalp for multiple uses, including but not limited to the treatment of chemotherapy hair loss prevention.
Figure 1C:
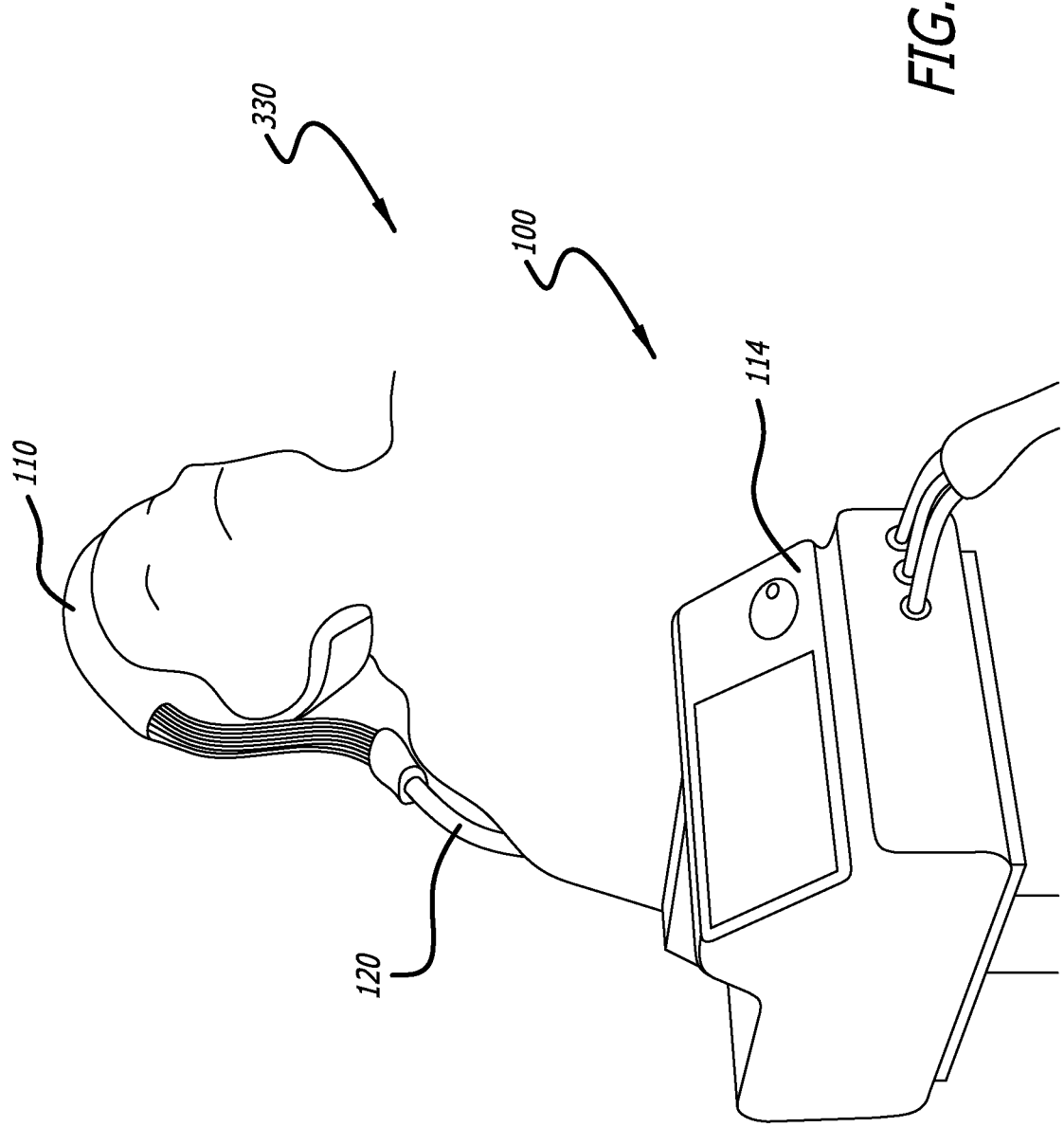
FIG. 1C is a perspective view of a system of the present disclosure shown in operation on a patient to the scalp and/or the brain for multiple uses, including but not limited to the treatment of traumatic brain injury or stroke application.
Figure 1D:
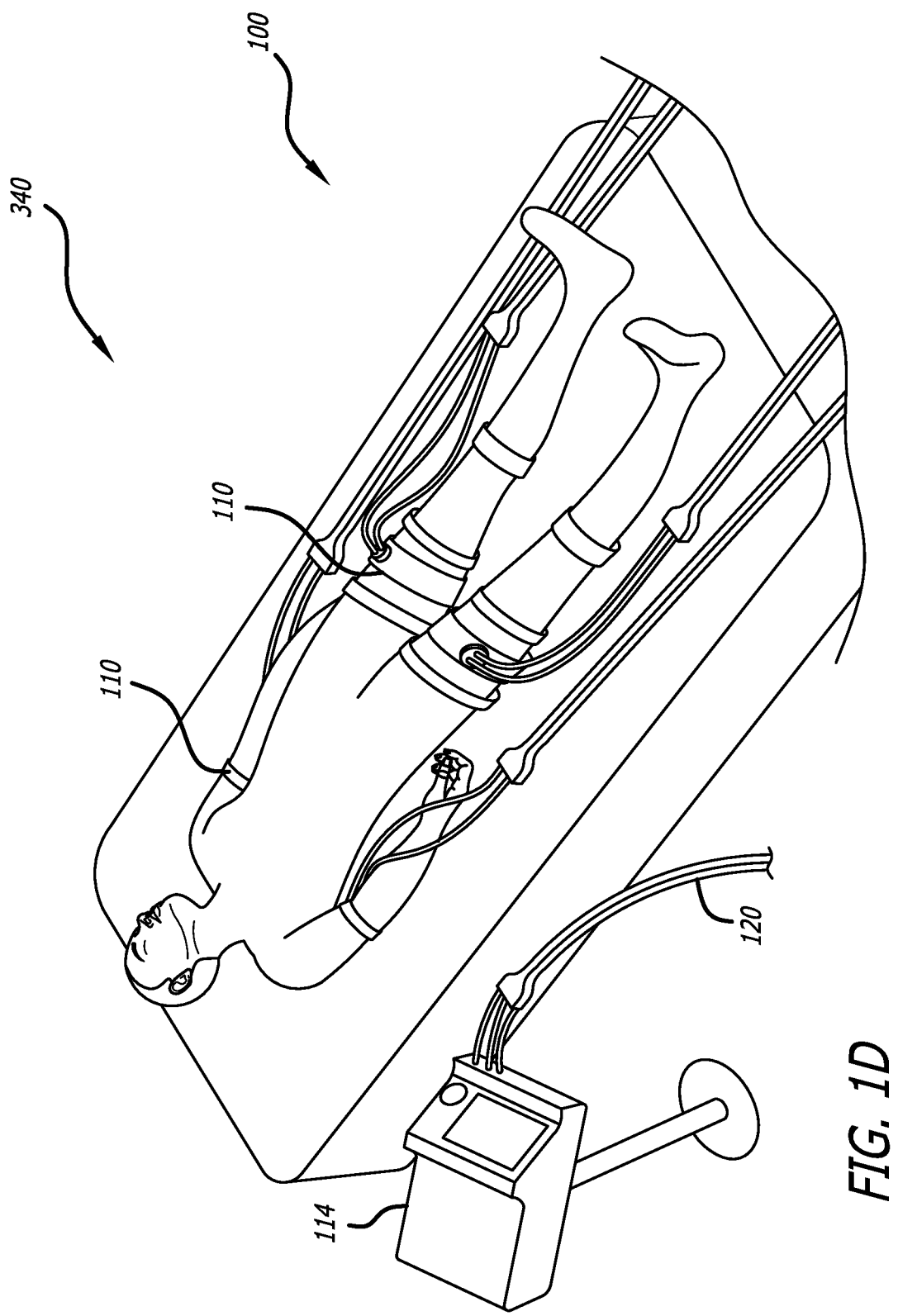
FIG. 1D is a perspective view of a system of the present disclosure shown in operation to regulate cool and/or heat core temperature of a patient for multiple uses, including but not limited to the treatment of cardiac arrest.
Figure 2:
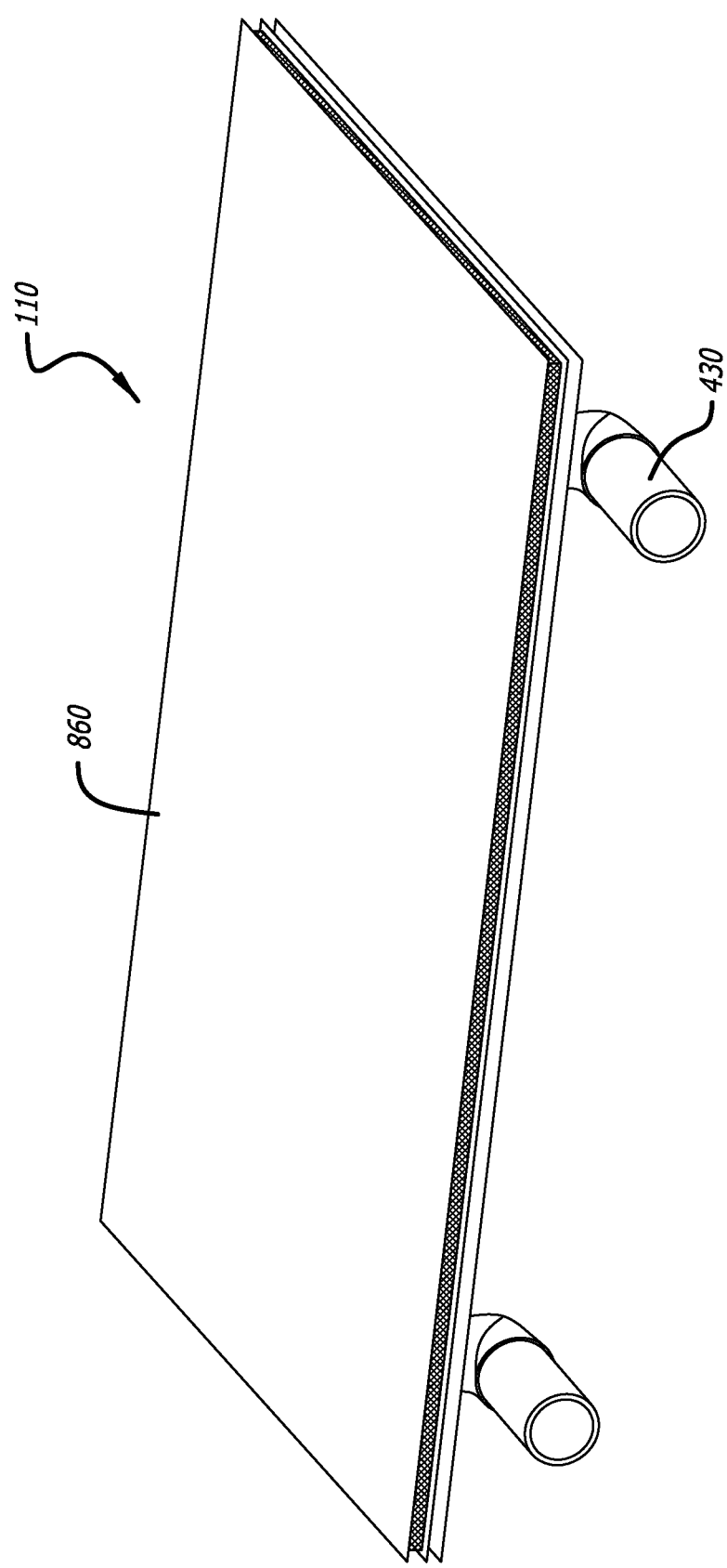
FIG. 2 is a perspective view of a heat exchange module of the present disclosure shown in isolation and such as can be used in the systems of FIGS. 1A-1D.
Figure 3:
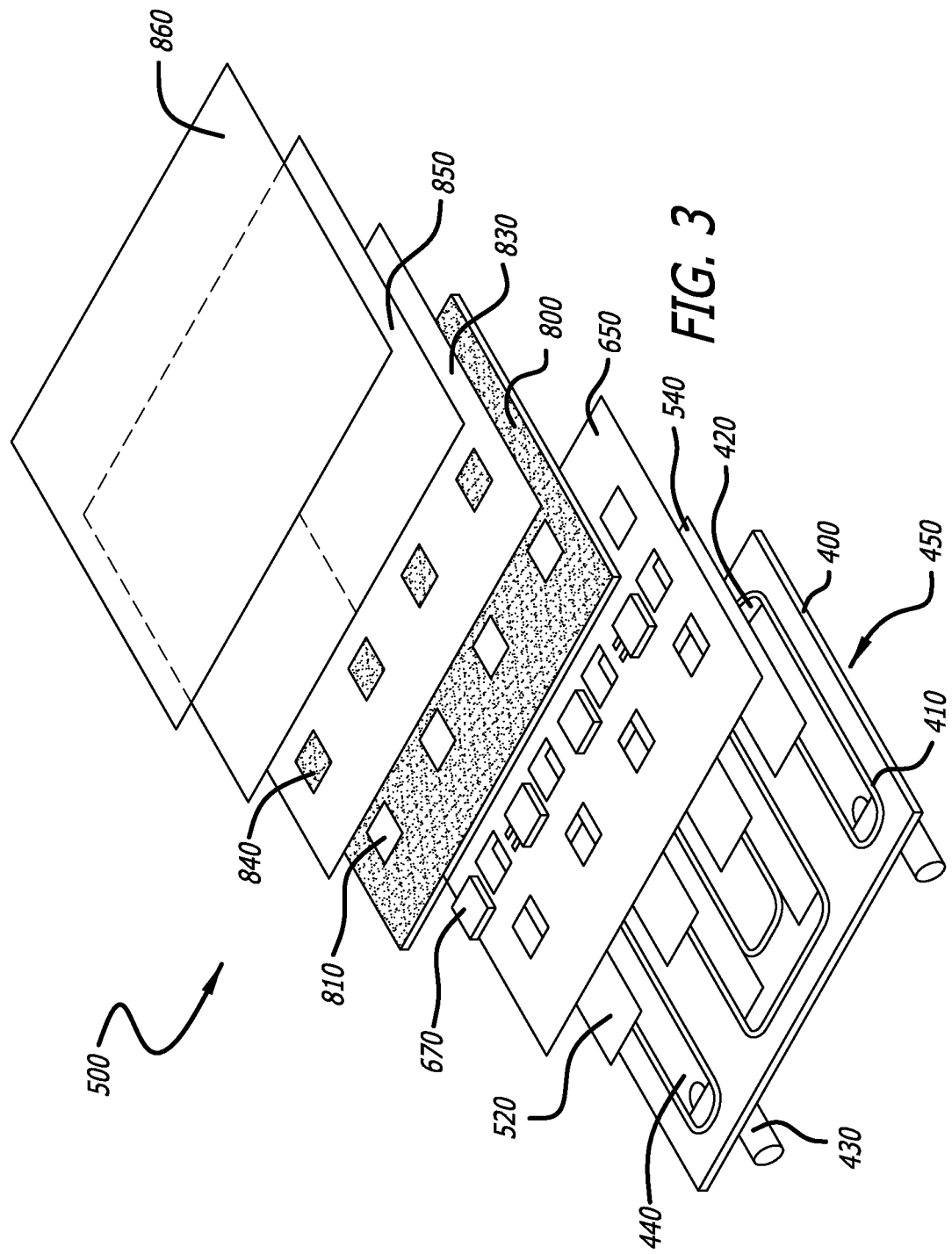
FIG. 3 is an exploded perspective view of the module of FIG. 2.
Figure 4:
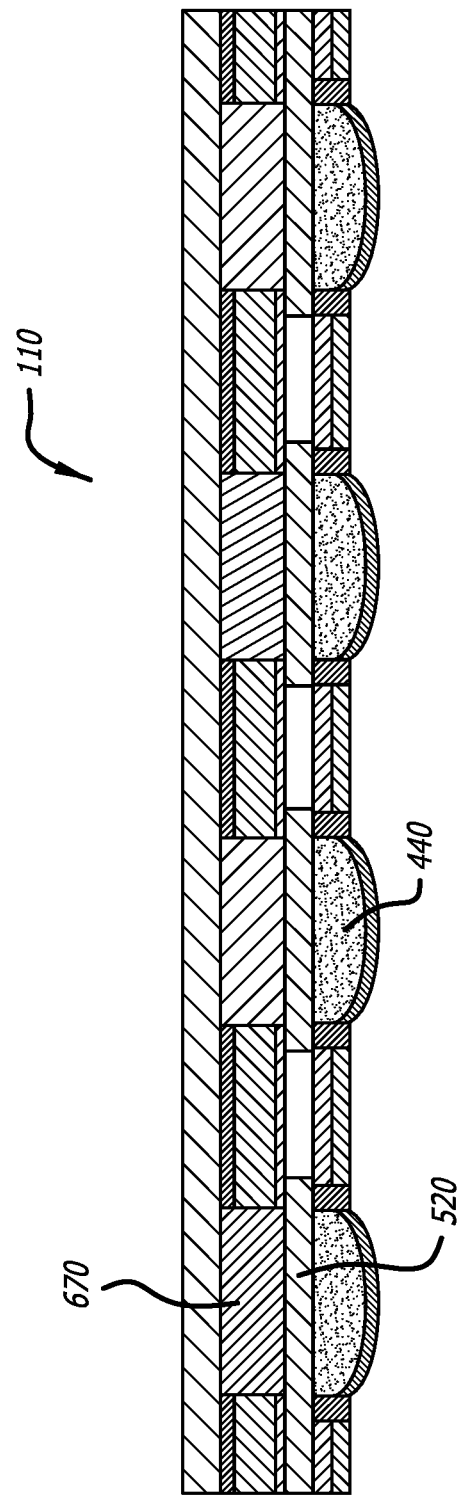
FIG. 4 is a stylized cross-sectional view of the module of FIG. 2.
Figure 5:
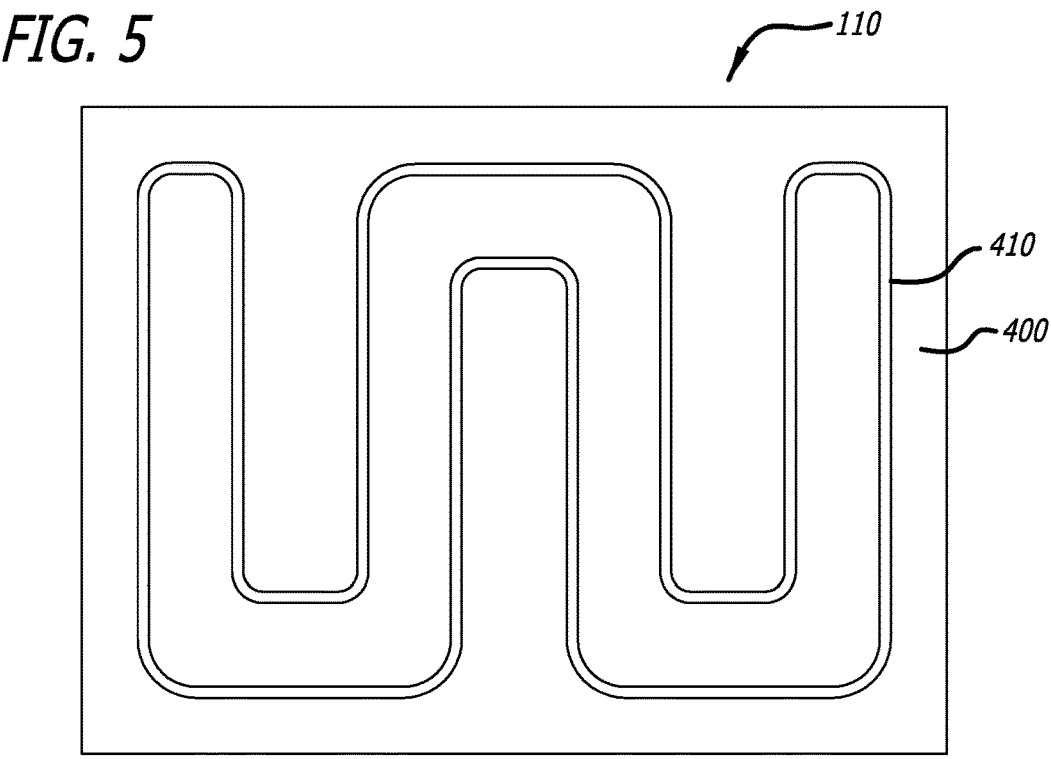
FIG. 5 is a plan view of a channel design of a channel assembly of a module of the disclosure.
Figure 6:
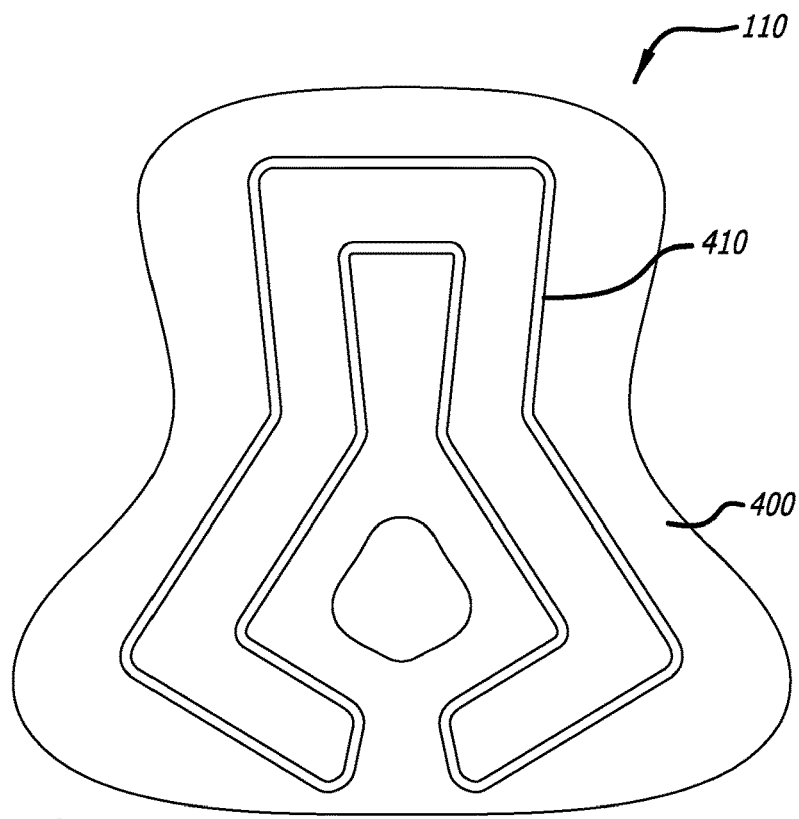
FIG. 6 is a view similar to FIG. 5 of an alternative channel design.

FIG. 3 is an exploded perspective view of one of the modules 110 showing the various layers including two TPU sheets 400, RF welded 410 to form a channel 420, with angled inlet and outlet 430. The channel has a plurality of windows (openings) 440 cut out to expose the interior of the channel at a plurality of locations. The sheets, channel with openings and outlet form a water channel shown generally at 450.

Figure 12A:
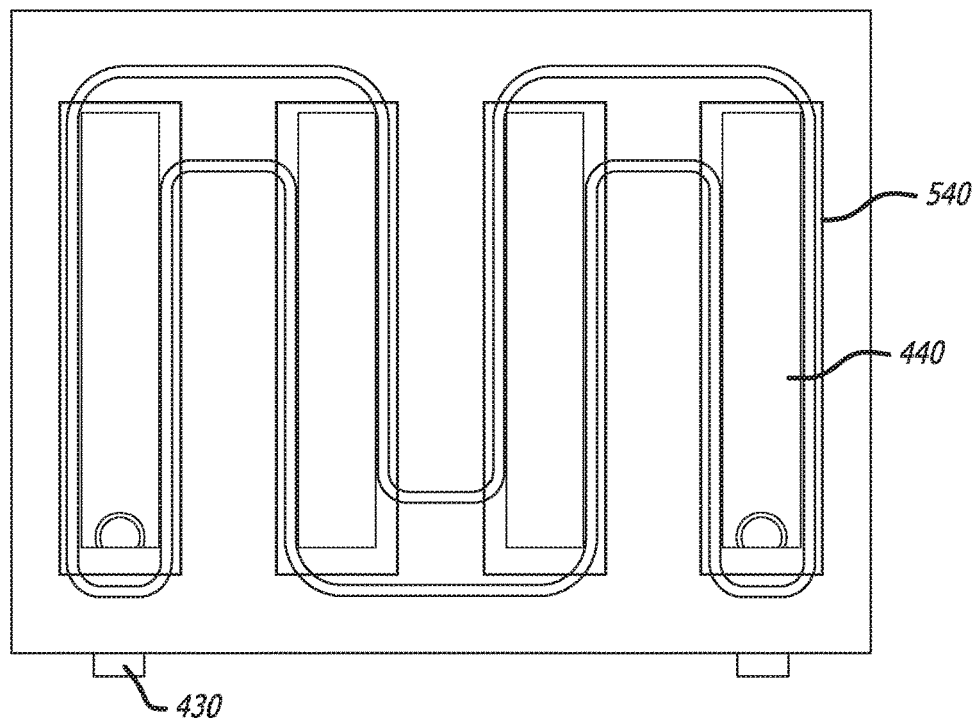
FIG. 12A is a view similar to FIG. 11 showing the plates as transparent so the backside adhesive on the plates can be seen in the channel assembly for illustrative purposes.
Figure 12B:
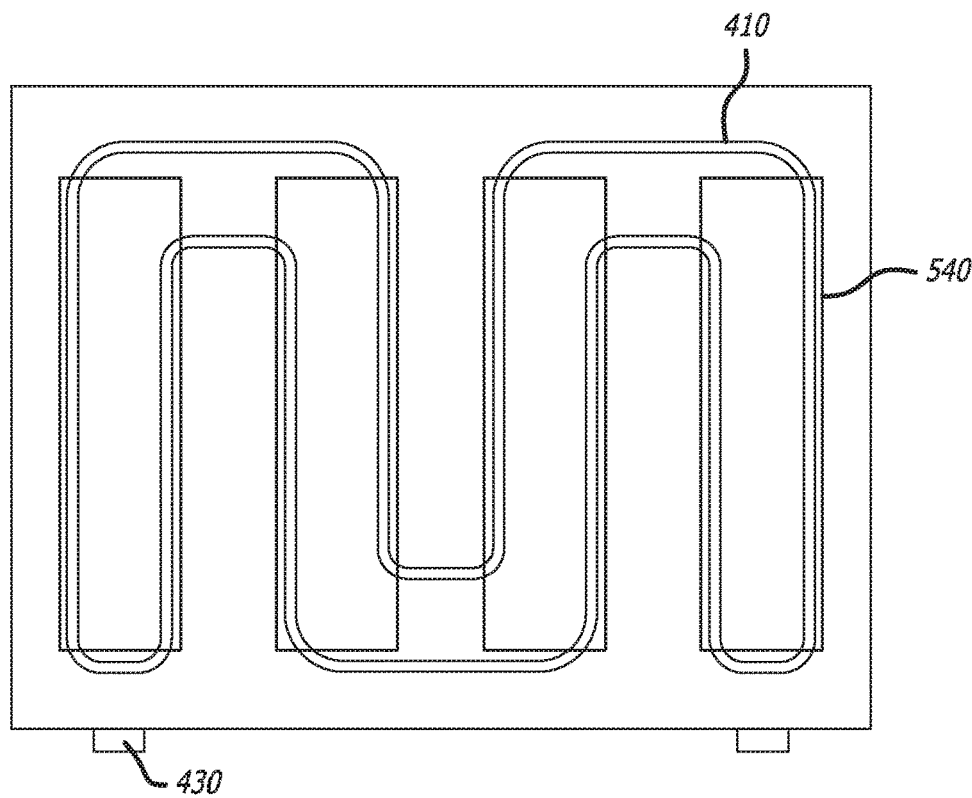
FIG. 12B is a view similar to FIG. 12A showing the backside of the channel assembly but with the alternative embodiment in which the windows are not cut out, keeping the water channel layer intact.
Figure 15A:
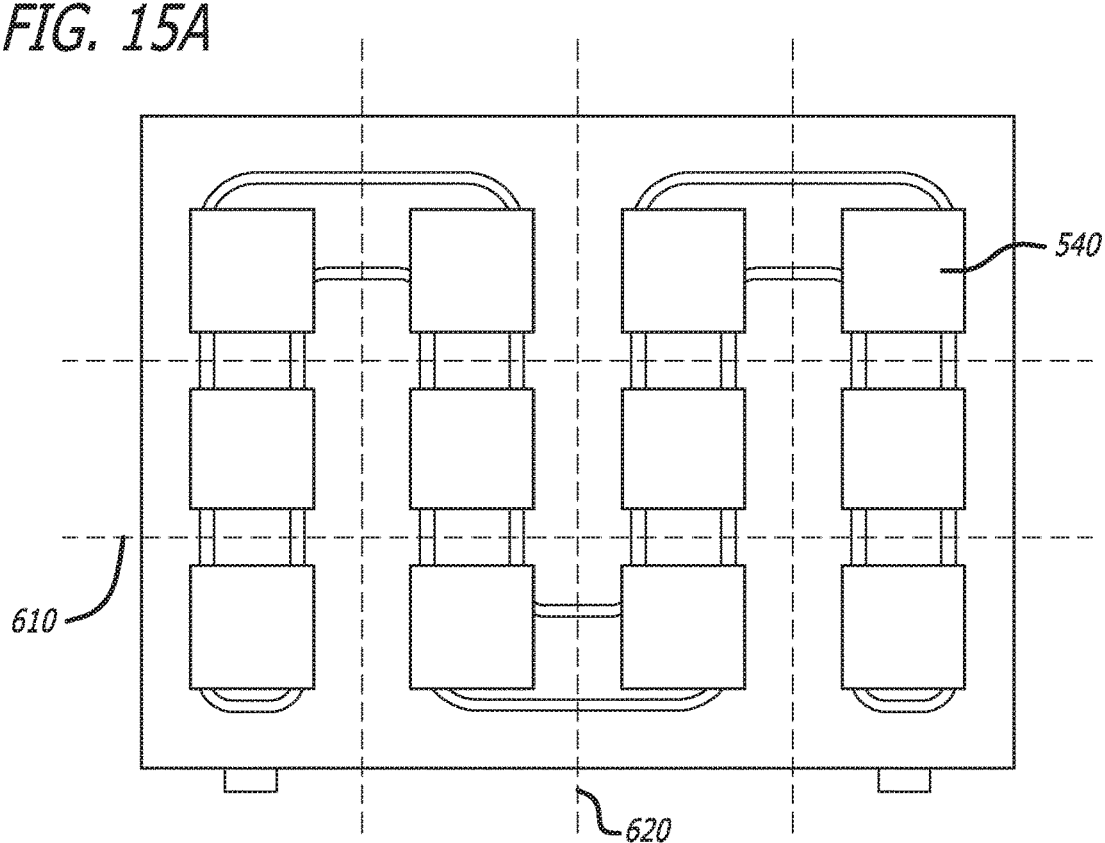
FIG. 15A is a view similar to FIG. 11 but of an alternative embodiment having twelve instead of four plates and thereby providing more axes of rotation flexibility, three in the Y direction and two in the X direction.
Figure 15B:
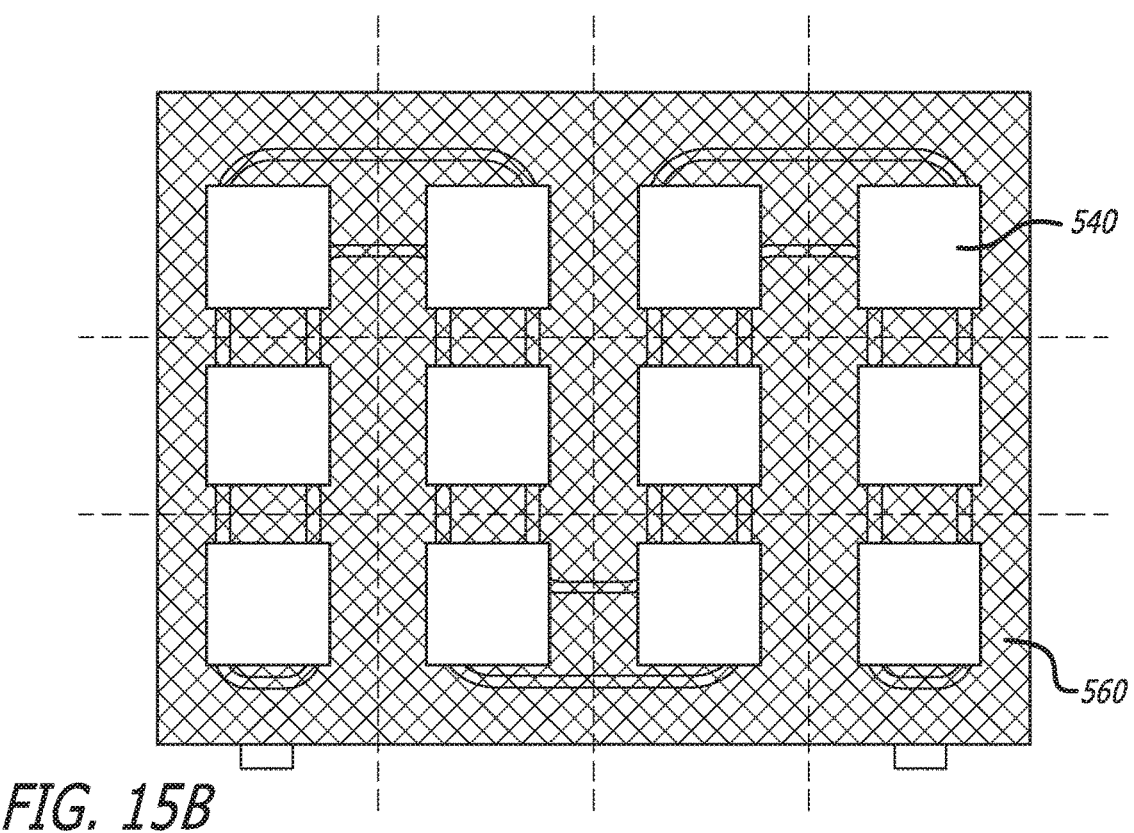
FIG. 15B is a view similar to FIG. 15A but of an alternative embodiment connecting the twelve plates with another cover illustrated by a hashed pattern.
Figure 17:
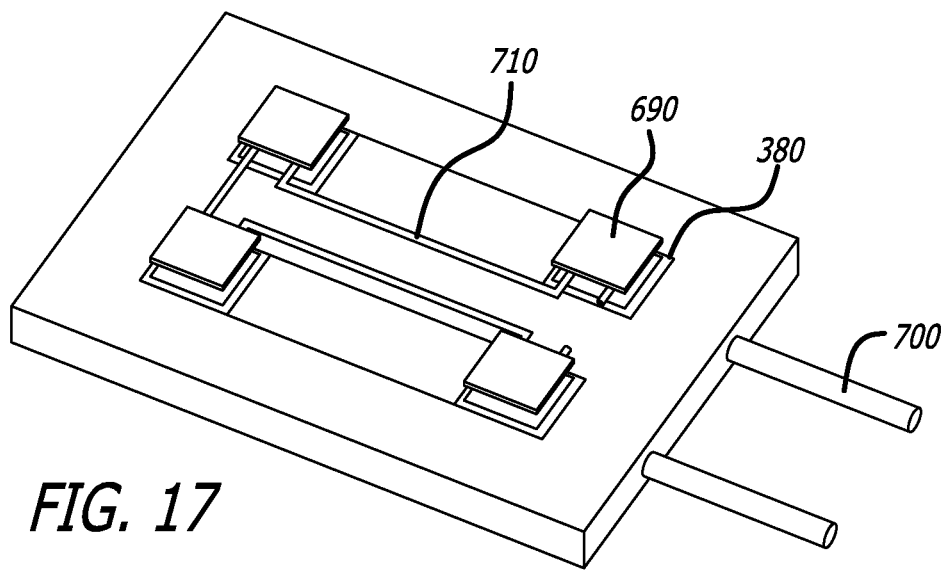
FIG. 17 shows in perspective an alternative TEC assembly and thermally conductive plate arrangement with the details of the TEC assembly.
Figure 18:
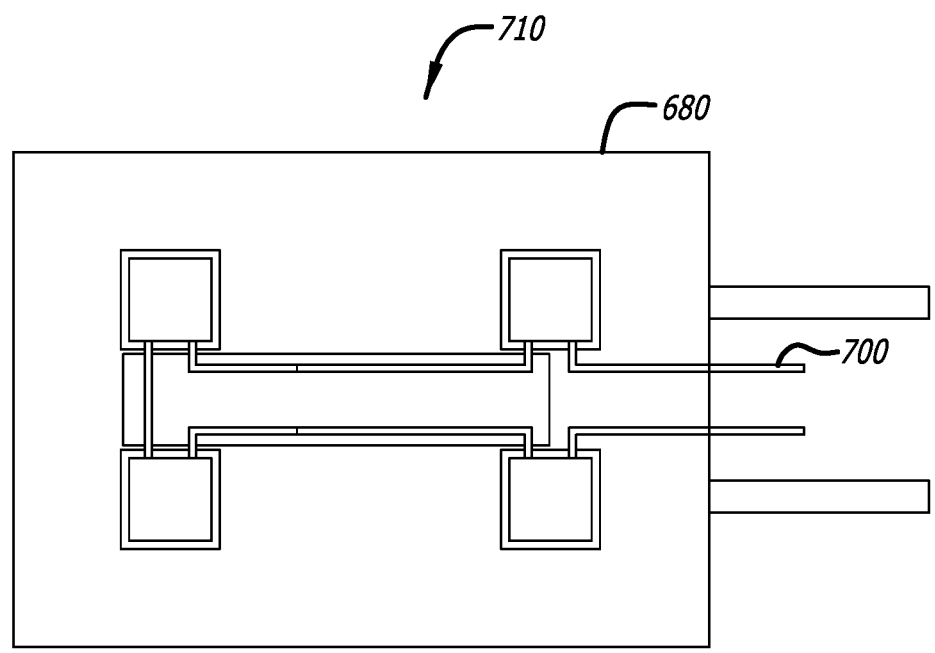
FIG. 18 is a top plan view of FIG. 17.
Figure 19:
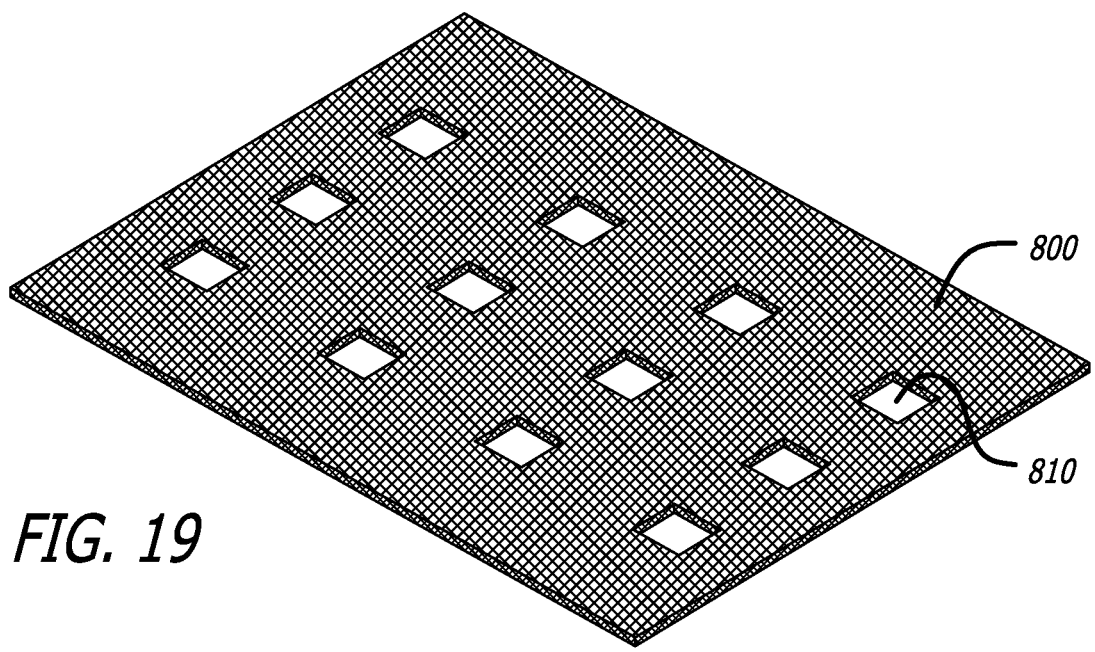
FIG. 19 is perspective view of a core composite layer of the module shown in isolation and before configuring.
Figure 20:
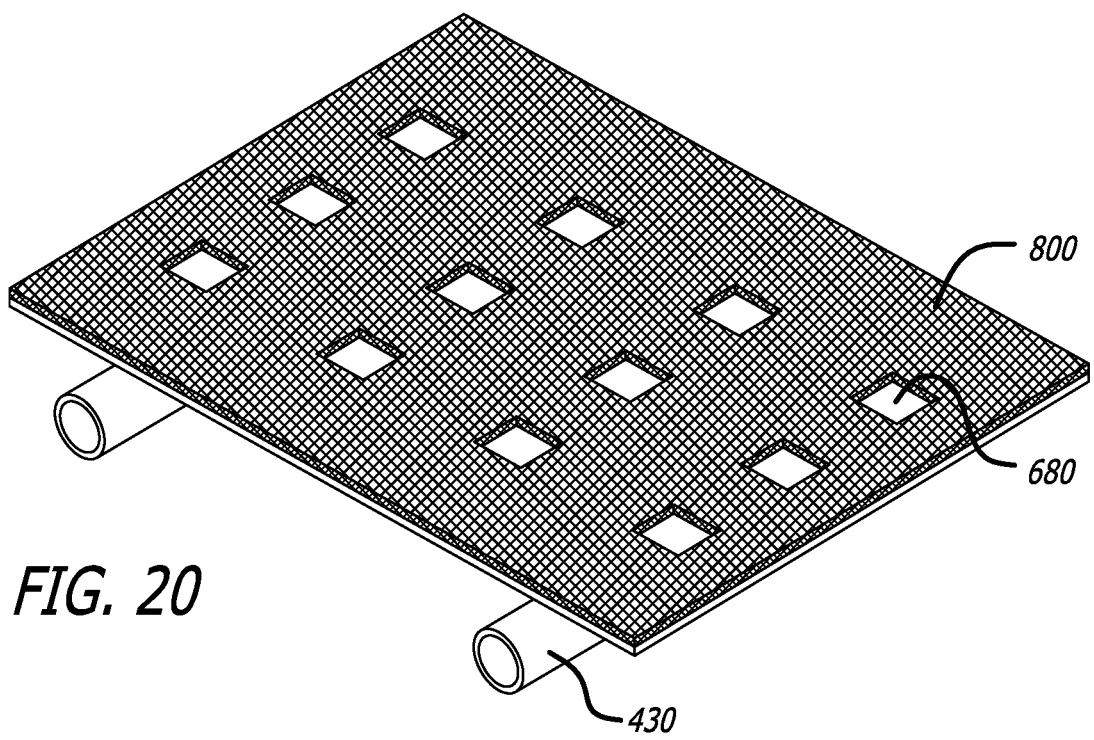
FIG. 20 is a perspective view similar to FIG. 16 with the core composite layer of FIG. 19 configured and in place.
Figure 21:
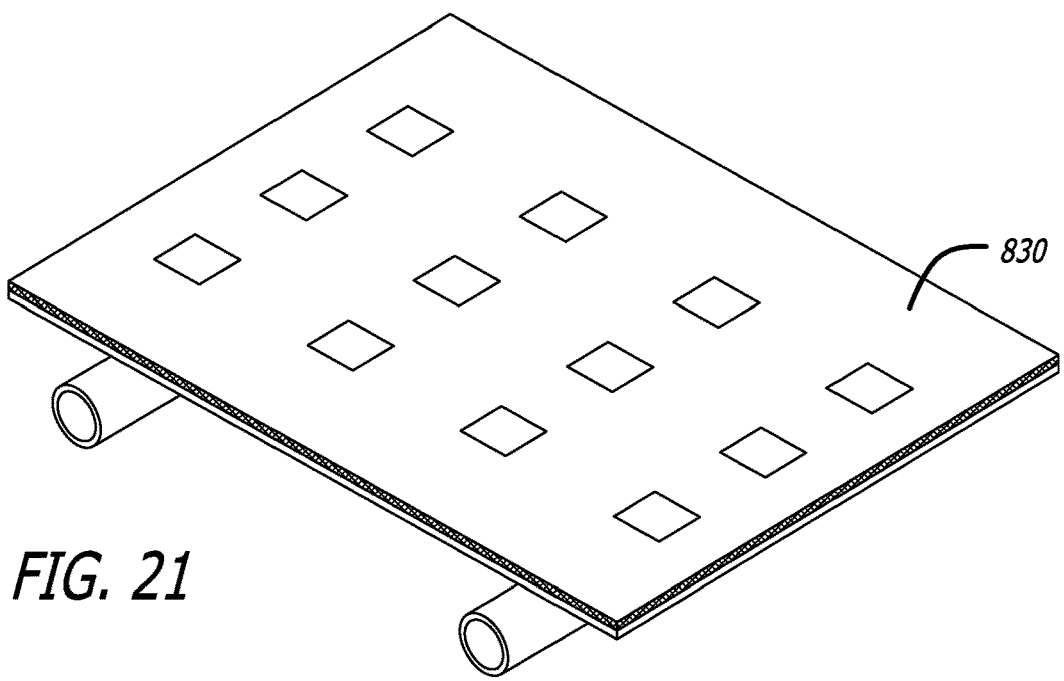
FIG. 21 is a view similar to FIG. 20 with the upper Mylar sheet in place on top of the core composite layer.
Figure 22:
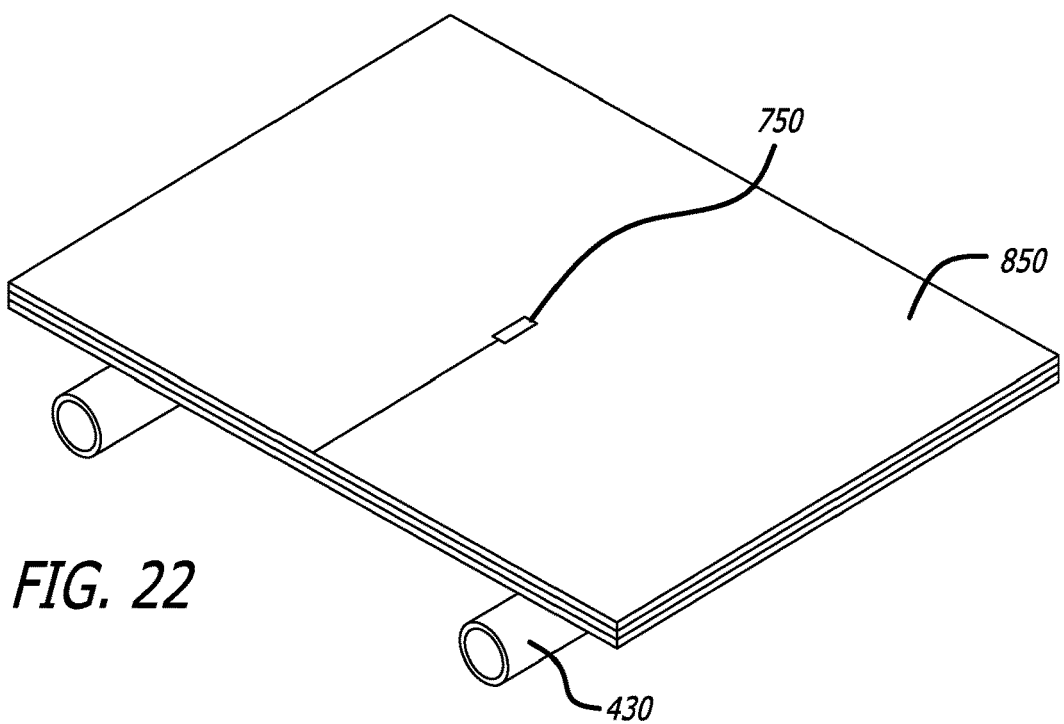
FIG. 22 is a view similar to FIG. 21 with the top plate in place.
Figure 23:
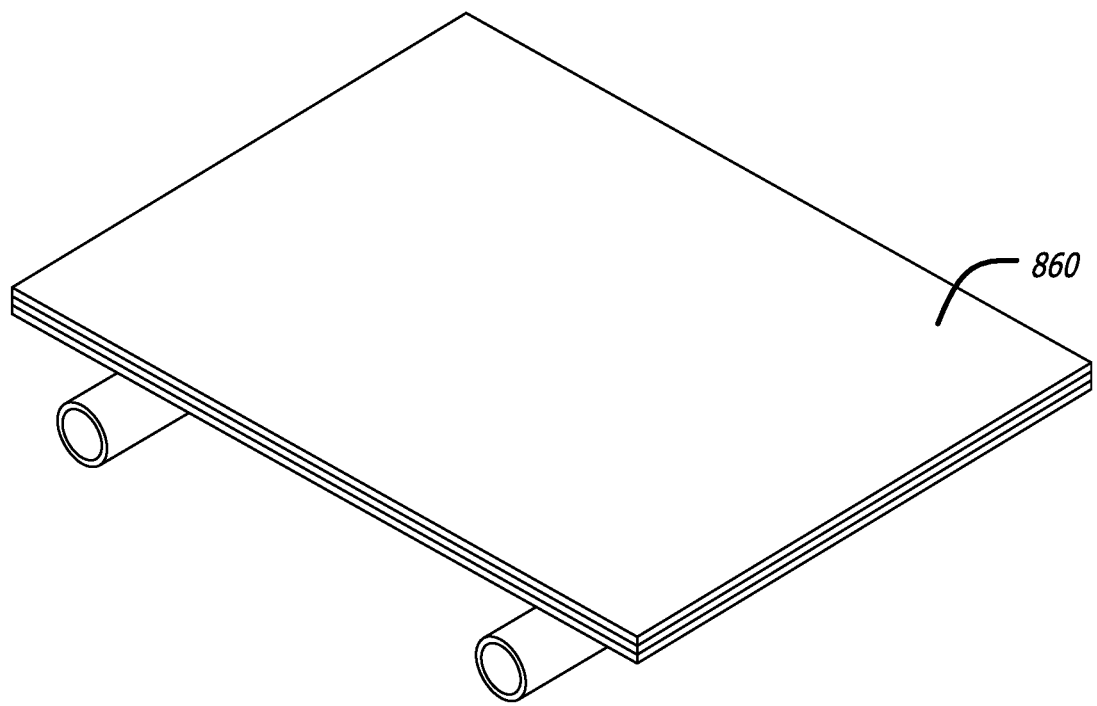
FIG. 23 is a view similar to FIG. 22 with the biocompatible layer in place.

The rest of the module forms a heat exchange stack (HES) shown generally at 500. The stack includes the bottom plates 520 collectively forming a thermally-conductive plate construction or layer shown generally at 530. FIG. 12A shows the plates as transparent so the backside adhesive on the plates can be seen in the channel assembly for illustrative purposes. An alternative plate construction is shown in FIG. 12B where there are plates or plate pieces 540, but no windows. FIG. 15A shows an alternative embodiment having twelve instead of four plates and thereby providing more axes of rotation flexibility, three in the Y direction and two in the X direction. A further alternative is shown in FIG. 15B where the plate pieces 550 are connected together with a web 560.

Figure 14:
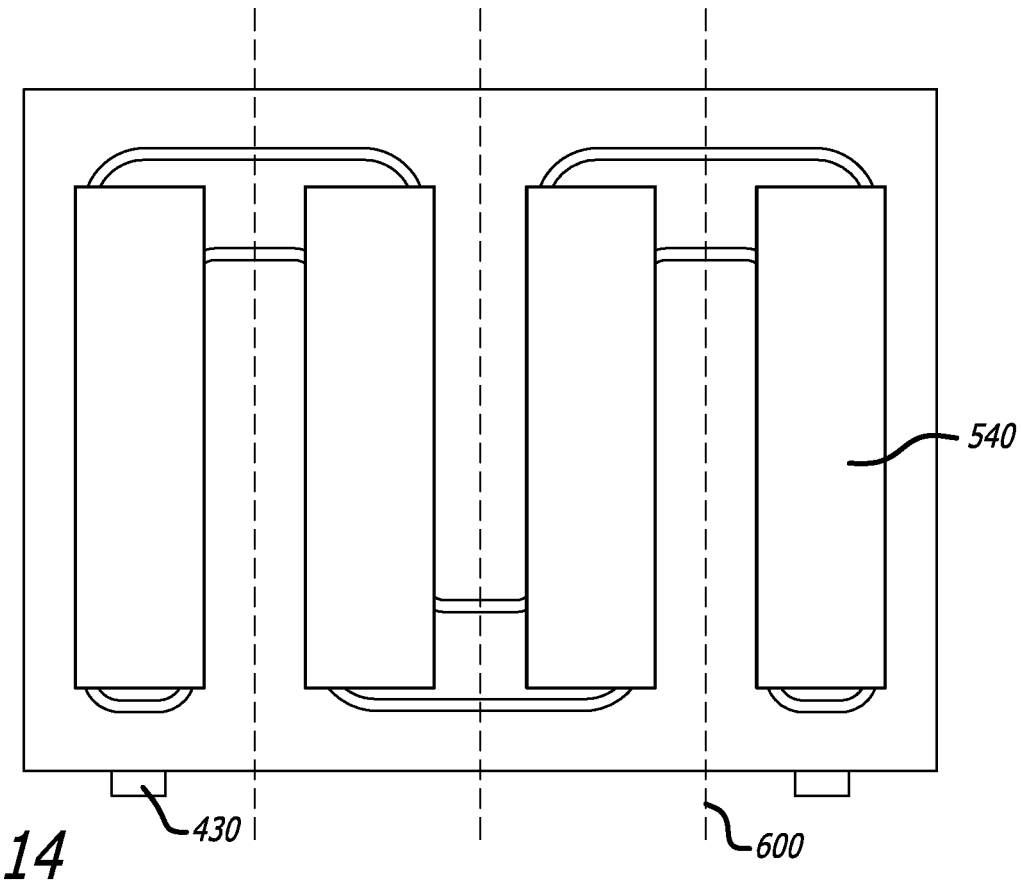
FIG. 14 is a view similar to FIG. 11 showing the axes of rotation flexibility of the channel assembly and thus of the module.

An advantage of the various plate constructions of the present disclosure are that they provide greater flexibility for the device. The flexibility can be provided about Y axes 600 as shown in FIG. 14 for example. Or with the plate configuration of FIG. 15A about X axes 610 and Y axes 620.

Referring back to FIG. 3 additional layers are the lower Mylar sheet 650 with openings and the TEC assembly 670. As shown the TEC assembly can include TEC 680, the previously-mentioned copper squares 690, the copper bus line 700 and wires 710. Thermistors 750 are shown in the figures.

A core composite layer 800 has holes 810 cut in it. The upper Mylar sheet 830 also has holes 840 cut in it for the TECs. The top plate is shown at 850 and the biocompatible layer at 860.

Referring to the cross-sectional views the adhesive for attaching the TEC's to the plate pieces (bottom plate) is shown at 870 and the thermal paste/epoxy for attaching the TECs to the top plate is shown at 880. And the threads or other mechanical connections are shown at 900.

2. Construction and Operation of Control Console and Umbilical 2.1 Control Console Construction The control console can be comprised of the following components:
(a) Enclosure
(b) Quick-disconnect fittings
(c) Power and signal plug
(d) USB port
(e) ¼" Jack
(f) AC Power inlet
(g) Fan(s)
(h) Radiator
(i) Pump
(j) Reservoir
(k) Flow meter
(l) Level sensor
(m) AC to DC power supply
(n) Battery
(o) DC to DC power supplies
(p) H-Bridge
(q) Microcontroller printed circuit board assembly (PCBA)
(r) Screen driver board
(s) Touch screen 2.1.1 Enclosure The enclosure can be manufactured from laser cut acrylic, cast urethane, injection molded plastic or a similar method. It can be made from a single piece or by joining multiple panels that are either snapped together, screwed together, or by other mechanical or adhesive methods including a combination of the methods. The enclosure's main purpose is to house the internal components of the control console as well as mount the input and output ports and connector needed to interface with the umbilical and therefore HEMs. This enclosure can also maintain its rigidity with vents, for heat dissipation. The enclosure also can be constructed to maintain safety in the event of a fluid leak near electrical components.

2.1.2 Input And Output Components

The input and output components can be panel mounted to interface with a plug, cable, or tube. They can be installed by creating a cut-out in the enclosure of the specified component, such that it can be inserted partially through the hole and mechanically fixed, whether through screws or a snap-in feature. The quick disconnect fittings, the power and signal plug, the USB port, the ¼" jack, and power outlet are all installed in this manner. The touch screen is installed in a similar manner but rather than being put through the enclosure, it is mounted such that the profile cut out of the enclosure allows access to the screen without the part extending out.

2.1.3 Internal Components

The internal components are all mounted by screw mounts or affixed to platforms with various mechanical or even adhesive methods. The fan(s) are mounted to the radiator, and the radiator fan system is mounted such that the fans directly come into contact with a vent, and they are screw-mounted into place. The pump, AC to DC power supply, necessary DC to DC power supplies (zero to two depending on the design), H-Bridge, microcontroller PCBA, screen driver board are all screw mounted. The reservoir is held in place by being mounted on a shelf or platform.

2.1.4 Electrical System

The AC to DC power supply and battery provide power to all the components in the system. They are installed such that when the device is plugged into a power source the battery is charging, and when the device is unplugged the device operates on the battery. Depending on the design and component power needs, there are additional DC to DC power supplies that are powered by the power supply or battery. This collection of power supplies and battery are referred to as the power supply system. The power outlet is then wired with 600V rated cable to the power supply system. The power supply system is then distributed to the appropriate components via wiring. The components that require power include the fan(s), the pump, the H-Bridge, the microcontroller PCBA, and in some designs, the screen driver board and touch screen may need individual power. There are additional electrical interconnections separate from the power supply system. Wiring is necessary between the power and signal plug to the H-Bridge and to the microcontroller PCBA. Additional wiring is necessary from the USB port, ¼" jack, flow meter, level sensor, H-Bridge, and screen driver board to the microcontroller PCBA. There is also a wiring connection needed between the touch screen and the screen driver board. All this wiring is completed via screw terminals, soldering, crimping, or plugs, depending on the components specification.

2.1.5 Fluid System

The fluid system within the enclosure is all interconnected with ⅜" or ¼" diameter flexible tubing, such as PVC or polyurethane. They are connected to the individual components using barb or compression fittings. They can be straight or angled, and are screwed into the components. The tubing is connected from the reservoir to the pump inlet and from the pump outlet to the outlet quick disconnect fitting, where the umbilical is attached. The tubing also goes from the inlet quick disconnect fitting to the radiator and from the radiator back into the reservoir. Between the pump outlet and before the outlet quick disconnect fitting, the flow meter is installed with the same barbed fittings. In addition, a second threaded hole is created in the reservoir so that the level sensor can be installed.

2.2 Umbilical Construction

The umbilical is an extended section of a paired tube, such as PVC or polyurethane, as well as an extended piece of wiring assembly between ⅓ of a meter to four meters. There are two tubes for the fluid, again either ⅜" or ¼" in diameter and made from a flexible material, that go from quick disconnect fittings of the control console to the HEM. The appropriate connector, with barbs if necessary, are attached to the ends of these tubes such that it can plug into the quick disconnect fittings and into the HEM. The wire assembly is comprised of two cables capable of carrying current to the HEMs and at least two wires that can bring signals from the HEMs temperature probe. Additional wires are included if there are more than one temperature probe being used in the HEM. The cables and wires are crimped and soldered appropriately in order to be connected to the terminal of the plugs that goes into the control console on one end and into the HEM on the other end. A braided sleeve or other sheathe can then be wrapped around the entire cable and tube assembly.

2.3 System Operation

The touch screen is interfaced by the user and in the simplest case a single temperature below room temperature is set for an indefinite amount of time (it will be possible for the user to set and use or select programmed temperature and time. algorithms). The microcontroller receives the temperature signal from the HEM. It responds by transmitting the appropriate signal to the H-Bridge which then, powered by the power supply system, can produce and send the necessary power to the HEM through the umbilical assembly. This allows the HEM to approach the set temperature. This feedback loop is repeated as necessary to maintain the user's selected temperature. In conjunction, the heat created by the HEM is being removed via the fluid system. Fluid is continuously flowing in a closed loop. The pump is drawing fluid from the reservoir and sending it through the umbilical into the HEM where it collects heat and returns via the umbilical. It then passed through the radiator and returns to the reservoir. When passing through the radiator, the collected heat is dissipated from the air forced through the radiator by the fans. The fans also help to remove excess heat produced from the electrical components in the enclosure.

3. Heat Exchange Module Construction

Discussed below are the components and fabrication process for Heat Exchange Modules (HEM) of this disclosure, which can be adapted and used in a heat exchange system of the present disclosure, for example. Generally, there are two methods of fabrication for the module, whose differences are described in detail later in this disclosure. The fabrication process set forth below is in the order that components appear in first fabrication method.

3.1 Water Circulation

The circulation of water throughout the device is essential in extracting heat from the HEM. The water circulation is done through two sheets of thermoplastic polyurethane (TPU), or other similar material that can be RF welded (or similar process) into channels for water to flow through. TPU material is used because it is thin, flexible, and can be easily manufactured to specification.

3.2 RF Weld

The design of the RF weld is custom to the specifications of each different HEM. Aside from a typical welding design of a typical HEM, and another possible design is shown. Each TPU sheet is a thickness of 15-40 mils (to be decided), and the RF weld line is three mils, for example. TPU inlets/outlets (typically in the form of elbows) are also RF welded at the ends of the designed water channels to allow the inlet and outlet of the water to be circulated. These inlets/outlets vary in size and have an inner diameter (ID) of either ¼" or ⅜" depending on the specifications of each HEM. The system of the two TPU sheets and elbows welded together will hereby be referred to as the "water channels."

3.3 'Windows' in the TPU Sheet

Since the TPU is not thermally conductive, an opening can be created in the water channels to allow for sufficient transfer of heat into the water from the device. The TPU sheet that does not have the elbows RF welded to it is cut in the shape of rectangles to form 'windows' in it. This is typically done via die-cutting, but can be done by other methods. A number of the figures show the water channels with windows cut out. This figure shows only one of the many possible configurations of the windows cut in the TPU sheet. The number of windows can range from one large window to as many windows as there are TECs in the device. The higher number of windows, the more flexible the device can be. This will be further explained below.

3.4 Thermally Conductive Layer ('Bottom Plate')

With an opening now in the water channels, a thermally conductive material must be used to seal the water channels to prevent leaking. This material is typically a thin metal plate, either copper or aluminum of thickness 7-12 mils (to be determined), but can be any semi-flexible thermally conductive substrate. The metal plate is cut into pieces that are relatively larger than the window cutouts in the TPU (usually by ~10 mm). Smaller pieces are preferable over a single large piece of metal to allow for flexibility in the device and to reduce weight. The areas in between the metal plates allow for more flexibility in the device, since the TPU is more flexible than the metal.

Referring to the windows discussion earlier, the number of metal plates can be the same as the number of windows cut out in the water channels. For instance, a small window can be cut around each TEC (twelve windows total), and twelve metal plates, each a bit bigger than the size of the windows, can be used to seal each window. This method allows for more flexibility since it would have flexibility along two axes instead of just one. This is because all of these plates lie within the same plane, and for ease of discussion, they will collectively be referred to as the 'bottom plate'. This plate may also be referred to as the 'hot plate', since during normal cooling operation this plate will heat up, whereas the 'upper plate' (discussed later) will be cold. (The bottom plate can be broadly referred to as a 'cover.')

3.5 Sealing the Water Channels to the Thermally Conductive Layer

The sealing process can use either a structural adhesive (typically either epoxy or acrylic), or a pressure sensitive transfer tape. Examples include: Devcon HP250 (acrylic adhesive), 3M DP8005 (epoxy adhesive), and 3M 9472 (transfer tape). For these adhesives, both the TPU and metal plates can be thoroughly abraded and cleaned to allow for proper bonding. The adhesive or tape is placed on each plate in the areas that overlap the TPU, but not in areas where water will contact the plate. Putting adhesive over the whole plate would both waste material and form an unwanted barrier that heat must transfer through to reach the water.

Figure 7:
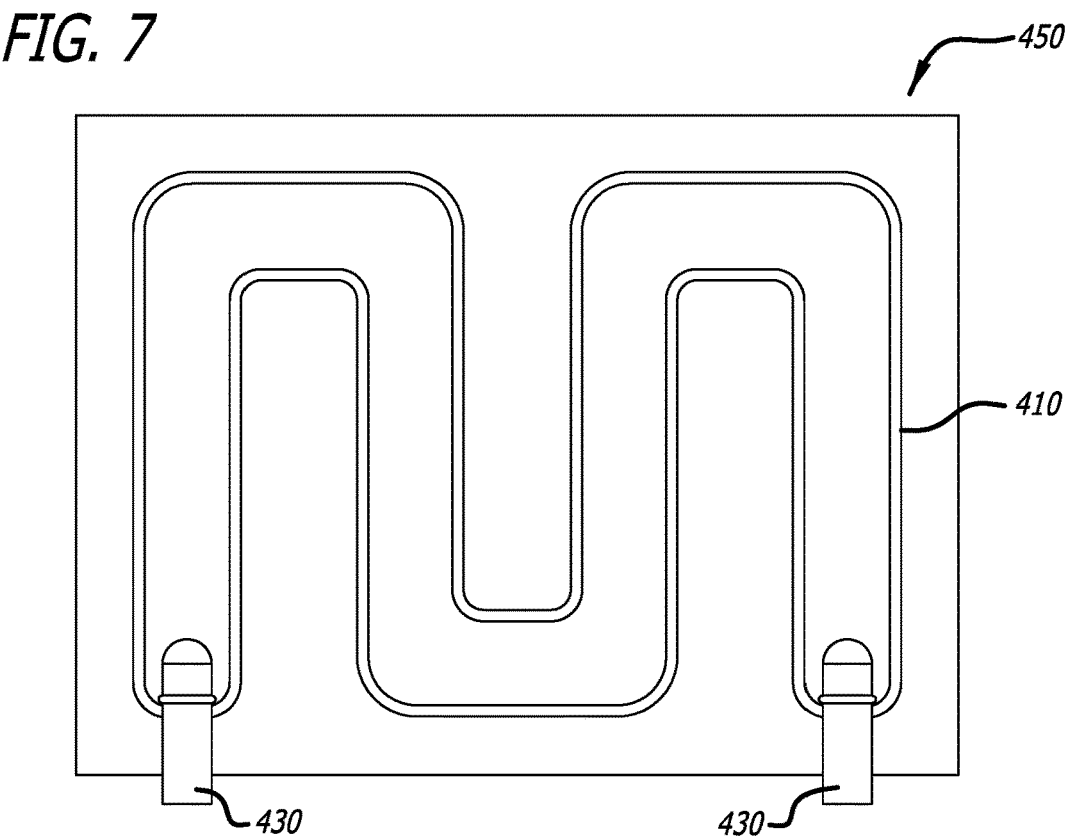
FIG. 7 is a bottom plan view of a channel assembly, such as that of FIG. 5, of a module of the disclosure.
Figure 8:
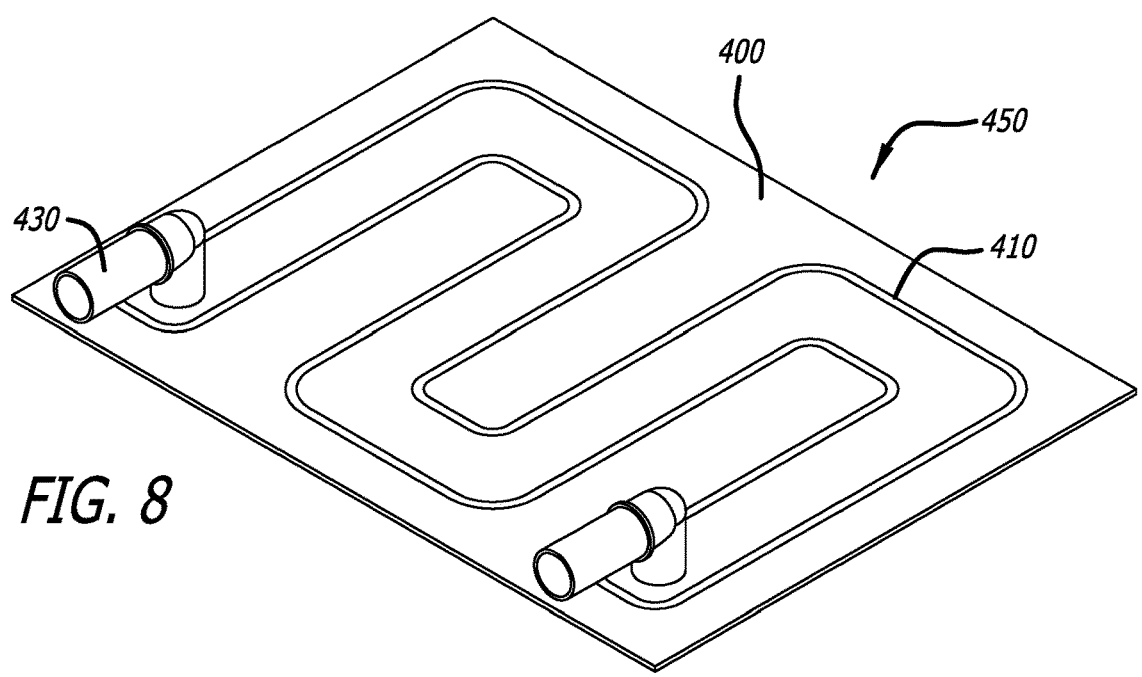
FIG. 8 is a perspective view of the channel assembly of FIG. 7.
Figure 9:
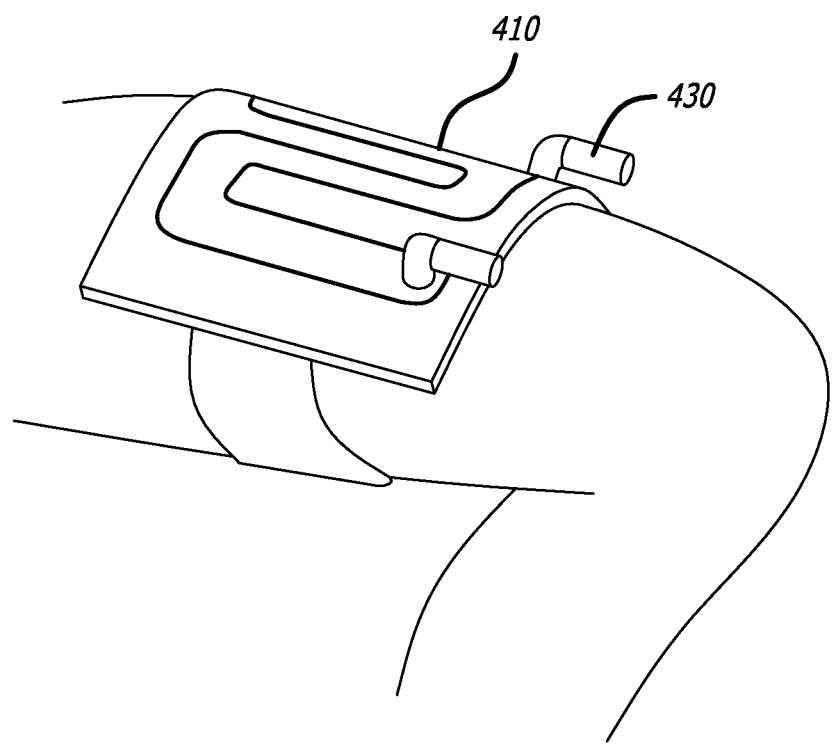
FIG. 9 is a perspective view of the module of FIG. 7 illustrated in a strapped position to a leg of a patient.

FIG. 7 shows adhesive laid onto the plate. The rectangular metal pieces with adhesive are set to the TPU and allowed to cure, thereby sealing the water circulation channels. FIG. 8 shows the plates bonded to the TPU sheet. FIG. 9 shows the metal as transparent to illustrate the windows below. In the Second Method (see below) this sealing process can be completed after the rest of the device has been assembled.

3.6 Heat Transfer Elements (TECs)

Figure 10:
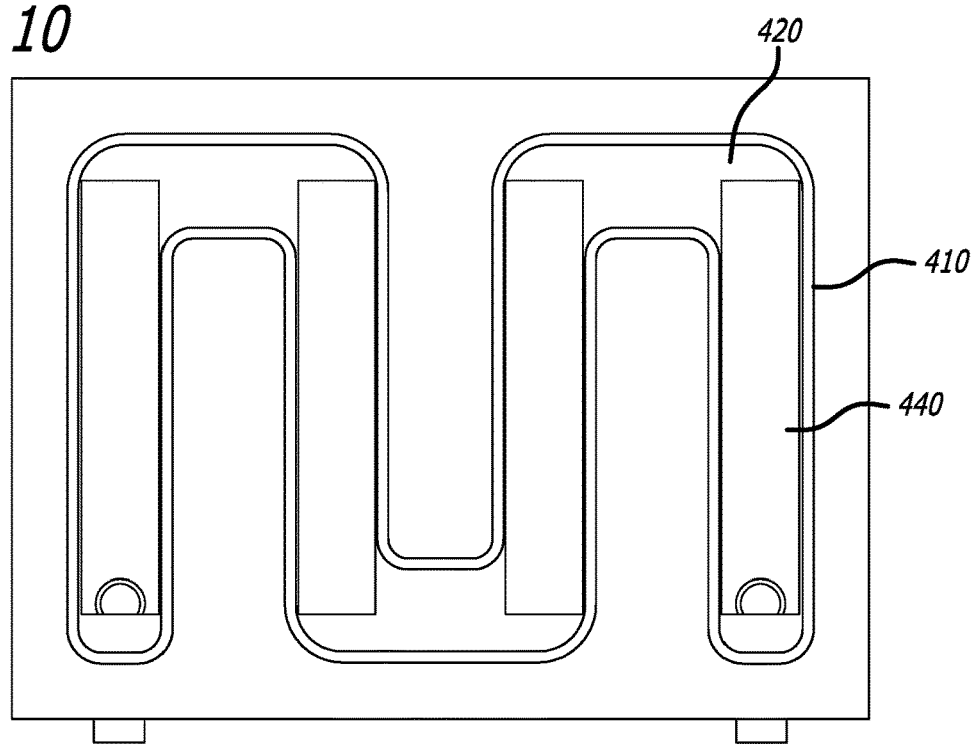
FIG. 10 is a top view of a channel assembly showing the channel windows.
Figure 11:
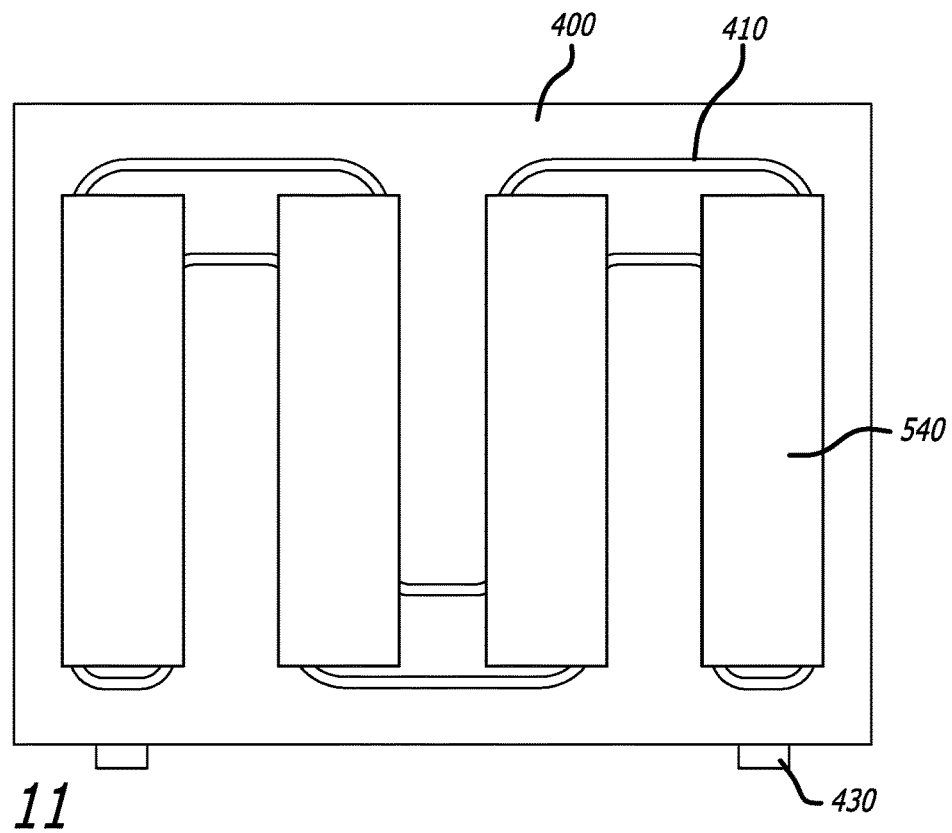
FIG. 11 is a view similar to FIG. 10 showing thermally conductive plates covering the windows.

The next step is to arrange the modules that produce the cooling effect in the device, the thermoelectric coolers (TECs). The TECs operate on electrical power, and are connected to a power source via bus bars. These bus bars are made of copper, thin, flexible, and keep a low profile inside the HEMs. The low profile is helps maintain interstitial space within the HEM between the two sides of the TECs. The bus bars can be highly electrically conductive, which prevents them from heating up. Any heat generated through resistance losses in the wiring would inherently cause the HEM to be less efficient. The wiring on each TEC is trimmed down to about 25¼". Copper bus bars are cut to the corresponding lengths between TECs, and the TEC wires are soldered to the bus bars. If the HEM has multiple banks, the bus bars are soldered together at junctions. Each TEC is cleaned thoroughly with acetone upon completion of soldering. This completes the 'TEC chain.' To prevent shorting the circuit, insulating tape can be placed on the bottom plate in any area the bus bar may come in contact with the plate. FIGS. 10-11 illustrate the TEC assembly.

FIG. 12B is a view similar to FIG. 12A showing the backside of the channel assembly but of an alternative embodiment in which the windows are not cut out, keeping the water channel layer intact.

FIG. 15B is a view similar to FIG. 15A but of another alternative embodiment connecting the twelve plates with another cover represented here by a hashed pattern. This cover can be a meshed material, a material with perforations along the axes of flexibility, such as a perforated foil, or a cover with varying thickness, such as a foil that is thinner along the axes of flexibility, all of which would connect the plates and still provide the axes of rotation for flexibility. It is also possible to do this with four plates or any other number of plates necessary to meet the design requirements.

3.7 Body-Facing Interface Layer ('Top Plate')

This layer can be a thermally-conductive metal plate (but can be any semi-flexible thermally conductive substrate) that will be placed on the opposite side of the TECs, and can be referred to as the 'upper plate' or 'cold plate'. A thermistor is added to this plate to measure the temperature of the surface that is in contact with the skin. To do this, the thermistor is placed in a suitable location (typically the middle of the plate) and the insulated lead wires are taped to the plate using thermally resistant tape. A thermally conductive adhesive (typically Dow Corning 3-6750) can be then placed around the thermistor, just enough to cover it completely. The adhesive can be cured to set the thermistor in place.

3.8 Insulation in the Interstitial Space ('Core Composite')

The interstitial space is defined as the area between the top and bottom metal plates that is not taken up by the TECs or other elements (thermistor, bus lines, etc.). A material called a 'core composite' can be used, and examples are Koroyd or Amarid Honeycomb. These are structured materials often shaped as a honeycomb with empty cells. See FIG. 12A. The core composite can be used instead of, for example, a silicone foam. The core composite is cut in the areas where the TECs are present to fill all but those areas between the two metal plates (interstitial space). The material is a good thermal insulator because there is air in every core cell, minimizing the amount of heat transfer through the material in contact with both plates. The core composite also maintains its structure over time, keeping the separation of the top and bottom plates, for thermal insulation. The core composite advantageously does not condense or compress over time, which would allow the plates to merge closer to each other. The core composite also maintains the structure of the HEM during the mechanical fastening process, preventing the plates from compressing into each other.

In addition, a sheet of Mylar or similar reflective material can be placed on the either side of the core composite for further insulation. These sheets prevent heat from radiating between the two plates by reflecting any emitted radiation back to the plate from which it originates.

3.9 Device Assembly

The assembly of the device can use a thermally conductive epoxy to adhere the TECs between the two metal plates, or preferably a thermal paste (typically Arctic MX-4 Compound) that allows for some give between the TECs and the plates on either side of them. With a thermal paste used (instead of an epoxy, for example) a method is needed to hold the device together (basically creating a sandwich that holds the TECs in contact with the metal plates). The TECs maintain intimate contact with the metal plates, so that that there is sufficient heat transfer between the materials.

This method can be mechanical fastening, such as sewing, use of rivets, or a similar procedure that will hold the device together structurally. This discussion will use sewing as the primary method, although others are just as viable. Two methods of mechanical fastening are described in the following two subsections.

3.9.1 First Method

This layer assumes that all of the aforementioned procedures have been carried out, and that the bottom plate is attached and sealed to the water channels at this point. The TEC chain that was produced earlier is now used. A thin layer or bead of thermally conductive paste is placed onto the "top" surface (the surface to be in contact with the top plate) of each TEC. The chain of TECs is then placed on the top plate. The first sheet of Mylar is then placed over the top plate around the TECs. The core composite is then placed over the Mylar sheet and around the TECs. The second Mylar sheet is then placed over the core composite and around the TECs. A thin layer or bead of thermally conductive paste is placed onto the 'bottom' surface (surface to be in contact with the bottom plate) of each TEC. The bottom plate is then placed on the TECs. Recall that the bottom plate is already sealed to the water channels. At this point, the entire device is mated, and it just needs to be mechanically fastened.

Figure 13:
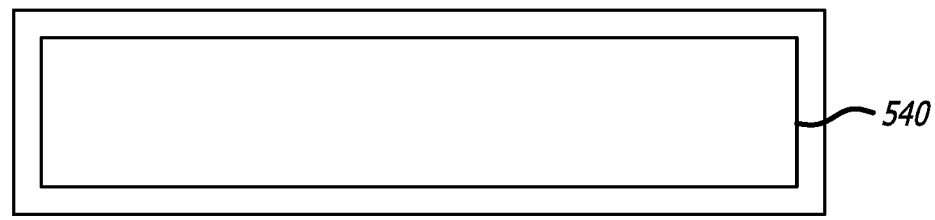
FIG. 13 is an enlarged plan backside view of one of the plates of FIG. 12A depicting the adhesive around the perimeter of the plate.
Figure 25:
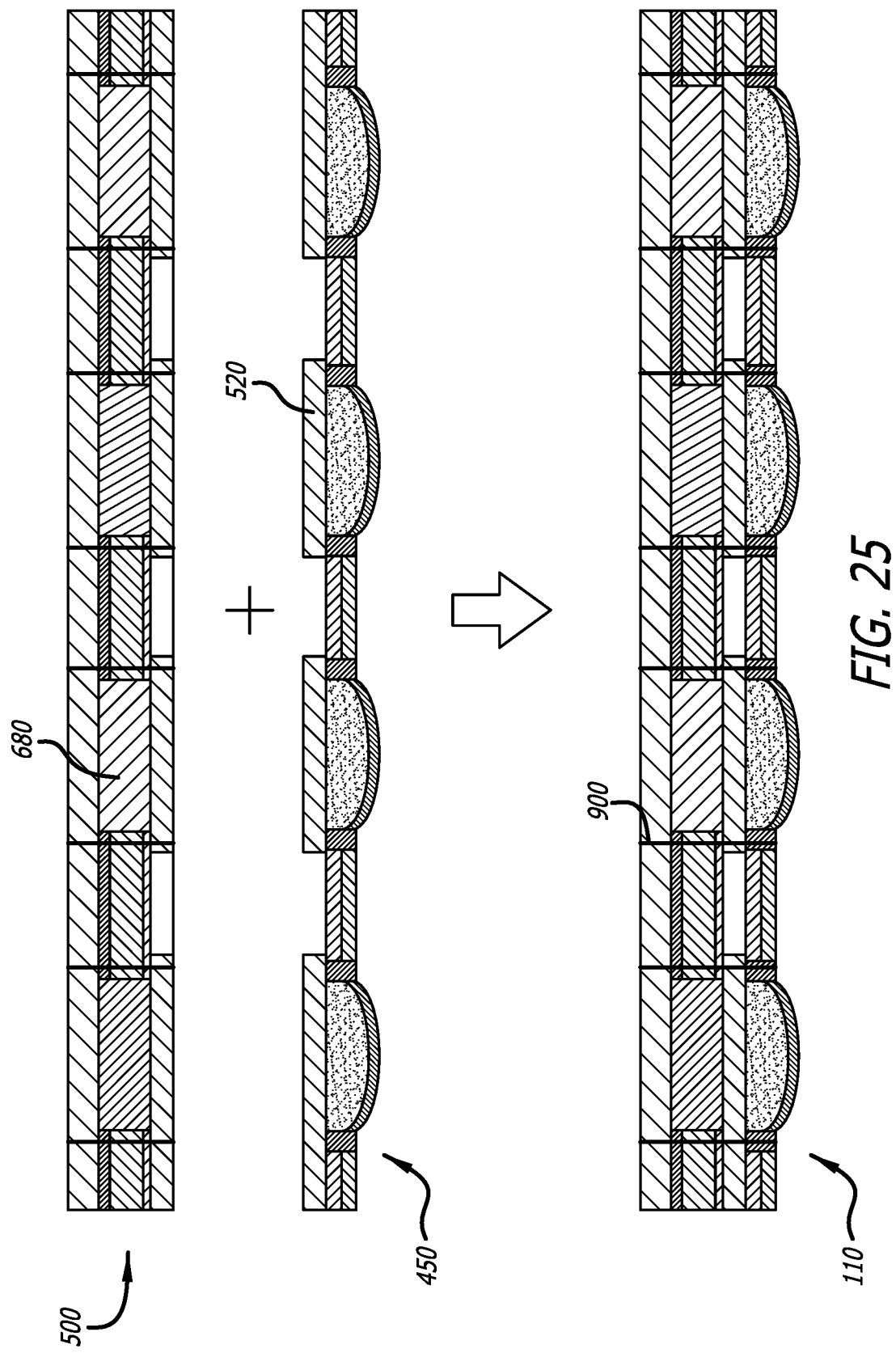
FIG. 25 is a view similar to FIG. 24 showing an alternative second method of mechanically securing the heat exchange stack together with the mechanical securement extending through the channel assembly.
Figure 26:
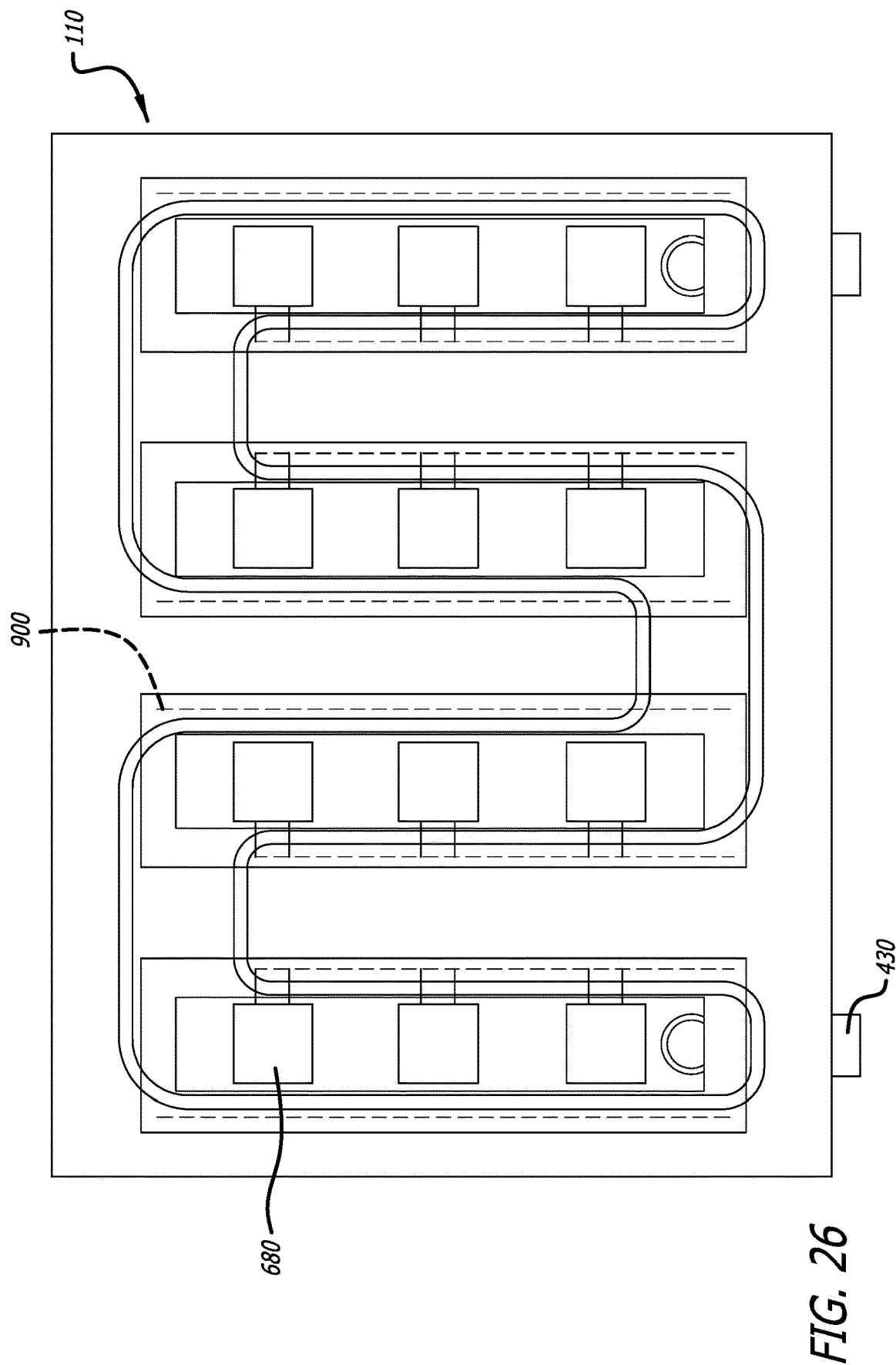
FIG. 26 is a top plan view similar to FIG. 16 but showing the areas of mechanical securement of the method of FIG. 24.
Figure 27:
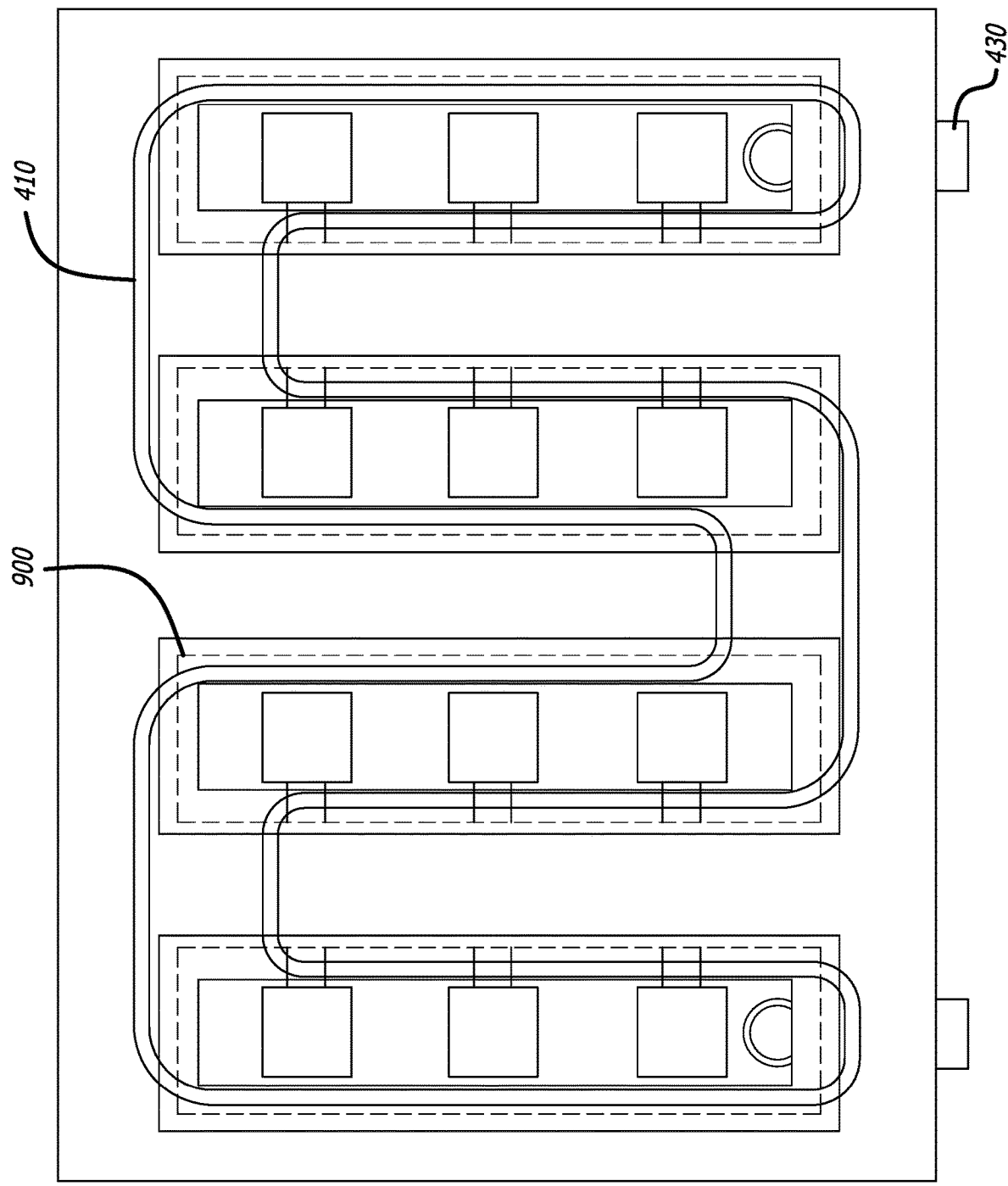
FIG. 27 is a top plan view similar to FIG. 16 but showing the areas of securement of the method of FIG. 25.

All of the components are held in place with c-clamps or similar jig, and the entire device is passed through a sewing machine. The thread therefore penetrates through the entire device. (See bottom half of FIG. 25.) It is important to note that the thread can only be in certain locations. It should not pass through in any location where the water is flowing, or else it was pierce the water channel and cause a leak. It also passes through both bottom and top plates to hold them both together. This leaves the same area that the adhesive was placed on the bottom plate to seal it to the TPU for stitching. (See FIG. 13 for a cross-sectional view of the First Method.)

3.9.2 Second Method

Figure 24:
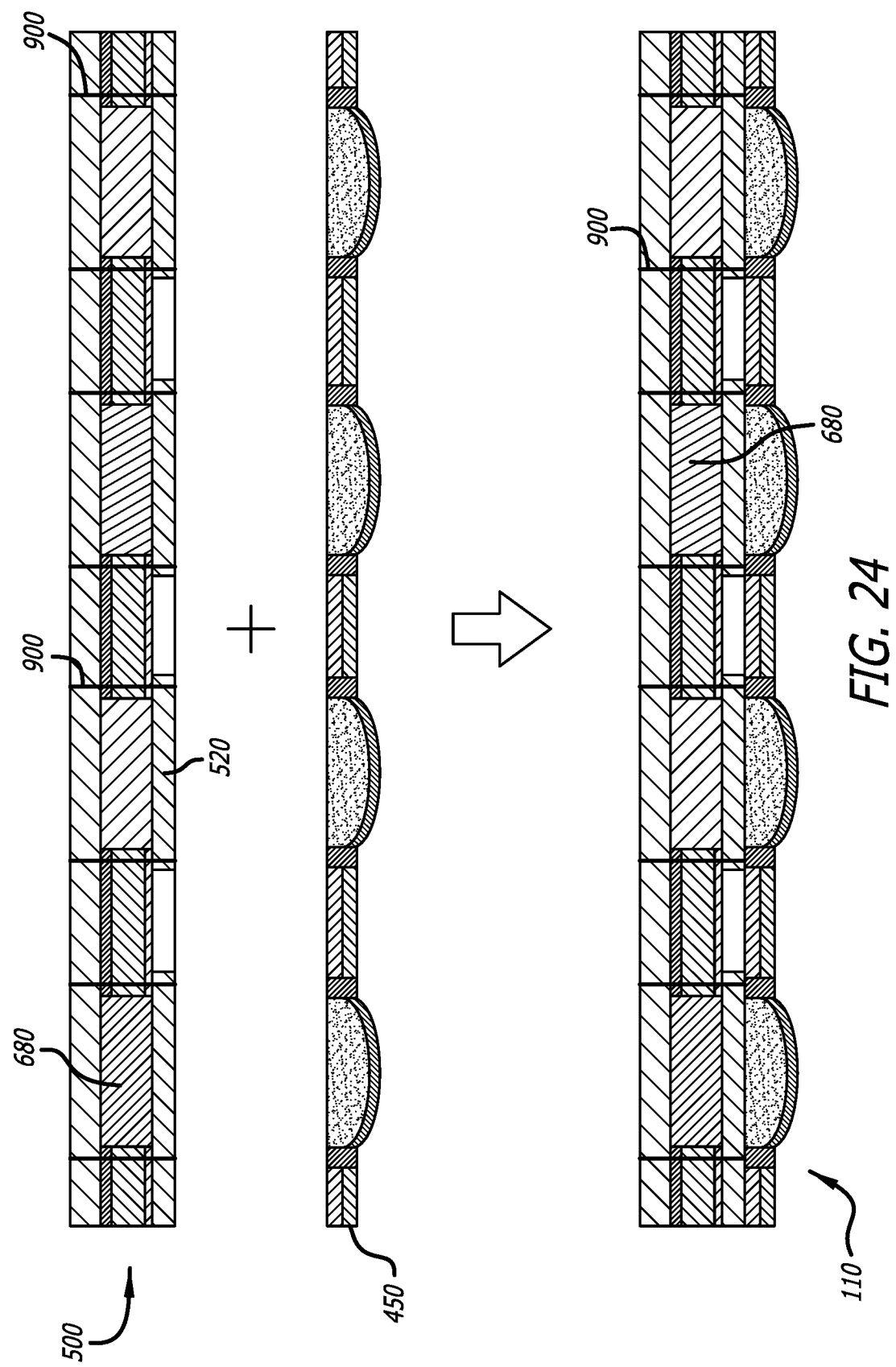
FIG. 24 is a stylized cross-sectional view through a module of the disclosure showing a first method of mechanically securing the heat exchange stack together with the mechanical securement not extending through the channel assembly.

The main difference between the two methods is how many components the thread (or fastener) will pass through. In the second method, the device is fabricated in a different order, in which the sewing is not the last step, and therefore the thread does not have to pass through the entire device. (See FIG. 24.) In this method, what can be referred to as the 'heat exchange stack' or HES will be made first. Making the HES follows the same procedure as the First Method, the only difference being that the bottom plate is not yet adhered to the water channels. Taking the procedure above for clarity:

The TEC chain can be as follows. A thin layer or bead of thermally conductive paste is placed onto the 'top' surface (surface to be in contact with the top plate) of each TEC. The chain of TECs is then placed on the top plate. The first sheet of Mylar is then placed over the top plate around the TECs.

The core composite is then placed over the Mylar sheet and around the TECs. The second Mylar sheet is then placed over the core composite and around the TECs. A thin layer or bead of thermally conductive paste is placed onto the 'bottom' surface (surface to be in contact with the bottom plate) of each TEC. The bottom plate is then placed on the TECs.

The bottom plate in this method can simply be a piece of metal, with the water channels not yet adhered. Each metal plate can be sewn individually to the HES similarly to First Method. After each bottom plate is sewn to the top plate, the HES is completed.

The remaining step is to adhere the water channels to the bottom plate. The water channels with windows are made the same as described earlier, and they are adhered to the bottom plate in the same way, the only difference is that the bottom plate is already attached the HES on the other side. See FIG. 14 for a cross-sectional view of the Second Method.

3.10 Biocompatible Layer

A final step in completing the cooler is adding a thin layer (0.2 to 1 mm) of thermally-conductive biocompatible material to the top plate. This material acts a buffer between the body tissue and the top plate so that the skin is not in direct contact with metal. Biocompatible materials include silicones for medical use, of which a variety are currently available. Alternatively, biocompatible skin adhesives, such as 3M 2476P, are also applicable. FIG. 15A shows the completed device and FIG. 16 shows an exploded view of each layer.

4. Fabrication Procedure

As described above, there are two methods of fabrication. This section gives a succinct step-by-step procedure of both of these methods of the disclosure.

4.1 First Method (a) A TPU sheet is die-cut to form windows in the material
(b) Inlet/outlet elbows are RF welded to a second TPU sheet
(c) These two sheets are RF welded together in a specified shape to form water circulation channels
(d) Bottom plates are cut to specification; the number of plates is equal to number of windows in TPU
(e) Adhesive is applied to the perimeter of the bottom plates and they are adhered to the TPU to seal the water channels
(f) TEC assembly is formed by soldering TECs together using copper bus lines
(g) Top plate, core composite and mylar materials are cut to specification
(h) Thermal paste is applied to upper side of TECs
(i) TECs placed against upper plate
(j) (Top) Mylar sheet added against upper plate, surrounding TECs
(k) Core composite added against Mylar sheet, surrounding TECs
(l) Second (bottom) Mylar sheet added against core composite material, surrounding TECs
(m) Thermal Paste is placed on bottom side of TECs
(n) TECs, along with upper plate materials in interstitial space, are placed against the bottom plate which already has the water channels adhered to it
(o) The HEM is mechanically fastened using sewing, the thread penetrating through the entire device 4.2 Second Method (a) TEC assembly is formed by soldering TECs together using copper bus lines
(b) Top plate, core composite, and Mylar materials are cut to specification
(c) Bottom plates are cut to specification; the number of plates is equal to number of windows
(d) Thermal Paste is placed on upper side of TECs
(e) TECs placed against upper plate
(f) (Top) Mylar sheet added against upper plate, surrounding TECs
(g) Core composite added against Mylar sheet, surrounding TECs
(h) Second (bottom) Mylar sheet added against core composite material, surrounding TECs
(i) Thermal Paste is placed on bottom side of TECs
(j) TECs, along with upper plate materials in interstitial space, are placed against the bottom plate
(k) The HEM is mechanically fastened using sewing, the thread penetrating only through the HES assembly
(l) First TPU sheet is die-cut to form windows
(m) Inlet/outlet elbows are RF welded to second TPU sheet
(n) These two sheets are RF welded together in a specified shape to form the water channels
(o) Adhesive is applied to the perimeter of the bottom plates, which is already sewn to the rest of the HES, and they are adhered to the TPU to seal the water channels.

5. Additional Embodiments

Figure 32:
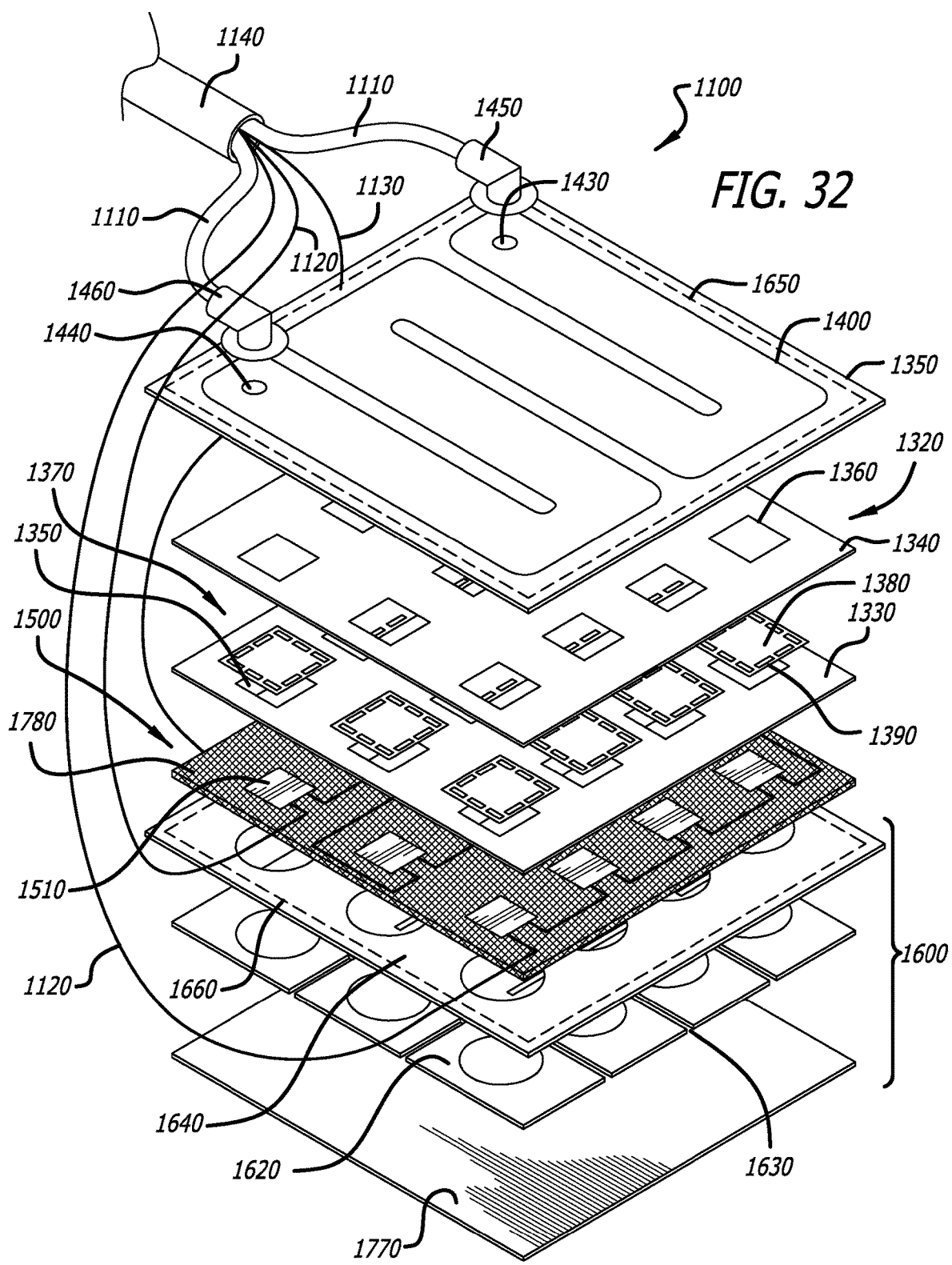
FIG. 32 is an exploded perspective view of a heat exchange module of the present disclosure.
Figure 42:
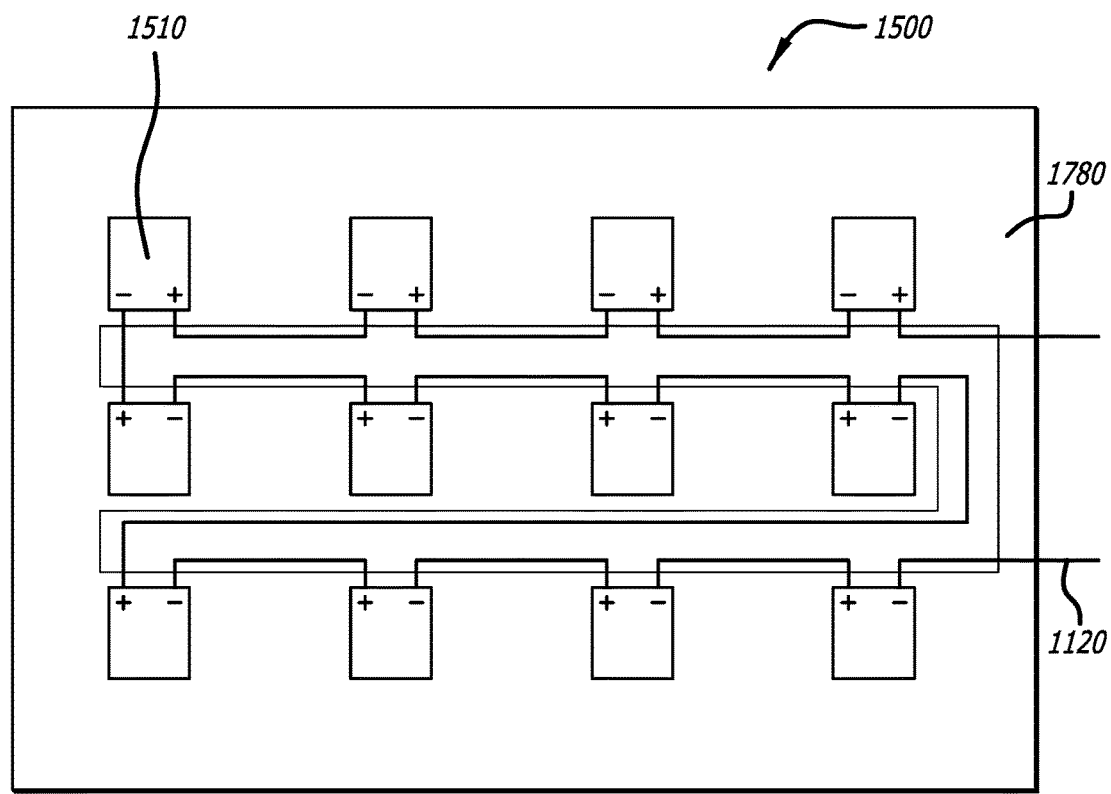
FIG. 42 is a top plan view of an exemplary TEC assembly of the module wherein the TECs are in a single bank and connected in series.
Figure 43:
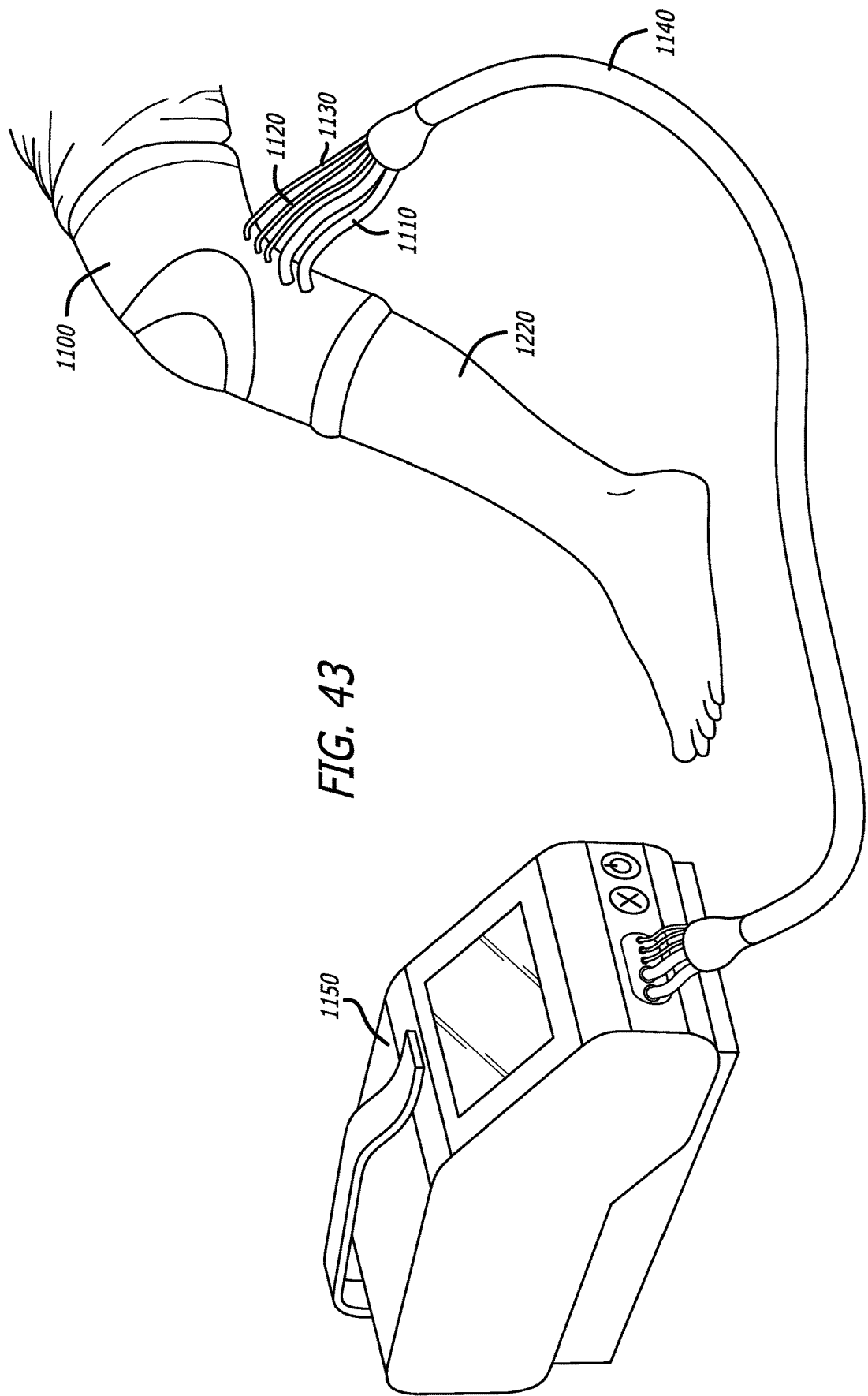
FIG. 43 is a perspective view showing a module of the disclosure in position on a body part of a user and operatively connected to a control and power unit of the disclosure.

Referring to FIG. 32, another heat exchange module of the present disclosure is illustrated in exploded view generally at 1100. The fluid hoses 1110, thermoelectric cooler (TEC) wires 1120, and thermistor (or thermocouple) wires 1130 can pass through an umbilical 1140 to the console 1150 (FIGS. 42 and 28 and 29). (For further explanation of the console, see also FIGS. 28 and 29.) The HEM system of the present disclosure shown generally at 1200 thus includes HEM 1100, umbilical 1140 and console 1150. FIG. 43 shows system 1200 with the HEM 1100 in position, wrapped around a body part 1220 of a patient. The HEM 1100 can be adapted and used on generally any body part 1220 including, for example, the head. As can be appreciated, the HEM 1100 for many applications should be constructed to be able to flex in all three directions to be fitted by the medical personnel against any body part no matter how rounded, angular, large and small.

Figure 45:
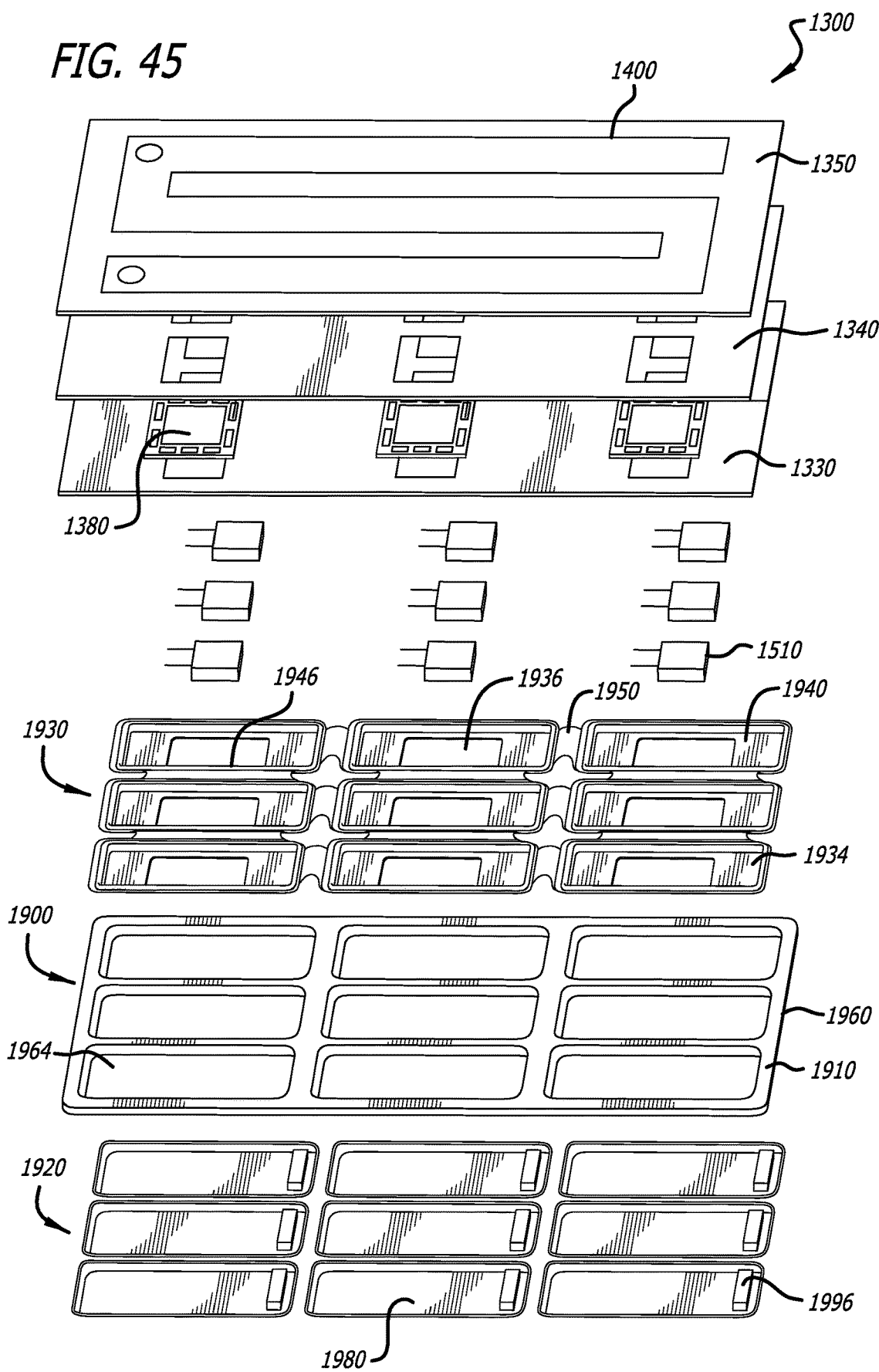
FIG. 45 is a simplified exploded perspective view of a module of the present disclosure having an alternative heat transfer cover assembly.

The HEM 1100 and the alternative embodiment HEM shown generally at 1300 in exploded view in FIG. 45 include many novel constructions to provide for increased flexibility. Although pictured as being flat when in its natural state, the HEM 1100 (or 1300) of the present disclosure also includes cylindrical and cup configurations, and any combination of shapes afforded to follow the contours of various body parts. The HEMs disclosed herein also have novel constructions providing for improved transmission of heat to and from the circulating liquid in the channels and the body parts.

The channel enclosure assembly 1320 of the HEM 1100 can include first, second and third TPU (or other thermoplastic) sheets 1330, 1340, 1350. The first and second sheets 1330 and 1340 include a plurality of holes 1350, 1360, which mate with one another when the sheets are attached together. A plate assembly shown generally at 1370 is positioned between sheets 1330, 1340. It can comprise a plurality of plate pieces shown at 1380. There is one plate piece 1380 for each of the mating holes 1350, 1360. For example, the holes 1350, 1360 and plate pieces can be arranged in a three-by-four array. But then the number and arrangement will be selected as desired for the HEM factoring in the requirements of the TEC assembly and its TECs. As an example, the HEM 1300 is illustrated as having a three-by-three array.

The first and second sheets 1330, 1340 are thermally sealed together with each of the plate pieces 1380 embedded in the two sheets and covering both of the respective mating holes 1350, 1360. See FIG. 38, for example. The plate pieces 1380 can have one or more slots, openings or notches 1390 along their perimeters. This aids in the plate pieces 1380 being embedded into the (plastic) of the first and second sheets, as can be seen by embedded plastic pieces 1400 in FIGS. 36, 38 and 39.

Figure 33:
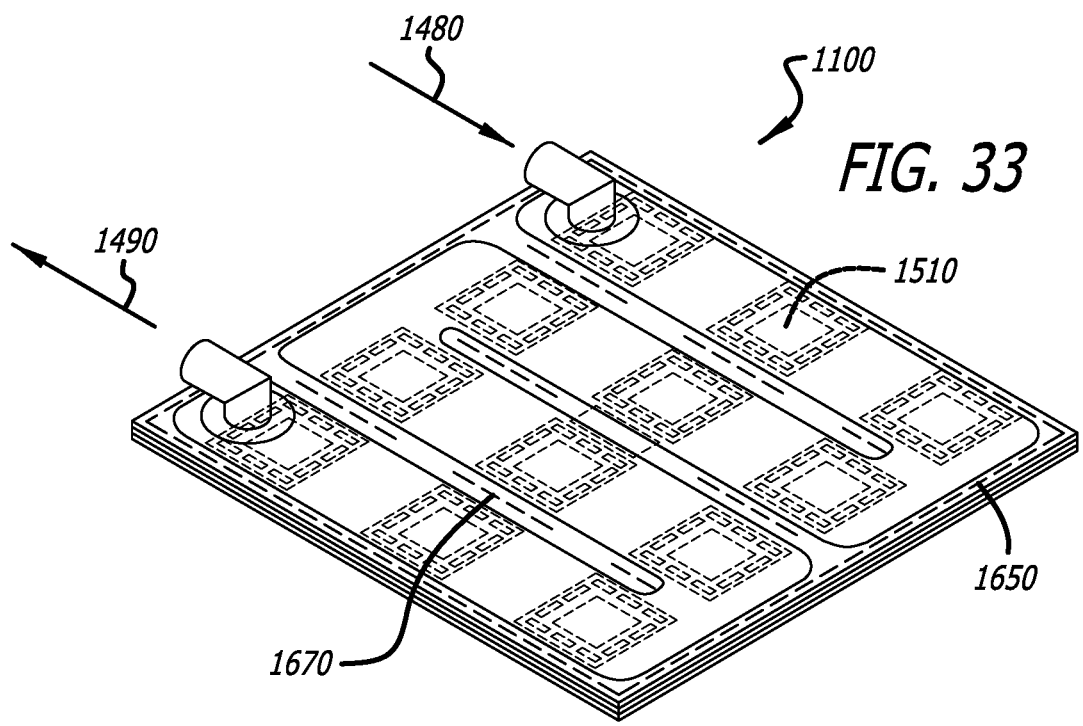
FIG. 33 is a top perspective view of the assembled module of FIG. 32 showing the movement of water into and out of the channel of the module.
Figure 34:
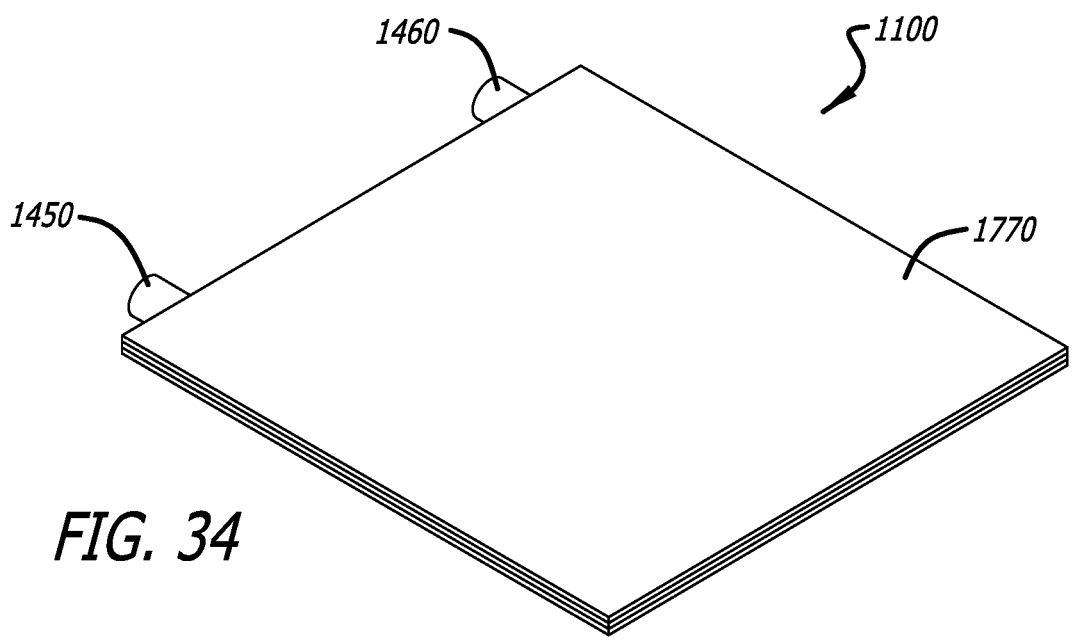
FIG. 34 is a bottom perspective view of the module of FIG. 33.
Figure 35:
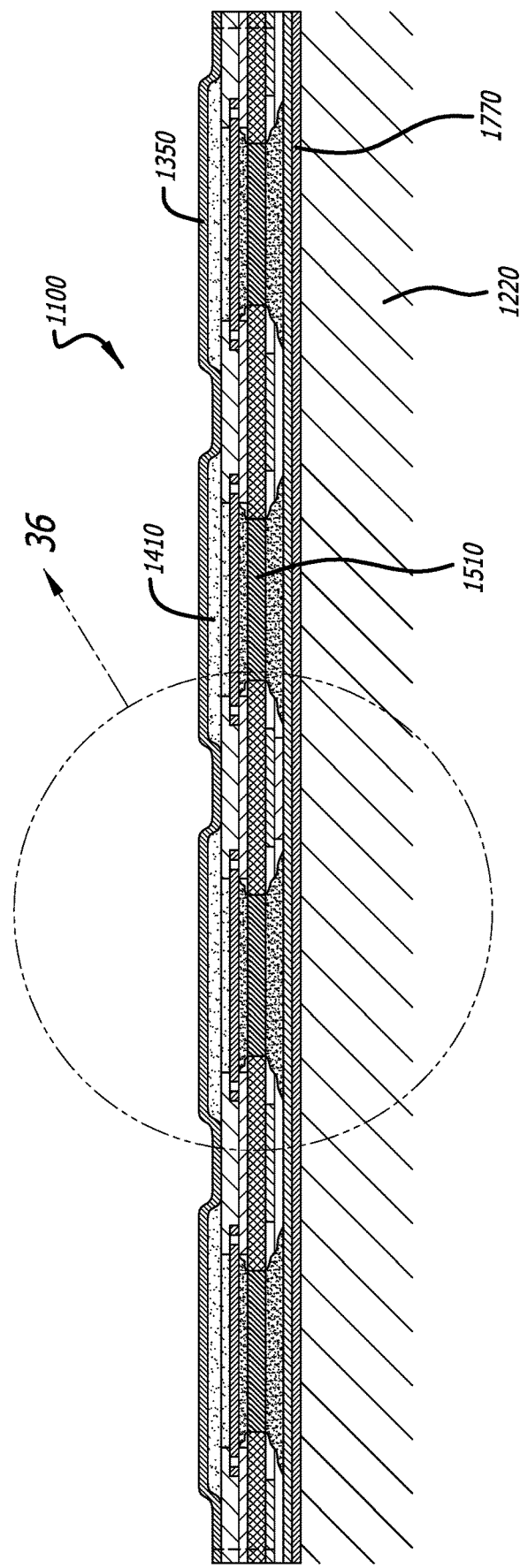
FIG. 35 is an enlarged cross-sectional view of the module of FIG. 33 against a body part of a patient.

With the first and second sheets 1330, 1340 secured together, for example by thermal compression or ultrasonic welding, and the plate pieces 1380 embedded in the sheets at the holes (or windows), the third sheet 1350 is secured thereto. It can be secured by thermal compression, ultrasonic welding, RF welding or similar means. The welding, etc. is configured to form the perimeter 1400 of a water (or other thermally-conductive liquid) channel 1410 between the second and third sheets 1340, 1350. Holes 1430, 1440 (FIG. 32) can be formed in the third sheet at opposite ends of the channel 1410. And angled connectors 1450, 1460 attached to the third sheet 1350 at the respective holes and through which water delivered through tubing 1470 is delivered (arrows 1480, 1490 in FIG. 33) between the console 1150 and the channel 1410.

The design of the RF weld can be customized to the specifications of each different HEM. As an example each thermoplastic sheet, either urethane (TPU), or vinyl or other thermoplastic sheets, can have a thickness of 15-40 mils, and the RF weld line can be three mils. The TPU inlets/outlets 1450, 1460 (typically in the form of elbows) are also RF welded at the ends of the designed water channel to allow the inlet and outlet of the water to be circulated. These inlets/outlets vary in size and can have an inner diameter (ID) of either ¼" or ⅜", for example, depending on the specifications of each HEM.

The third flexible sheet 1350 can be a reinforced TPU sheet or multi-layer with an internal cloth layer, strong enough to withstand pressures of the water in the channel of fifteen to twenty-five psi. As an example, the pressure in the channel should be kept at less than twenty-five psi so as to not cause the sheet 1450 to rupture. Exemplary flow rates in the channel 1410 are two liters per minute, and can range from 0.5 to 3.5 liters per minute.

Figure 38:
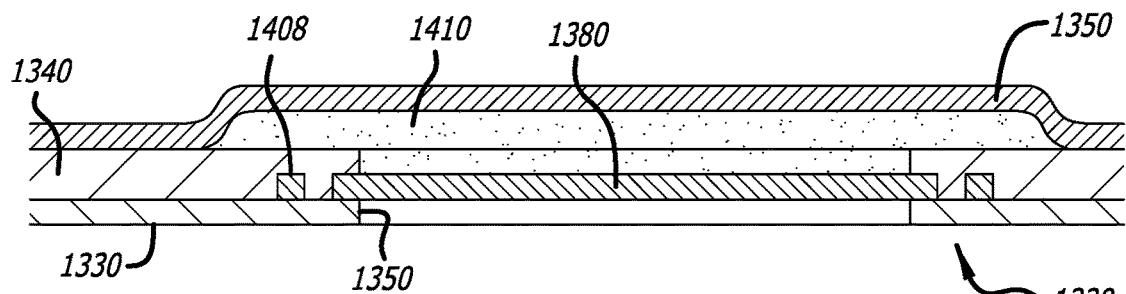
FIG. 38 is a cross-sectional view through the water channel enclosure of FIG. 37.
Figure 39:
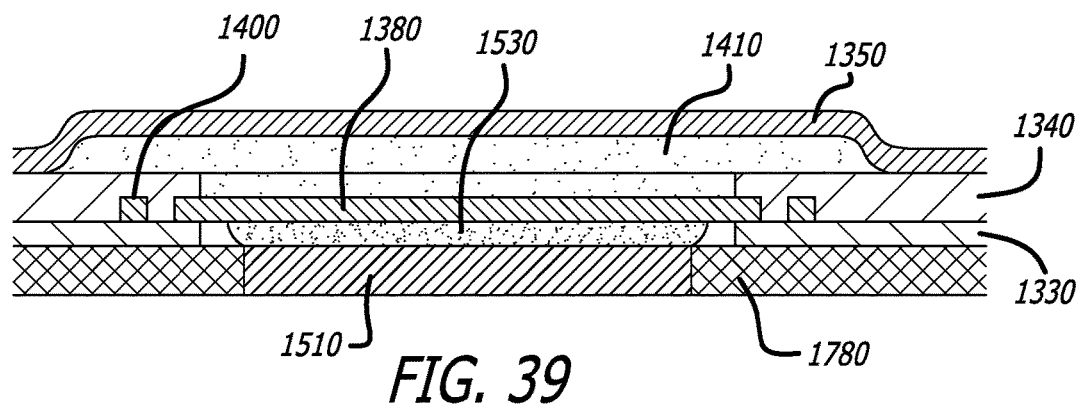
FIG. 39 is a cross-sectional view, similar to that of FIG. 38 but with a TEC layer attached thereto.

Holes 1360 in the second sheet 1340 are positioned so as to be at the channel 1410, as can be seen in FIGS. 38 and 39. Thereby each of the plate pieces 1380 forms a portion of the wall of the channel 1410. Further, each plate piece 1380 is in direct contact with the water flowing through the channel 1410 for direct thermal transfer therebetween.

An alternative configuration omits the plate assembly (plate pieces 1380) and positions the reference (ceramic) face of the TEC directly in/to the hole 1350 of the second sheet 1340, and thereby in direct physical contact with the water in the channel for thermal transfer therebetween.

A further alternative does not include a first sheet 1330. Rather, the plate piece 1380 is secured directly to an inward face of the second sheet 1340 and over the hole. It can be secured, for example, using an adhesive.

It is within the scope of the present disclosure for the plate assembly 1370 to comprise a single large plate; however, by providing a plurality of smaller plate pieces 1380 spaced from one another in both x and y directions, as described above, additional flexibility/bending of the HEM is possible. This flexibility/bending can be along one or more x axes between the plate pieces 1380 and/or along one or more y axes between the plate pieces. Alternatively but less preferably, the plate pieces 380 can be interconnected with a flexible webbing.

A TEC assembly 1500 of the HEM 1100 can be seen in FIGS. 32 and 42 comprising a plurality of TECs 1510. They can be formed in a single bank as illustrated in FIG. 42 and connected in series, or in a plurality of banks (e.g., three or four), each connected in series or in parallel. The number of banks can depend on the type of TECs used, and the voltage ranges optimally controlled by the console unit.

Figure 36:
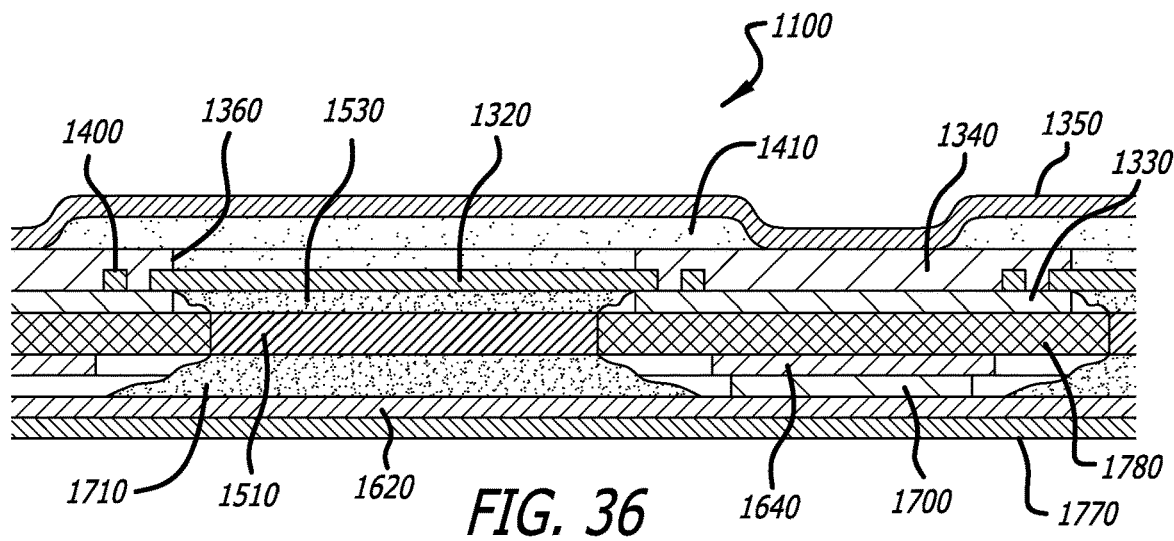
FIG. 36 is an enlarged view taken on circle 36 of FIG. 35.
Figure 37:
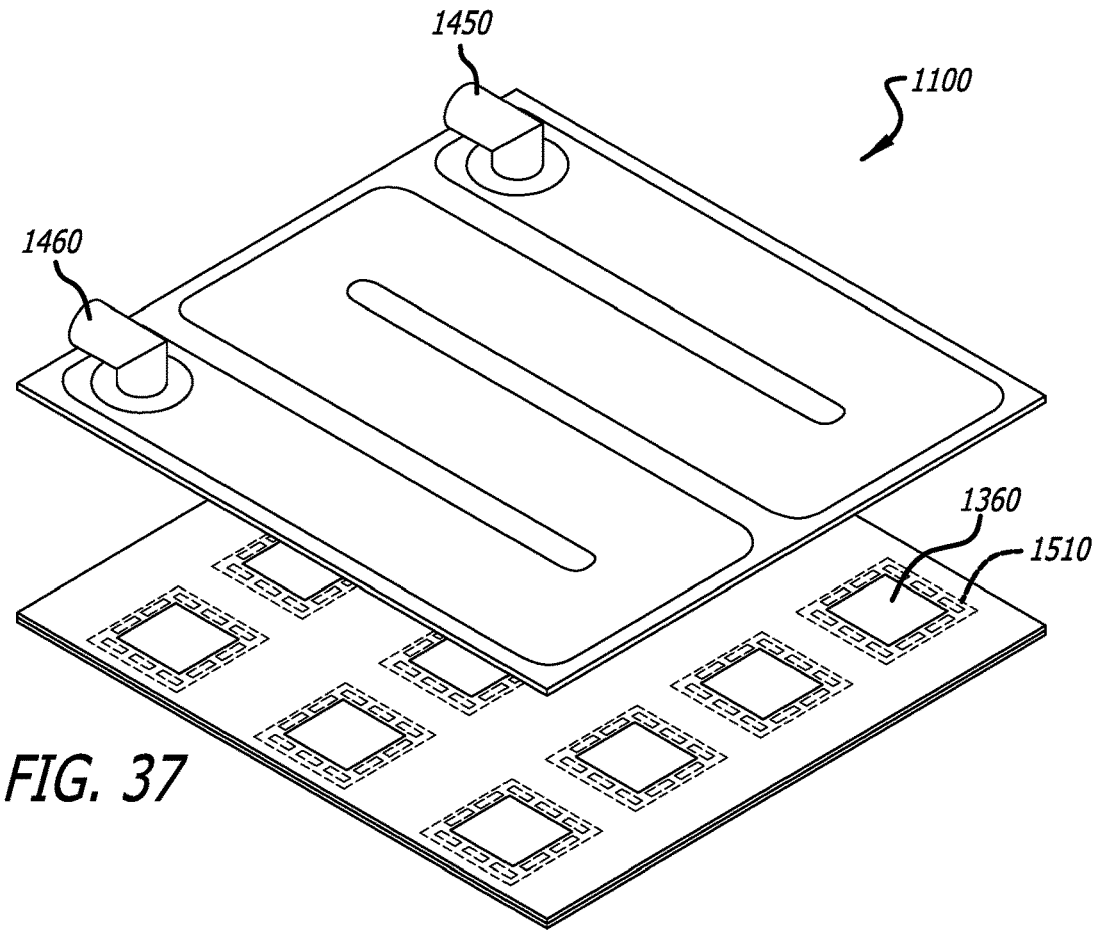
FIG. 37 is a top perspective view of the module of FIG. 33 showing the water channel enclosure in exploded relation.

Reference faces of each of the TECs 1510 are attached to a respective plate piece 1380 in a manner to provide effective heat transmission, as shown in FIGS. 36 and 39 for example. For example, a thin layer of thermally-conductive adhesive, paste or putty 1530 can be used. The TEC assembly 1500 can be operatively connected to the console 1150 by wires 1120.

Figure 40:
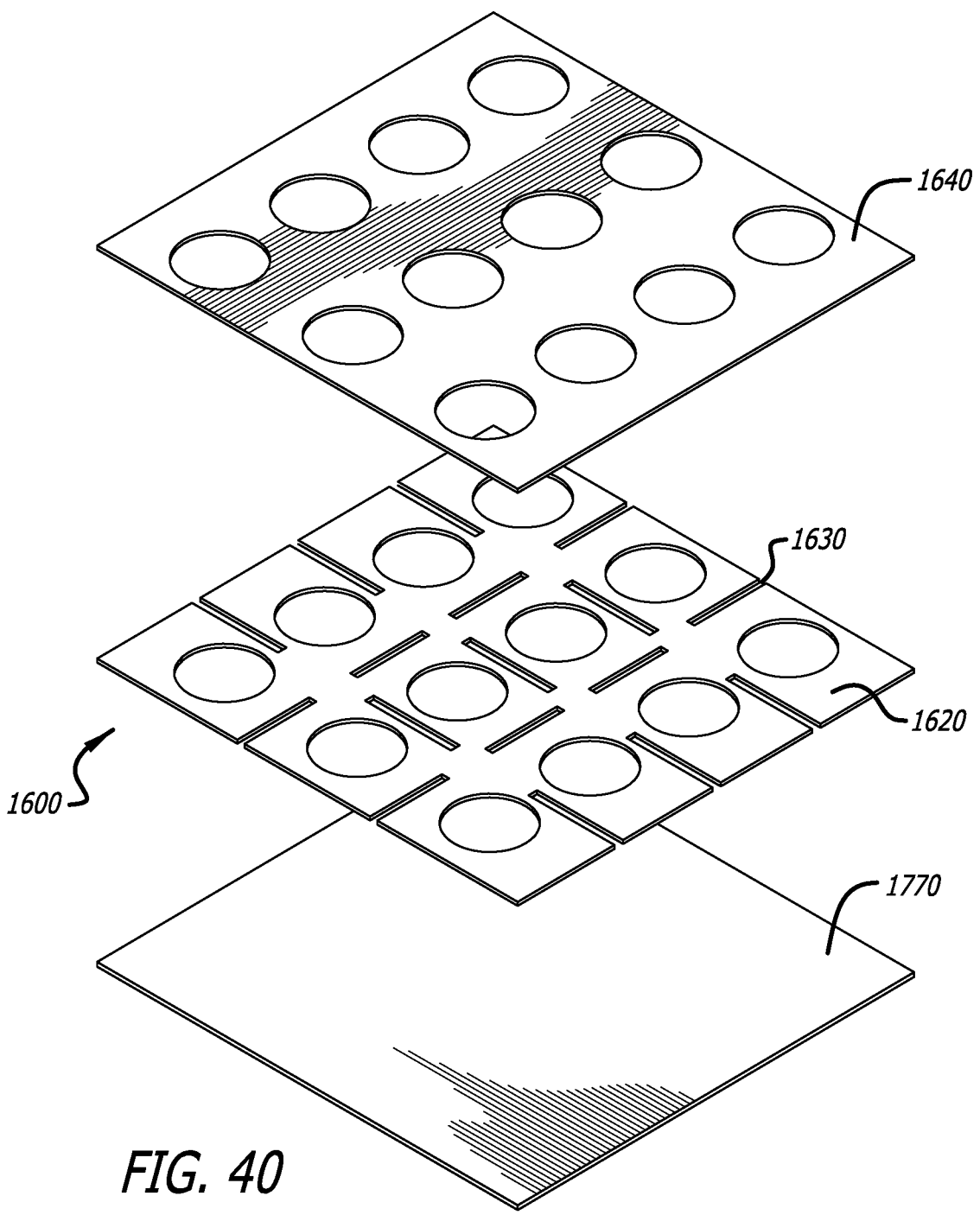
FIG. 40 is an exploded view of a heat transfer (cover) assembly of the module of FIG. 32.
Figure 41:
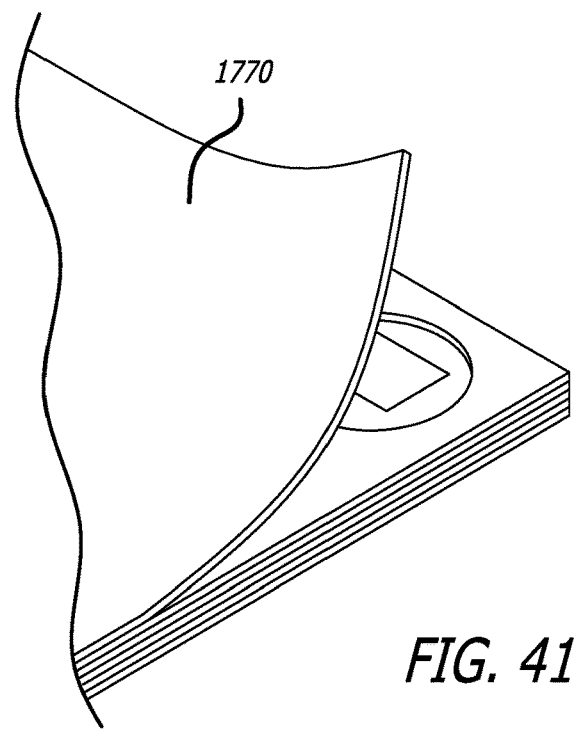
FIG. 41 is an enlarged perspective view of a bottom corner of the module showing a removable coating being peeled away.

The HEM 1100 can include a heat transfer (cover) assembly shown generally at 1600 in FIG. 32. Cover assembly 1600 transmits heat between the body part and the user faces of the TECs 1510. The heat transmission vehicle of the cover assembly 1600 can be a copper or aluminum (or other highly thermally-conductive material) plate 1620 as can be seen in FIGS. 32 and 40. Short, spaced x and y slots 1630 can be formed in the cover plate 1620 to give it greater flexibility and bendability to better conform to rounded and/or angular body parts. A thin sheet or film of plastic 1640 can be adjacent to an inward face of the cover plate 1620. Sheet 1640 can be plasticized to the inward face. It also can extend out beyond the perimeter of the cover plate 1620 and the third sheet 1350 can be sewn or otherwise mechanically secured to the extension perimeter of the plastic sheet to hold at least in part the HEM 1100 together. The sewing is shown by reference numerals 1650 and 1660 in FIG. 32. Other mechanical means in addition to or in lieu of sewing can be used such as snaps, tacks or the like. Additional sewing can be provided through a central part of the HEM 1100 such as through the adhered portions of the third sheet 1350 (outside of the channel) as shown by sewing lines 1670 in FIG. 33. Mechanical attachment means can allow for more flexibility of the layers/components of the HEM than by affixing them with an adhesive, for example.

One or more thermistors (or thermocouples) 1700 (FIG. 36) can be positioned between the cover plate 1620 and the plastic sheet 1640 to accurately measure the temperature of the adjacent body part and transmit this temperature signal to the console 1150 via the wire 1130.

The substance(s) 1530, 1710 used to attach the reference face of the TEC to the copper piece and/or the user face of the TEC to the plate assembly can be a thermally-conductive putty or similar substance (e.g., a thermally-conductive paste, pad or flexible adhesive) which may allow for some planar movement of the TEC, thereby increasing the flexibility/bendability of the HEM 1100. The substance can be very thin on the order of fifty to one hundred microns, and have high thermal conductivity, for example greater than three W/m. This substance can be in lieu of a rigid adhesive affixation.

A biocompatibility layer 1770 can be secured to the outward face of the cover plate 1620. This provides for a smoother, more comfortable and more sanitary contact of the HEM to the body part. Layer 1770 can be considered to be part of the cover assembly 1600 or as an addition thereto. The layer 1770 can be affixed to the plate 1620, it can be a replaceable film or it can be a gel, such as a thermally-conductive silicone gel.

A filler layer 1780 surrounding the TECs 1510 of the TEC assembly can be used. It can be, for example, a foam layer or a core composite layer with pre-formed holes for receiving therein respective ones of the TECs. This layer 1780 can be seen in FIGS. 32 and 42. The core composite material can provide interstitial insulation and structural stability to the HEM.

Figure 44:
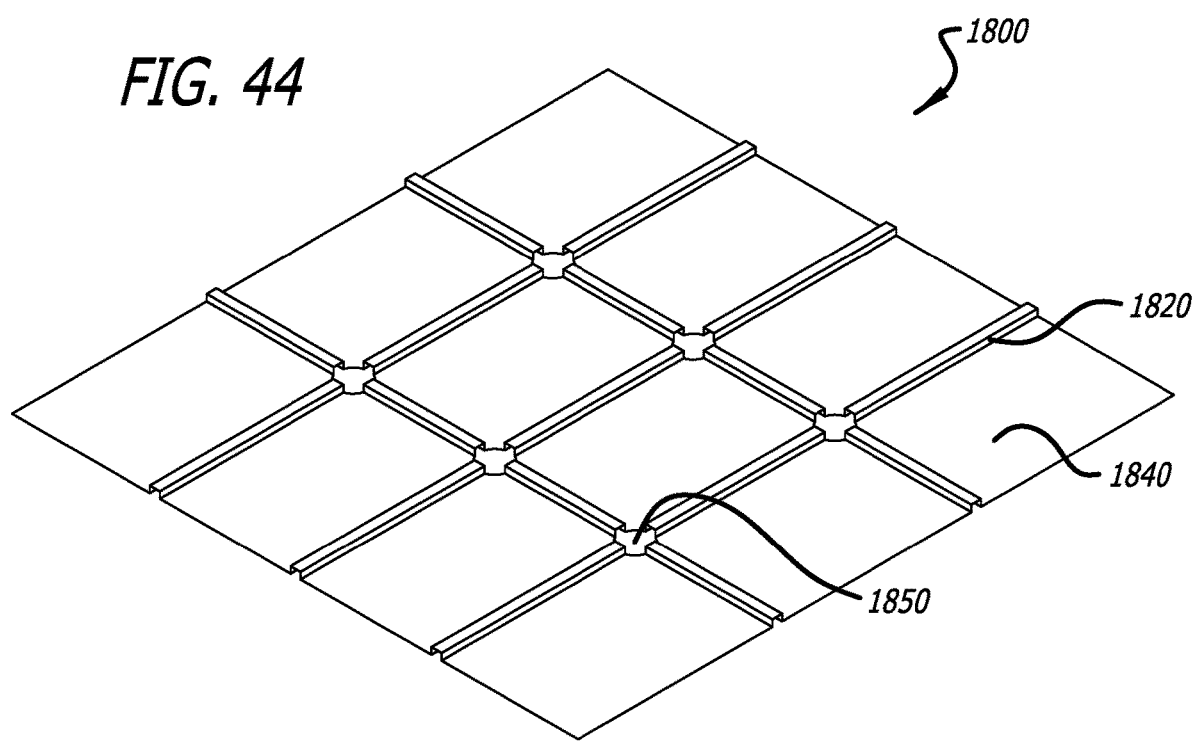
FIG. 44 is a perspective view of an alternative heat transfer (cover) plate of the disclosure illustrated in isolation.

As mentioned above, the cover plate 1620 can be formed with X and/or Y direction slots 1630 to provide for flexibility/bendability. Another construction of the cover plate is shown by plate 1800 in FIG. 44 which has a tic-tac-toe arrangement of bridges 1820 forming an array of interconnected rectangular plates 1840. The intersections of the x and y bridges 1820 can be holes 1850. If the plate 1800 is made of metal, e.g., copper, then so are the bridges 1820 according to the construction of the embodiment depicted in FIG. 44.

Figure 48:
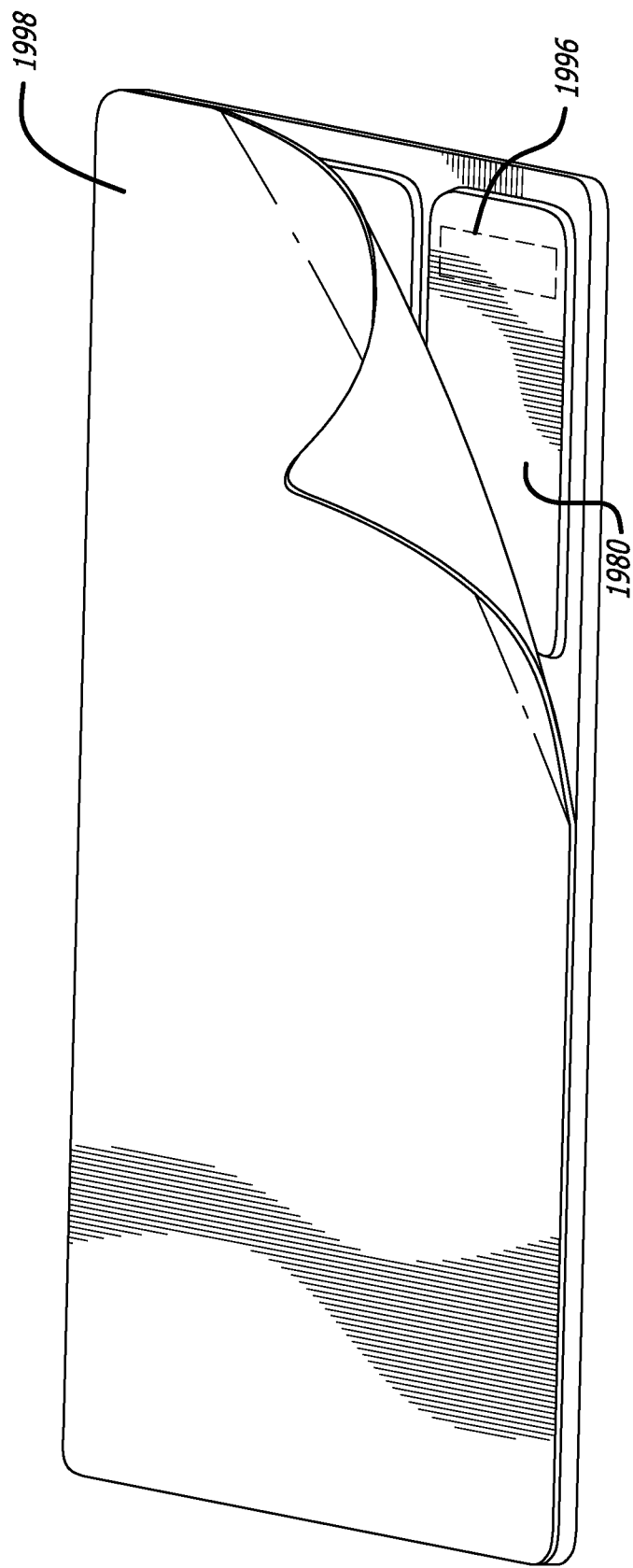
FIG. 48 is a bottom perspective view of an alternative of the cover assembly having a bottom biocompatible layer, shown being peeled back.

An alternative heat distribution cover assembly (or heat transfer assembly) 1900 is illustrated in FIGS. 45 and 48. Cover assembly 1900 can include a frame 1910 which holds the cover assembly together and can be made of a flexible plastic, while the plate assembly 1920 can be made of metal. This plastic construction can have greater flexibility than the copper of plate 1800, for example, and be less subject to bending fatigue. In addition to the frame 1910 and the plate assembly 1920 the alternative cover assembly 1900 can include a tray assembly 1930, as discussed in detail below.

Figure 46:
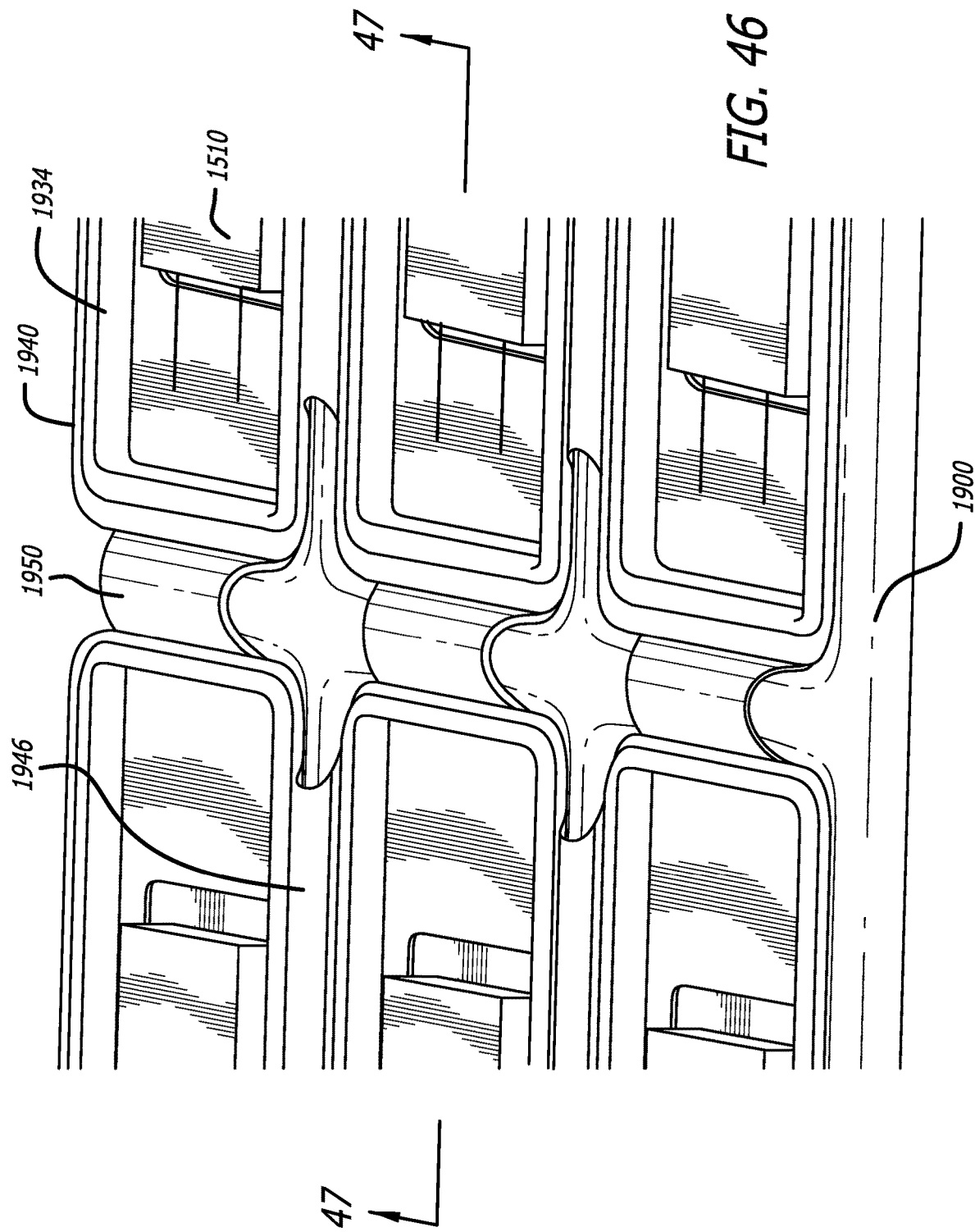
FIG. 46 is an enlarged perspective view of a portion of the cover assembly of FIG. 45 shown assembled.
Figure 47:
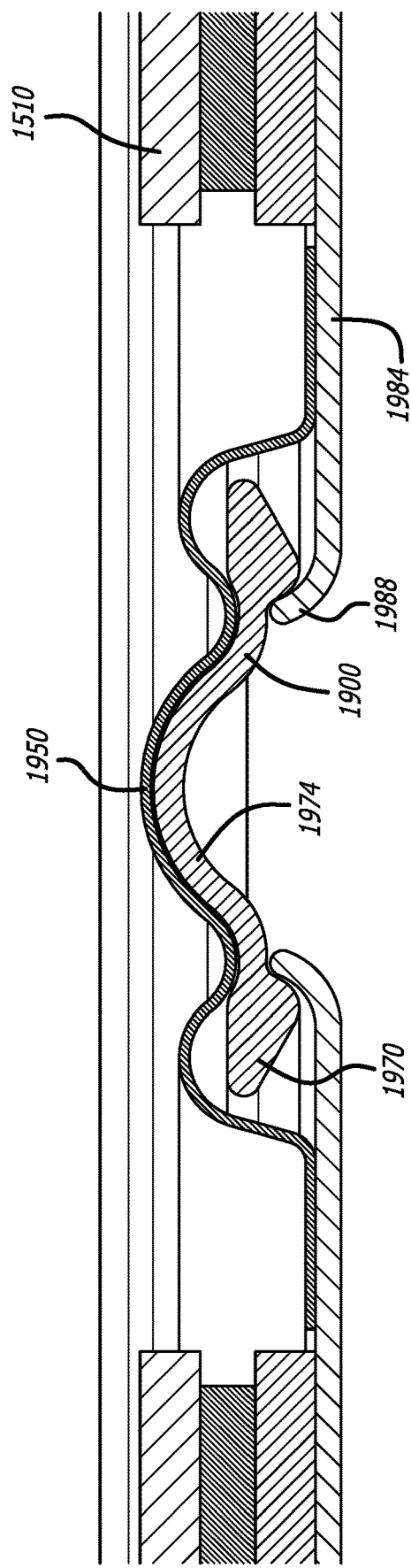
FIG. 47 is an enlarged cross-sectional view taken on line 47-47 of FIG. 46.

The tray assembly 1930 can include a plurality of trays 1934, one for each TEC 1510. Each tray 1934 has a through-hole 1936 for receiving therein a respective TEC 1510 (FIGS. 46 and 47). Each tray also has a perimeter rim 1940. Elongate flexible bridges 1946 interconnect rims 1940 of the long side of adjacent trays 1934. Wider and shorter flexible bridges 1950 interconnect rims 1940 of the short sides of adjacent trays 1934. As can be seen in FIG. 47, smooth curves can connect the bridges with the adjacent rims 1940. The bridges interconnect the trays 1934 such that tray assembly 1830 has a matrix-type construction.

The frame 1810 has x and y bars 1960 forming window-openings 1964. The bars in cross section can be shaped as shown in FIG. 47 with enlarged heads 1970 at both ends connected by a smoothly-curved hump or bridge 1974.

The plate assembly 1920 can include a plurality of thermally-conductive tiles 1980 (copper, aluminum, or any other material with high thermal conductivity) which have flat body members 1984 with raised perimeter lips 1988. The enlarged heads 1970 hook onto or snap onto the perimeter lips 1988 when the cover assembly is assembled as shown in FIGS. 46 and 47. The enlarged heads 1970 are within the rims 1940. The bridges 1950 are on the humps 1974 in conforming relation. As can be understood, each of the plate assembly (tiles), the tray assembly (tiles) and the frame (windows) form the same arrays, e.g., a three-by-three array, which are aligned when assembled such that each TEC can penetrate to thermally contact (directly or using an adhesive or the like) with a respective tile 1980.

Each of the tiles 1980 can have its own thermistor (or thermocouple) 1996 secured to an inward surface thereof. The temperature sensors 1996 collectively and accurately measure the temperature of the adjacent body part.

A number of ways of providing a smooth, comfortable, cleanable, thermally-conductive surface on the bottoms of the tiles for direct contact with the body part and are within the scope of the present disclosure. One is to provide a biocompatible thermally-conductive layer 1998, which for example can be reinforced with carbon fiber/nanotubes/copper mesh (anything to optimize thermal conductivity) to optimize heat extraction via proximity to skin. The layer can be permanently affixed and able to be wiped clean. Or it can be a removable layer 1998 (FIG. 48) which can be applied, used, removed and replaced with a fresh layer.

Another embodiment is to apply a suitable thermally-conductive lacquer directly on the bottom surfaces of the (metal) tiles 980, and which can be wiped clean. A thin, biocompatible, thermally-conductive gel, such as a silicone gel, can also provide the coating according to another embodiment. A further embodiment is to provide a sleeve or bag (not shown) in which the HEM can be inserted. The bag can have a thin biocompatible film (along the lines of those discussed above) on its user contact surface. After each use the bag can be removed, washed and reused.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A heat exchange module, comprising:
   a channel enclosure including a channel for heat-transfer liquid and a thermally-conductive plate assembly which includes thermally-conductive first and second plate pieces for heat transfer with the liquid when present and flowing in the channel;
   a thermoelectric cooler (TEC) assembly which includes a first TEC whose reference side is in heat transfer relation with the first plate piece and a second TEC whose reference side is in heat transfer relation with the second plate piece;
   a heat distribution cover assembly which includes a tray assembly, a plurality of tiles and a frame which holds the tray assembly and the plurality of tiles together;
   the tray assembly including a first tray having a first opening through which a user side of the first TEC is accessible and a second tray having a second opening through which a user side of the second TEC is accessible; and
   the plurality of tiles including a thermally-conductive first tile which is in heat transfer relation with the user side of the first TEC and a thermally-conductive second tile which is in heat transfer relation with the user side of the second TEC;
   wherein the plate assembly includes thermally-conductive third and fourth plate pieces for heat transfer with the liquid when present and flowing in the channel; the TEC assembly includes a third TEC whose reference side is in heat transfer relation with the third plate piece and a fourth TEC whose reference side is in heat transfer relation with the fourth plate piece; the tray assembly including the first tray having the first opening through which the user side of the first TEC passes and the second tray having the second opening through which the user side of the second TEC passes; the plurality of tiles includes a thermally-conductive third tile which is in heat transfer relation with the user side of the third TEC and a thermally-conductive fourth tile which is in heat transfer relation with the user side of the second TEC;

wherein the tiles are arranged in a 2×2 array having an x-axis between the first and second tiles and the third and four tiles, and a y-axis between the first and third tiles and the second and fourth tiles, and the frame allows the 2×2 array to bend about the x-axis and about the y-axis.

2. The module of claim 1, wherein a first temperature sensor is mounted to the first tile and a second temperature sensor is mounted to the second tile.

3. The module of claim 1, wherein the tray assembly includes a hinge connecting the first and second trays.

4. The module of claim 1, wherein the tray assembly includes an elongate bridge connecting adjacent edges of the first and second trays.

5. The module of claim 1, wherein the first opening is configured to hold the first TEC therein.

6. The module of claim 1, wherein the frame allows the first and second tiles to bend relative to one another about an axis between them.

7. The module of claim 1, wherein the tray assembly includes the first, second, third and fourth trays being arranged in a 2×2 array, a first hinge operatively between adjacent edges of the first and second trays, a second hinge operatively between adjacent edges of the first and third trays, a third hinge operatively between adjacent edges of the third tray and the fourth tray and a fourth hinge operatively between adjacent edges of the fourth tray and the second tray.

8. The module of claim 1, wherein the trays each have a tray perimeter rim, and the tiles each have a tile perimeter rim.

9. The module of claim 8, wherein the frame snap-fit or hook-fit holds the plurality of trays and the tiles together via the tray and tile perimeter rims.

10. The module of claim 1, wherein the cover assembly includes a biocompatible coating on outer surface of the tiles.

11. The module of claim 1, wherein: the tray assembly includes the first tray having a first raised edge, the second tray having a second raised edge and a bridge connecting the first and second raised edges; the frame includes a connector member whose cross-section includes first and second enlarged heads on opposite ends of a raised bridge; and the first tile including a raised edge first lip and the second tile including a raised edge second lip.

12. The module of claim 11, wherein the cover assembly when assembled includes: the first lip hooking onto the first enlarged head, the second lip hooking onto the second enlarged head, the raised bridge holding the first and second trays in spaced relation, the bridge being positioned against the raised bridge, the first enlarged head being in the first raised edge and the second enlarged head being in the second raised edge.

13. A heat exchange module, comprising:
a channel enclosure including a channel for heat-transfer liquid and a thermally-conductive plate assembly which includes thermally-conductive first and second plate pieces for heat transfer with the liquid when present and flowing in the channel;
a thermoelectric cooler (TEC) assembly which includes a first TEC whose reference side is in heat transfer relation with the first plate piece and a second TEC whose reference side is in heat transfer relation with the second plate piece;
a heat distribution cover assembly which includes plurality of thermally-conductive tiles and a plastic frame which snap-fit or hook-fit holds the plurality of tiles together; and
the plurality of tiles including a thermally-conductive first tile which is in heat transfer relation with the user side of the first TEC and a thermally-conductive second tile which is in heat transfer relation with the user side of the second TEC.

14. The module of claim 13, further comprising a first temperature sensor secured to an inward side of the first tile and a second temperature sensor secured to an inward side of the second tile.

15. A heat transfer assembly, comprising:
a thermoelectric cooler (TEC) assembly which includes a first TEC whose reference side is configured to be positionable in heat transfer relation with a flow of heat transfer liquid and a second TEC whose reference side is configured to be positionable in heat transfer relation with the flow of the heat transfer liquid;
a heat distribution cover assembly which includes a tray assembly, a plurality of heat-conductive tiles and a frame which holds the tray assembly and the plurality of tiles together;
the tray assembly including a first tray having a first opening through which a user side of the first TEC passes and a second tray having a second opening through which a user side of the second TEC passes; and
the plurality of tiles including a thermally-conductive first tile which is in heat transfer relation with the user side of the first TEC and a thermally-conductive second tile which is in heat transfer relation with the user side of the second TEC;
wherein the first and second trays each include tray perimeter rims and the first and second tiles each include tile perimeter rims, and the frame snap-fit or hook-fit holds the first and second trays and the first and second tiles together via the tray and tile perimeter rims, allowing flexing between the tiles along an axis between them.

16. The assembly of claim 15, wherein the frame is a plastic frame including a plurality of open windows, each for a respective tray of the tray assembly.

17. A heat exchange module, comprising:
a channel enclosure including a channel for heat-transfer liquid and a thermally-conductive plate assembly which includes thermally-conductive first and second plate pieces for heat transfer with the liquid when present and flowing in the channel;
a thermoelectric cooler (TEC) assembly which includes a first TEC whose reference side is in heat transfer relation with the first plate piece and a second TEC whose reference side is in heat transfer relation with the second plate piece;
a heat distribution cover assembly which includes a tray assembly, a plurality of tiles and a frame which holds the tray assembly and the plurality of tiles together;

the tray assembly including a first tray having a first opening through which a user side of the first TEC is accessible and a second tray having a second opening through which a user side of the second TEC is accessible; and the plurality of tiles including a thermally-conductive first tile which is in heat transfer relation with the user side of the first TEC and a thermally-conductive second tile which is in heat transfer relation with the user side of the second TEC;

wherein the plate assembly includes thermally-conductive third and fourth plate pieces for heat transfer with the liquid when present and flowing in the channel; the TEC assembly includes a third TEC whose reference side is in heat transfer relation with the third plate piece and a fourth TEC whose reference side is in heat transfer relation with the fourth plate piece; the tray assembly including the first tray having the first opening through which the user side of the first TEC passes and the second tray having the second opening through which the user side of the second TEC passes; the plurality of tiles includes a thermally-conductive third tile which is in heat transfer relation with the user side of the third TEC and a thermally-conductive fourth tile which is in heat transfer relation with the user side of the second TEC;

wherein the tray assembly includes the first, second, third and fourth trays being arranged in a 2×2 array, a first hinge operatively between adjacent edges of the first and second trays, a second hinge operatively between adjacent edges of the first and third trays, a third hinge operatively between adjacent edges of the third tray and the fourth tray and a fourth hinge operatively between adjacent edges of the fourth tray and the second tray.

18. A heat exchange module, comprising:

a channel enclosure including a channel for heat-transfer liquid and a thermally-conductive plate assembly which includes thermally-conductive first and second plate pieces for heat transfer with the liquid when present and flowing in the channel;

a thermoelectric cooler (TEC) assembly which includes a first TEC whose reference side is in heat transfer relation with the first plate piece and a second TEC whose reference side is in heat transfer relation with the second plate piece;

a heat distribution cover assembly which includes a tray assembly, a plurality of tiles and a frame which holds the tray assembly and the plurality of tiles together;

the tray assembly including a first tray having a first opening through which a user side of the first TEC is accessible and a second tray having a second opening through which a user side of the second TEC is accessible; and the plurality of tiles including a thermally-conductive first tile which is in heat transfer relation with the user side of the first TEC and a thermally-conductive second tile which is in heat transfer relation with the user side of the second TEC;

wherein the trays each have a tray perimeter rim, and the tiles each have a tile perimeter rim;

wherein the frame snap-fit or hook-fit holds the plurality of trays and the tiles together via the tray and tile perimeter rims.

19. The module of claim 18, wherein a first temperature sensor is mounted to the first tile and a second temperature sensor is mounted to the second tile.

20. The module of claim 18, wherein the tray assembly includes a flexible hinge connecting the first and second trays.

21. The module of claim 18, wherein the tray assembly includes an elongate bridge connecting adjacent edges of the first and second trays.

22. The module of claim 18, wherein the first opening is configured to hold the first TEC therein.

23. The module of claim 18, wherein the frame allows the first and second tiles to bend relative to one another about an axis between them.

24. The module of claim 18, wherein: the plate assembly includes thermally-conductive third and fourth plate pieces for heat transfer with the liquid when present and flowing in the channel; the TEC assembly includes a third TEC whose reference side is in heat transfer relation with the third plate piece and a fourth TEC whose reference side is in heat transfer relation with the fourth plate piece; the tray assembly including the first tray having the first opening through which the user side of the first TEC passes and the second tray having the second opening through which the user side of the second TEC passes; the plurality of tiles includes a thermally-conductive third tile which is in heat transfer relation with the user side of the third TEC and a thermally-conductive fourth tile which is in heat transfer relation with the user side of the second TEC.

25. The module of claim 24, wherein the tray assembly includes the first, second, third and fourth trays being arranged in a 2×2 array, a first hinge operatively between adjacent edges of the first and second trays, a second hinge operatively between adjacent edges of the first and third trays, a third hinge operatively between adjacent edges of the third tray and the fourth tray and a fourth hinge operatively between adjacent edges of the fourth tray and the second tray.

26. The module of claim 24, wherein the tiles are arranged in a 2×2 array having an x-axis between the first and second tiles and the third and four tiles, and a y-axis between the first and third tiles and the second and fourth tiles, and the frame allows the 2×2 array to bend about the x-axis and about the y-axis.

27. The module of claim 18, wherein the cover assembly includes a biocompatible coating on outer surface of the tiles.

28. The module of claim 18, wherein: the tray assembly includes the first tray having a first raised edge, the second tray having a second raised edge and a bridge connecting the first and second raised edges; the frame includes a connector member whose cross-section includes first and second enlarged heads on opposite ends of a raised bridge; and the first tile including a raised edge first lip and the second tile including a raised edge second lip.

29. The module of claim 28, wherein the cover assembly when assembled includes: the first lip hooking onto the first enlarged head, the second lip hooking onto the second enlarged head, the raised bridge holding the first and second trays in spaced relation, the bridge being positioned against the raised bridge, the first enlarged head being in the first raised edge and the second enlarged head being in the second raised edge.

30. A heat exchange module, comprising:

a channel enclosure including a channel for heat-transfer liquid and a thermally-conductive plate assembly which includes thermally-conductive first and second plate pieces for heat transfer with the liquid when present and flowing in the channel;

a thermoelectric cooler (TEC) assembly which includes a first TEC whose reference side is in heat transfer relation with the first plate piece and a second TEC whose reference side is in heat transfer relation with the second plate piece;

a heat distribution cover assembly which includes a tray assembly, a plurality of tiles and a frame which holds the tray assembly and the plurality of tiles together;

the tray assembly including a first tray having a first opening through which a user side of the first TEC is accessible and a second tray having a second opening through which a user side of the second TEC is accessible; and the plurality of tiles including a thermally-conductive first tile which is in heat transfer relation with the user side of the first TEC and a thermally-conductive second tile which is in heat transfer relation with the user side of the second TEC;

wherein the tray assembly includes the first tray having a first raised edge, the second tray having a second raised edge and a bridge connecting the first and second raised edges; the frame includes a connector member whose cross-section includes first and second enlarged heads on opposite ends of a raised bridge; and the first tile including a raised edge first lip and the second tile including a raised edge second lip.

31. The module of claim 30, wherein the cover assembly when assembled includes: the first lip hooking onto the first enlarged head, the second lip hooking onto the second enlarged head, the raised bridge holding the first and second trays in spaced relation, the bridge being positioned against the raised bridge, the first enlarged head being in the first raised edge and the second enlarged head being in the second raised edge.

* * * * *